(12) United States Patent
Lo

(10) Patent No.: US 12,090,149 B2
(45) Date of Patent: Sep. 17, 2024

(54) SMAD3 INHIBITORS

(71) Applicant: Moexa Pharmaceuticals Limited, Hong Kong (CN)

(72) Inventor: Ho Yin Lo, Bethel, CT (US)

(73) Assignee: Moexa Pharmaceuticals Limited, Hong Kong (CN)

( * ) Notice: Subject to any disclaimer, the term of this patent is extended or adjusted under 35 U.S.C. 154(b) by 706 days.

(21) Appl. No.: 17/265,502

(22) PCT Filed: Aug. 6, 2019

(86) PCT No.: PCT/CN2019/099521
§ 371 (c)(1),
(2) Date: Feb. 2, 2021

(87) PCT Pub. No.: WO2020/029980
PCT Pub. Date: Feb. 13, 2020

(65) Prior Publication Data
US 2021/0299117 A1    Sep. 30, 2021

Related U.S. Application Data

(60) Provisional application No. 62/715,120, filed on Aug. 6, 2018.

(51) Int. Cl.
| A61K 31/4725 | (2006.01) |
| A61K 45/06 | (2006.01) |
| A61P 35/00 | (2006.01) |
| C07D 471/04 | (2006.01) |

(52) U.S. Cl.
CPC .......... *A61K 31/4725* (2013.01); *A61K 45/06* (2013.01); *A61P 35/00* (2018.01); *C07D 471/04* (2013.01)

(58) Field of Classification Search
CPC .. A61K 31/4725; A61K 45/06; A61K 31/352; A61K 31/437; A61K 31/496; A61K 31/519; A61K 31/5377; A61K 31/5025; A61P 35/00; C07D 471/04; C07D 487/04
See application file for complete search history.

(56) References Cited

U.S. PATENT DOCUMENTS

| 9,505,765 | B2 * | 11/2016 | Jacobsen | A61K 31/53 |
| 2002/0022624 | A1 * | 2/2002 | Dinnell | C07D 471/04 544/125 |
| 2005/0020593 | A1 | 1/2005 | Maillet et al. | |
| 2013/0317003 | A1 | 11/2013 | Jacques et al. | |
| 2014/0120116 | A1 | 5/2014 | Lan | |

FOREIGN PATENT DOCUMENTS

| AU | 66035/86 | 6/1987 | |
| CN | 104768546 | 7/2015 | |
| CN | 105120860 | 12/2015 | |
| CN | 1826319 | 8/2016 | |
| DE | 3542661 A1 * | 6/1987 | ............... A61P 7/10 |
| EP | 0225522 | 6/1987 | |
| JP | 2013253065 | 12/2013 | |
| WO | 0214313 A2 | 2/2002 | |
| WO | WO 2005009947 | 2/2005 | |
| WO | WO 2012045729 | 4/2012 | |
| WO | WO 2013033116 | 3/2013 | |
| WO | WO 2014018888 | 1/2014 | |
| WO | WO 2014063659 | 5/2014 | |
| WO | 2015078417 A1 | 6/2015 | |
| WO | WO 2015083028 | 6/2015 | |
| WO | WO 2016177658 | 11/2016 | |

OTHER PUBLICATIONS

Meyer, Horst. DE-3542661-A1, Jun. 1987, English Translation. (Year: 1987).*
Tang, P. M. K., et al, Smad3 promotes cancer progression by inhibiting E4BP4-mediated NK cell development, Nature Communications. 8, 14677, 2017. (Year: 2017).*
Fuchs, K., WO 02/14313, English Translation, 2002. (Year: 2002).*
Yang, Y., et al. Cancer Cell. 2006; 9(6): 445-457. (Year: 2006).*
Millet, C., et al., Crit Rev Eukaryot Gene Expr. 2007; 17(4): 281-293. (Year: 2007).*

(Continued)

*Primary Examiner* — Eric Olson
*Assistant Examiner* — Samuel L Galster
(74) *Attorney, Agent, or Firm* — Norton Rose Fulbright US LLP

(57) ABSTRACT

Smad3 inhibitor compounds, specifically a compound of Formula 1 or Formula 2, or a pharmaceutically acceptable salt thereof, and its use in treating or preventing cell proliferation or cancer in a subject are provided.

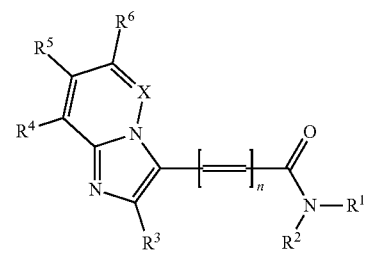

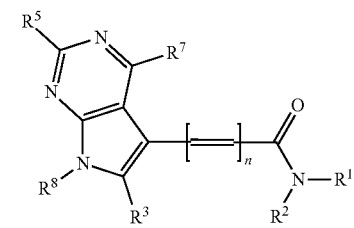

16 Claims, 3 Drawing Sheets

(56) References Cited

OTHER PUBLICATIONS

Nam, K. T., et al. Laboratory Investigation. (2012) 92, 883-895. (Year: 2012).*
Yamazaki, K., et al. Laboratory Investigation (2014) 94, 683-691. (Year: 2014).*
Tang, P. M., et al. Nature Communications. volume 8, Article No. 14677. (Year: 2017).*
Singha, P. K., et al. Genes & Cancer, vol. 10 (5-6). (Year: 2019).*
Jeon, H. et al., Nucleic Acids Research. 2023, vol. 51, No. 6 2655-2670 (Year: 2023).*
"RN1922560-45-9, RN 1922555-55-2, et al." STN Registry, Jun. 1, 2016 (Jun. 1, 2016).
M. Jinnin et al. "Characterization of SIS3, a Novel Specific Inhibitor of Smad3, Factor-betal-Induced Extracellular Matrix Expression", *Molecular Pharmacology*, vol. 69, No. 2, Jan. 2006, pp. 597-607.
Lad Nitin et al. "Piperlongumine derived cyclic sulfonamides (sultams): Synthesis andin vitroexploration for therapeutic potential against HeLa cancer cell lines", *European Journal of Medicinal Chemistry, Elsevier*, Amsterdamn, NL. vol. 126, Dec. 10, 2016 pp. 870-878.
Li Y et al. "Design, synthesis and antiproliferative activities of novel benzamide derivatives ad HDAC inhibitors", *European Journal of Medicinal Chemistry*, vol. 100, Jun. 5, 2015, pp. 270-276.
Extended European Search Report issued in corresponding European Application No. 19846801.9 dated May 10, 2022.
Database Registry [Online] Chemical Abstracts Service, Columbus, Ohio May 21, 2018. Database accession No. 2224435-50-9.
Database Registry [Online] Chemical Abstracts Service, Columbus, Ohio May 20, 2018, Database accession No. 2224343-17-1.
Database Registry [Online] Chemical Abstracts Service, Columbus, Ohio, Sep. 28, 2009, Database accession No. 1186404-55-6.
Database Registry [Online] Chemical Abstracts Service, Columbus, Ohio May 20, 2018, Database accession No. 2224241-41-0.
Database Registry [Online] Chemical Abstracts Service, Columbus, Ohio May 20, 2018, Database accession No. 2224298-21-7.
Database Registry [Online] Chemical Abstracts Service, Columbus, Ohio May 20, 2018, Database accession No. 2224301-00-0.
CAS Records cited in corresponding Chinese Office Action, dated Dec. 22, 2022; (D7); 20 pages.
Office Action issued in corresponding Chinese Application No. 201980052396.5, dated Dec. 22, 2022 (English Translation); 15 pages.
CAS Records cited in the International Search Report & Written Opinion, dated Oct. 30, 2019; (D5); 15 pages.
International Search Report & Written Opinion issued in PCT/CN2019/099521, dated Oct. 30, 2019; 13 pages.
CAS Records cited in corresponding European Office Action, dated Nov. 9, 2022; (D19 and D21-25); 7 pages.
Office Action issued in corresponding European Application No. 19846801.9, dated Nov. 9, 2023; 13 pages.

* cited by examiner

SMAD3 INHIBITORS

CROSS-REFERENCE TO RELATED APPLICATIONS

The present application is a U.S. National Stage patent application of International Patent Application No. PCT/CN2019/099521, filed on Aug. 6, 2019, which claims the benefit of U.S. Provisional Application No. 62/715,120, filed on Aug. 6, 2018, the benefit of which is claimed and the disclosures of which are incorporated herein by reference in their entireties.

FIELD

This disclosure relates to Smad3 inhibitor compounds. This disclosure also relates to compositions and formulations comprising the Smad3 inhibitor compounds. This disclosure also relates to processes for preparing the Smad3 inhibitor compounds, or compositions or formulations comprising the Smad3 inhibitor compounds. This disclosure also relates to various uses and methods for treating proliferative disorders or diseases such as cancers involving the Smad3 inhibitor compounds, or compositions or formulations thereof.

BACKGROUND

Cancer is a generic term for a large group of diseases that can affect any part of the body. One defining feature of cancer is the rapid proliferation of abnormal cells that grow beyond their usual boundaries. Cancer cells can then invade adjoining parts of the body and spread to other organs in a process known as metastasis. Metastasis is the main cause of death from cancer and can also be promoted by the cells surrounding the cancer called cancer stromal cells or cancer micro-environments.

According to the World Health Organization (WHO), cancer is a leading cause of death worldwide, accounting for 7.6 million deaths (around 13% of all deaths) in 2008. Lung, stomach, liver, colon and breast cancer cause the most cancer deaths each year. Despite intense research effort and technological advancement in biomedical sciences, deaths from cancer worldwide are projected to continue rising, with an estimated 13.1 million deaths in 2030.

Because of the prevalence of cancer and its significant impact on humanity, there remains an urgent need to develop new and more effective strategies for cancer treatment. The present disclosure addresses this and other related needs in that it provides alternative Smad3 inhibitor compounds that can inhibit cancer cell growth and supportive function of the cancer microenvironment.

SUMMARY

The present inventors have identified novel and alternative Smad3 inhibitor compounds, which may be used in the treatment of cancers. The Smad3 inhibitor compounds, at least according to some embodiments described herein, may also provide further advantages such as enhanced solubility, oral bioavailability or stability properties. The Smad3 inhibitor compounds, compositions, formulations, uses, or methods comprising the compounds, may be useful for inhibiting proliferation of a cell based on the understanding that Smad3-mediated cellular signal transduction plays a significant role in the development and progression of cancer, especially the types that are responsive to TGF-β stimulation, including cancer cells and cancer stromal cells such as vascular endothelial cells, fibroblasts, neutrophils, eosinophils, mast cells, T cells and subsets, B cells, macrophages, and NK cells.

Accordingly, in a first aspect there is provided a compound of Formula 1 or Formula 2, or a pharmaceutically acceptable salt thereof:

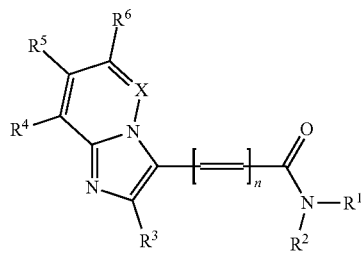

Formula 1

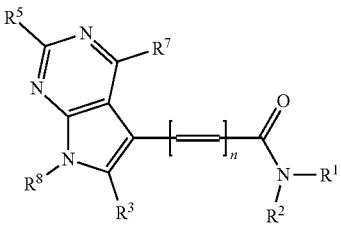

Formula 2 wherein n represents 0 or 1;

X represents N or $CR^7$;

$R^1$ and $R^2$ are each independently selected from hydrogen, $C_{1-20}$alkyl, $C_{2-20}$alkenyl, $C_{2-20}$alkynyl, monocyclic or polycyclic carbocyclic, and monocyclic or polycyclic heterocyclic; or $R^1$ and $R^2$ join together to form a monocyclic or polycyclic heterocyclic; wherein the $C_{1-20}$alkyl, $C_{2-20}$alkenyl, $C_{2-20}$alkynyl, are each optionally interrupted with one or more heteroatoms independently selected from O, N and S; and wherein the $C_{1-20}$alkyl, $C_{2-20}$alkenyl, $C_{2-20}$alkynyl, carbocyclic, and heterocyclic, are each optionally substituted with one or more substituents independently selected from halo, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; wherein $R^9$ and $R^{10}$ are each independently selected from hydrogen, $C_{1-10}$alkyl, aryl$C_{1-10}$alkyl, hetaryl$C_{1-10}$alkyl, and heterocyclic, and wherein the $C_{1-10}$alkyl moiety of any one of these groups is optionally interrupted with one or more heteroatoms independently selected from O, N and S, and the $C_{1-10}$alkyl, aryl$C_{1-10}$alkyl, hetaryl$C_{1-10}$alkyl, and heterocyclic groups, are each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$; wherein $R^{11}$ and $R^{12}$ are each independently selected from hydrogen, $C_{1-6}$alkyl, and $C_{1-6}$alkylhalo;

$R^3$, $R^4$, $R^5$, $R^6$, and $R^7$, when present, are each independently selected from hydrogen, halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups are each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, are each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$; wherein $R^{11}$ and $R^{12}$ are each independently selected from hydrogen, $C_{1-6}$alkyl, and $C_{1-6}$alkylhalo; and $R^8$, when present, is selected from hydrogen, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups are each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, are each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$; wherein $R^{11}$ and $R^{12}$ are each independently selected from hydrogen, $C_{1-6}$alkyl, and $C_{1-6}$alkylhalo.

The compound of Formula 1 may be selected from a compound of Formula 1a or Formula 1b, or a pharmaceutically acceptable salt thereof:

Formula 1a

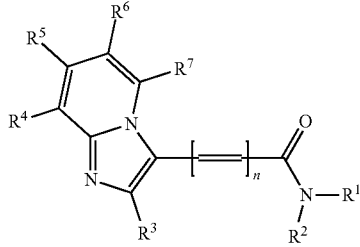

Formula 1b

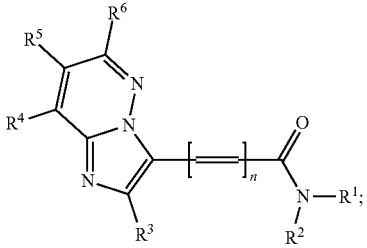

wherein n, $R^1$, $R^2$, $R^3$, $R^4$, $R^5$, $R^6$, and $R^7$, may be provided according to any embodiments as described herein.

The compound of Formula 1 or Formula 1a may be selected from a compound of Formula 1a(i) or Formula 1a(ii), or a pharmaceutically acceptable salt thereof:

Formula 1a(i)

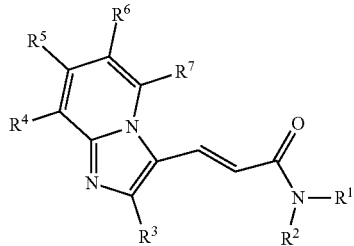

Formula 1a(ii)

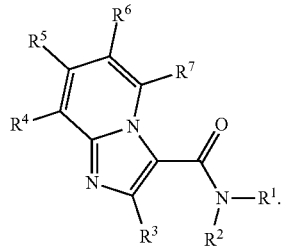

wherein $R^1$, $R^2$, $R^3$, $R^4$, $R^5$, $R^6$, and $R^7$, may be provided according to any embodiments as described herein.

The compound of Formula 1 or Formula 1b may be selected from a compound of Formula 1b(i) or Formula 1b(ii), or a pharmaceutically acceptable salt thereof:

Formula 1b(i)

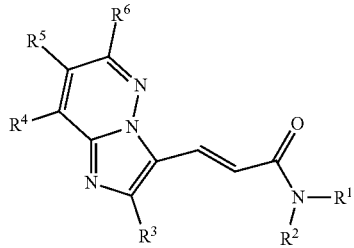

Formula 1b(ii)

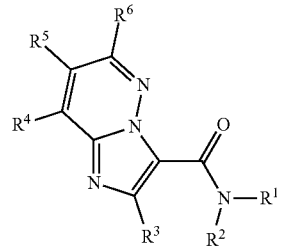

wherein $R^1$, $R^2$, $R^3$, $R^4$, $R^5$, $R^6$, and $R^7$, may be provided according to any embodiments as described herein.

The compound of Formula 2 may be selected from a compound of Formula 2a(i) or Formula 2a(ii), or a pharmaceutically acceptable salt thereof:

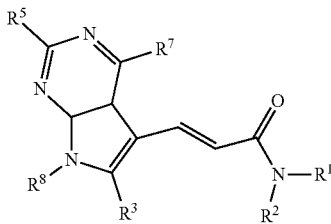

Formula 2a(i)

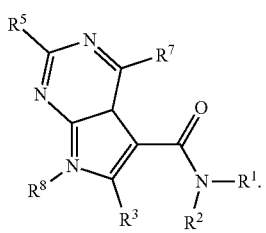

Formula 2a(ii)

wherein $R^1$, $R^2$, $R^3$, $R^5$, $R^7$, and $R^8$, may be provided according to any embodiments as described herein.

$R^1$ and $R^2$ may be each independently selected from hydrogen, $C_{1-20}$alkyl, $C_{2-20}$alkenyl, $C_{2-20}$alkynyl, monocyclic or polycyclic carbocyclic, and monocyclic or polycyclic heterocyclic; the $C_{1-20}$alkyl, $C_{2-20}$alkenyl, $C_{2-20}$alkynyl, may be each optionally interrupted with 1 to 3 heteroatoms independently selected from O, N and S; and the $C_{1-20}$alkyl, $C_{2-20}$alkenyl, $C_{2-20}$alkynyl, carbocyclic, and heterocyclic, may be each optionally substituted with one or more substituents independently selected from halo, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and $R^9$ and $R^{10}$ may be each independently selected from hydrogen, $C_{1-10}$alkyl, aryl$C_{1-10}$alkyl, hetaryl$C_{1-10}$alkyl, and heterocyclic; and the $C_{1-10}$alkyl, aryl$C_{1-10}$alkyl, hetaryl$C_{1-10}$alkyl, and heterocyclic groups may be each optionally substituted with one or more substituents independently selected from halo, CN, $NO_2$, OC(O) $R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$; and wherein $R^{11}$ and $R^{12}$ may be each independently selected from hydrogen and $C_{1-6}$alkyl.

$R^1$ and $R^2$ may be each independently selected from hydrogen and $C_{1-10}$alkyl; the $C_{1-10}$alkyl may be optionally interrupted with 1 to 3 heteroatoms independently selected from O, N and S, and optionally substituted with one or more substituents independently selected from halo, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and $R^9$ and $R^{10}$ may be each independently selected from hydrogen and $C_{1-6}$alkyl.

$R^1$ and $R^2$ may be joined together to form a monocyclic or polycyclic heterocyclic optionally substituted with one or more substituents independently selected from halo, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and $R^9$ and $R^{10}$ may be each independently selected from hydrogen, $C_{1-10}$alkyl, aryl$C_{1-10}$alkyl, hetaryl$C_{1-10}$alkyl, and heterocyclic; and the $C_{1-10}$alkyl, aryl$C_{1-10}$alkyl, hetaryl$C_{1-10}$alkyl, and heterocyclic groups may be each optionally substituted with one or more substituents independently selected from halo, CN, $NO_2$, OC(O) $R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$; and wherein $R^{11}$ and $R^{12}$ may be each independently selected from hydrogen and $C_{1-6}$alkyl.

The monocyclic or polycyclic heterocyclic may be an optionally substituted fully or partially saturated heterocyclic. The polycyclic heterocyclic may be a 5 or 6 membered heterocyclic ring fused with an optionally substituted monocyclic carbocyclic group. The monocyclic or polycyclic heterocyclic may be selected from a group of Formula 3 or Formula 4:

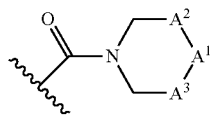

Formula 3

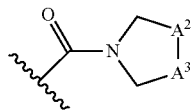

Formula 4 wherein $A^1$ may be selected from O, S, $NR^{14}$, and $CR^{14}R^{15}$;

$A^2$ and $A^3$ may be each independently selected from $CR^{14}R^{15}$;

$R^{14}$ and $R^{15}$ may be each independently selected from hydrogen, $C_{1-10}$alkyl, $C_{2-10}$alkenyl, $C_{2-10}$alkenyl, monocyclic or polycyclic carbocyclic, and monocyclic or polycyclic heterocyclic; or $R^{14}$ and $R^{15}$ if present may join together to form a carbocyclic or heterocyclic ring; the $C_{1-10}$alkyl, $C_{2-10}$alkenyl, $C_{2-10}$alkynyl, may be each optionally interrupted with one or more heteroatoms independently selected from O, N and S; and the $C_{1-10}$alkyl, $C_{2-10}$alkenyl, $C_{2-10}$alkynyl, carbocyclic, heterocyclic group, and heterocyclic ring, may be each optionally substituted with one or more substituents independently selected from halo, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and $R^9$ and $R^{10}$ may be each independently selected from hydrogen, $C_{1-10}$alkyl, aryl$C_{1-10}$alkyl, hetaryl$C_{1-10}$alkyl, and heterocyclic; the $C_{1-10}$alkyl moiety of any one of these groups may be optionally interrupted with one or more heteroatoms independently selected from O, N and S; and the $C_{1-10}$alkyl, aryl$C_{1-10}$alkyl, hetaryl$C_{1-10}$alkyl, and heterocyclic groups may be each optionally substituted with 1 to 3 substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$; and $R^{11}$ and $R^{12}$ are each independently selected from hydrogen, $C_{1-6}$alkyl, and $C_{1-6}$alkylhalo.

The group of Formula 3 may be selected from a group of Formula 3a, 3b, or 3c:

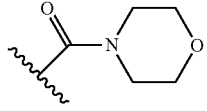

Formula 3a

-continued

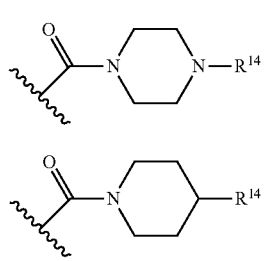
Formula 3b

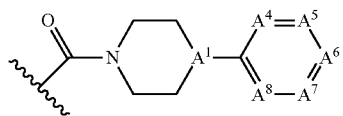
Formula 3c wherein
$R^{14}$ may be selected from hydrogen, $C_{1-10}$alkyl, $C_{2-10}$alkenyl, $C_{2-10}$alkenyl, monocyclic or polycyclic carbocyclic, and monocyclic or polycyclic heterocyclic; the $C_{1-10}$alkyl, $C_{2-10}$alkenyl, $C_{2-10}$alkynyl, may be each optionally interrupted with one or more heteroatoms independently selected from O, N and S; and the $C_{1-10}$alkyl, $C_{2-10}$alkenyl, $C_{2-10}$alkynyl, carbocyclic, heterocyclic group, may be each optionally substituted with one or more substituents independently selected from halo, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and $R^9$ and $R^{10}$ may be each independently selected from hydrogen, $C_{1-10}$alkyl, aryl$C_{1-10}$alkyl, hetaryl$C_{1-10}$alkyl, and heterocyclic; the $C_{1-10}$alkyl moiety of any one of these groups may be optionally interrupted with one or more heteroatoms independently selected from O, N and S; and the $C_{1-10}$alkyl, aryl$C_{1-10}$alkyl, hetaryl$C_{1-10}$alkyl, and heterocyclic groups may be each optionally substituted with 1 to 3 substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$; and $R^{11}$ and $R^{12}$ may be each independently selected from hydrogen and $C_{1-6}$alkyl.

The group of Formula 3 may be selected from a group of Formula 3d or 3e:

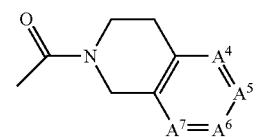
Formula 3d

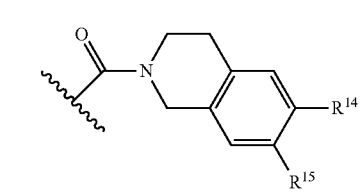
Formula 3e wherein
$A^1$ may be selected from N and CH;
$A^4$, $A^5$, $A^6$, $A^7$, and $A^8$, may be each independently selected from N and $CR^{14}$;
$R^{14}$ may be selected from hydrogen, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and
$R^9$ and $R^{10}$ may be each independently selected from hydrogen, $C_{1-10}$alkyl, aryl$C_{1-10}$alkyl, hetaryl$C_{1-10}$alkyl, and heterocyclic; the $C_{1-10}$alkyl moiety of any one of these groups may be optionally interrupted with one or more heteroatoms independently selected from O, N and S; and the $C_{1-10}$alkyl, aryl$C_{1-10}$alkyl, hetaryl$C_{1-10}$alkyl, and heterocyclic groups may be each optionally substituted with 1 to 3 substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$; and $R^{11}$ and $R^{12}$ may be each independently selected from hydrogen and $C_{1-6}$alkyl.

The group of Formula 3d or Formula 3e may be selected from one of the following groups:

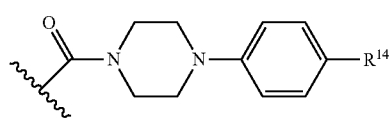
Formula 3d(i)

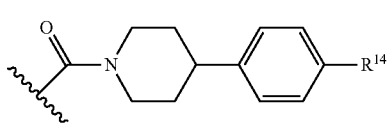
Formula 3d(ii)

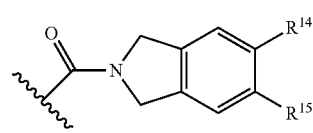
Formula 3e(i)

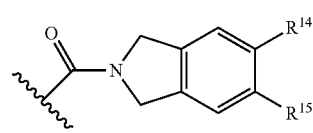
Formula 3e(i)

wherein $R^{14}$ and $R^{15}$ may be provided according to any embodiments as described herein.

$R^{14}$ and $R^{15}$ may be each independently selected from hydrogen, $C(O)NR^9R^{10}$, $OR^9$, and $NR^9R^{10}$; and $R^9$ and $R^{10}$ may be each independently selected from hydrogen, $C_{1-6}$alkyl, monocyclic aryl$C_{1-6}$alkyl, monocyclic hetaryl$C_{1-6}$alkyl, and monocyclic heterocyclic, wherein the $C_{1-6}$alkyl moiety of any one of these groups may be optionally interrupted with one or more heteroatoms independently selected from O, N and S, and the $C_{1-6}$alkyl, monocyclic aryl$C_{1-6}$alkyl, monocyclic hetaryl$C_{1-6}$alkyl, and monocyclic heterocyclic, may be optionally substituted with 1 to 3 substituents independently selected from halo, CN, $NH_2$, OH, and $OC_{1-6}$alkyl.

$R^3$, $R^4$, $R^5$, $R^6$, and $R^7$, may be each independently selected from hydrogen, halo, OH, CN, $NO_2$, $NH_2$, $C_{1-10}$alkyl, monocyclic heterocyclic, and monocyclic aryl; wherein the $C_{1-10}$alkyl may be optionally interrupted with one or more heteroatoms selected from O, N and S, and wherein the $C_{1-10}$alkyl, heterocyclic, and aryl groups, may be each optionally substituted with one or more substituents independently selected from halo, OH, CN, $NO_2$, $NH_2$, $C_{1-6}$alkyl, and $C_{1-6}$alkylhalo.

$R^3$ may be selected from hydrogen, halo, $C_{1-6}$alkyl, $C_{1-6}$alkylhalo, and monocyclic heterocyclic, and monocyclic aryl or heteroaryl. $R^4$, $R^5$, $R^6$, and $R^7$, may be each independently selected from hydrogen, halo, $C_{1-6}$alkyl, and $C_{1-6}$alkylhalo. $R^8$, when present, may be selected from hydrogen, $C_{1-6}$alkyl, $C_{1-6}$alkylhalo, and monocyclic aryl or heteroaryl.

In a second aspect, there is provided a compound selected from any one of the following compounds, or a pharmaceutically acceptable salt thereof:

| Compound No. | Compound Structure | Compound Name |
|---|---|---|
| 1 | 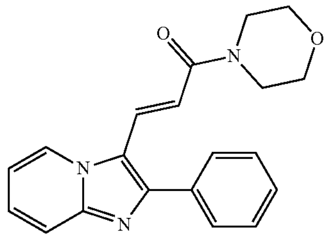 [SMILES: O=C(/C=C/c1c(-c2ccccc2)nc2ccccn12)N1CCOCC1] | (E)-1-morpholino-3-(2-phenylimidazo[1,2-a]pyridin-3-yl)prop-2-en-1-one |
| 2 | 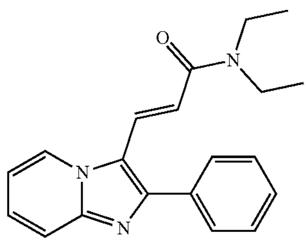 [SMILES: CCN(CC)C(=O)/C=C/c1c(-c2ccccc2)nc2ccccn12] | (E)-N,N-diethyl-3-(2-phenylimidazo[1,2-a]pyridin-3-yl)acrylamide |
| 3 | 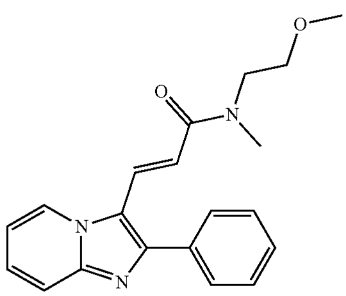 [SMILES: COCCN(C)C(=O)/C=C/c1c(-c2ccccc2)nc2ccccn12] | (E)-N-(2-methoxyethyl)-N-methyl-3-(2-phenylimidazo[1,2-a]pyridin-3-yl)acrylamide |
| 4 | 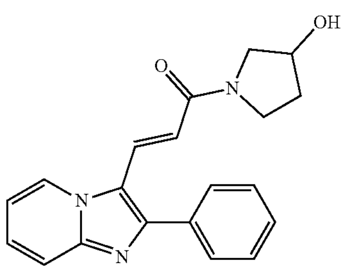 | (E)-1-(3-hydroxypyrrolidin-1-yl)-3-(2-phenylimidazo[1,2-a]pyridin-3-yl)prop-2-en-1-one |
| 5 | 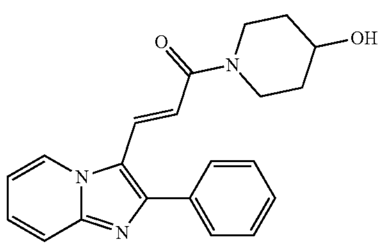 [SMILES: O=C(/C=C/c1c(-c2ccccc2)nc2ccccn12)N1CCC(O)CC1] | (E)-1-(4-hydroxypiperidin-1-yl)-3-(2-phenylimidazo[1,2-a]pyridin-3-yl)prop-2-en-1-one |

-continued

| Compound No. | Compound Structure | Compound Name |
|---|---|---|
| 6 | 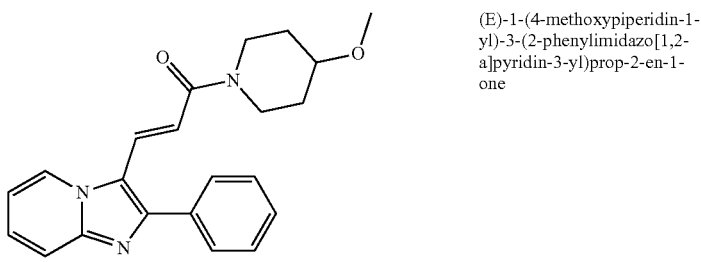 | (E)-1-(4-methoxypiperidin-1-yl)-3-(2-phenylimidazo[1,2-a]pyridin-3-yl)prop-2-en-1-one |
| 7 | 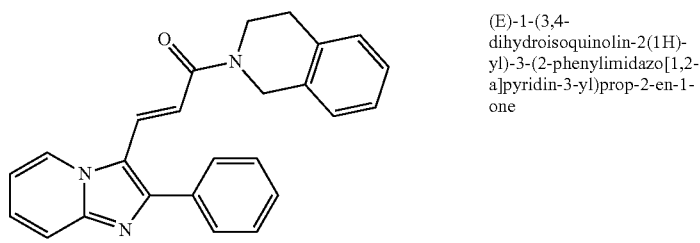 | (E)-1-(3,4-dihydroisoquinolin-2(1H)-yl)-3-(2-phenylimidazo[1,2-a]pyridin-3-yl)prop-2-en-1-one |
| 8 | 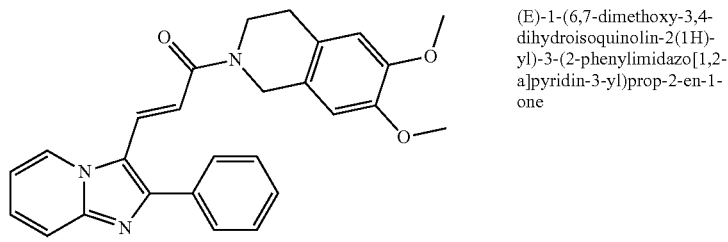 | (E)-1-(6,7-dimethoxy-3,4-dihydroisoquinolin-2(1H)-yl)-3-(2-phenylimidazo[1,2-a]pyridin-3-yl)prop-2-en-1-one |
| 9 | 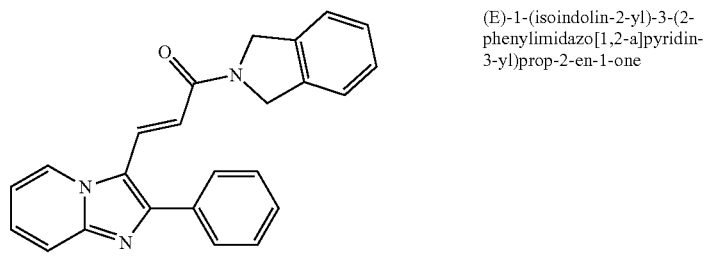 | (E)-1-(isoindolin-2-yl)-3-(2-phenylimidazo[1,2-a]pyridin-3-yl)prop-2-en-1-one |
| 10 | 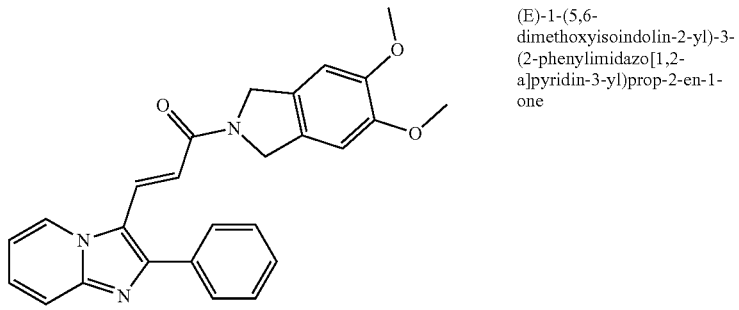 | (E)-1-(5,6-dimethoxyisoindolin-2-yl)-3-(2-phenylimidazo[1,2-a]pyridin-3-yl)prop-2-en-1-one |

| Compound No. | Compound Structure | Compound Name |
|---|---|---|
| 11 | 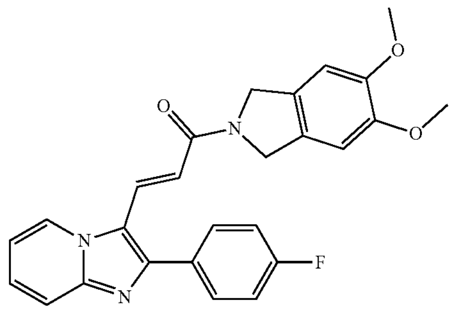 | (E)-1-(5,6-dimethoxyisoindolin-2-yl)-3-(2-(4-fluorophenyl)imidazo[1,2-a]pyridin-3-yl)prop-2-en-1-one |
| 12 | 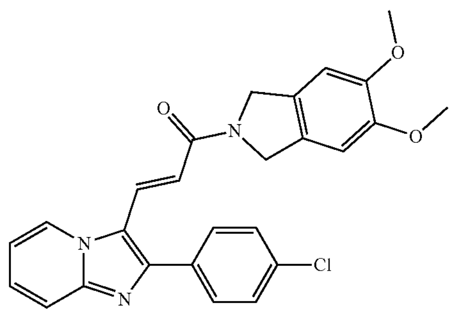 | (E)-3-(2-(4-chlorophenyl)imidazo[1,2-a]pyridin-3-yl)-1-(5,6-dimethoxyisoindolin-2-yl)prop-2-en-1-one |
| 13 | 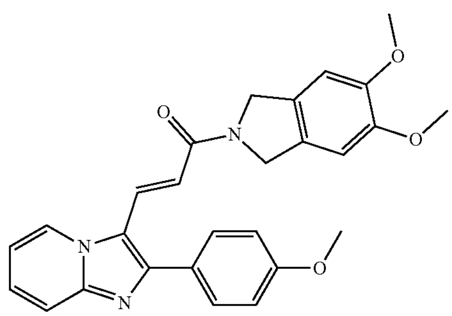 [SMILES: COc1ccc(-c2nc3ccccn3c2/C=C/C(=O)N2Cc3cc(OC)c(OC)cc3C2)cc1] | (E)-1-(5,6-dimethoxyisoindolin-2-yl)-3-(2-(4-methoxyphenyl)imidazo[1,2-a]pyridin-3-yl)prop-2-en-1-one |
| 14 | 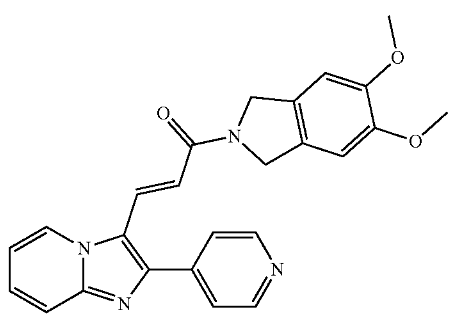 [SMILES: COc1cc2c(cc1OC)CN(C(=O)/C=C/c1c(-c3ccncc3)nc3ccccn13)C2] | (E)-1-(5,6-dimethoxyisoindolin-2-yl)-3-(2-(pyridin-4-yl)imidazo[1,2-a]pyridin-3-yl)prop-2-en-1-one |
| 15 | 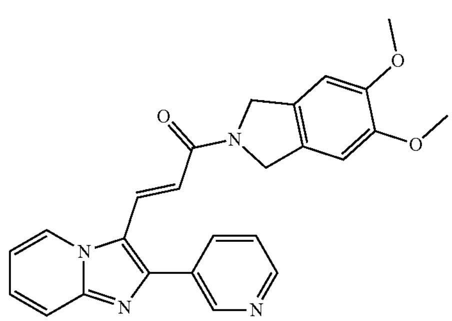 [SMILES: COc1cc2c(cc1OC)CN(C(=O)/C=C/c1c(-c3cccnc3)nc3ccccn13)C2] | (E)-1-(5,6-dimethoxyisoindolin-2-yl)-3-(2-(pyridin-3-yl)imidazo[1,2-a]pyridin-3-yl)prop-2-en-1-one |

-continued

| Compound No. | Compound Structure | Compound Name |
|---|---|---|
| 16 | 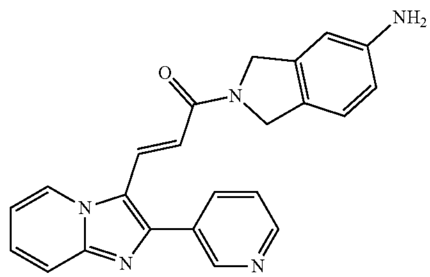 [SMILES: Nc1ccc2c(c1)CN(C(=O)/C=C/c1c(-c3cccnc3)nc3ccccn13)C2] | (E)-1-(5-aminoisoindolin-2-yl)-3-(2-(pyridin-3-yl)imidazo[1,2-a]pyridin-3-yl)prop-2-en-1-one |
| 17 | 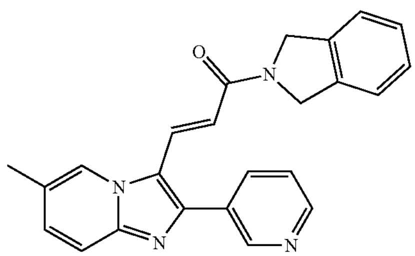 [SMILES: Cc1ccc2nc(-c3cccnc3)c(/C=C/C(=O)N3Cc4ccccc4C3)n2c1] | (E)-1-(isoindolin-2-yl)-3-(6-methyl-2-(pyridin-3-yl)imidazo[1,2-a]pyridin-3-yl)prop-2-en-1-one |
| 18 | 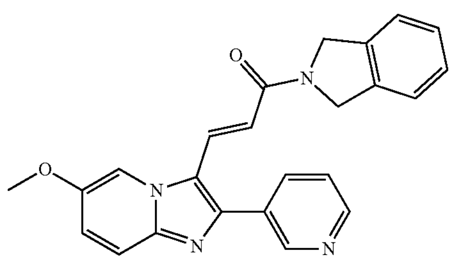 [SMILES: COc1ccc2nc(-c3cccnc3)c(/C=C/C(=O)N3Cc4ccccc4C3)n2c1] | (E)-1-(isoindolin-2-yl)-3-(6-methoxy-2-(pyridin-3-yl)imidazo[1,2-a]pyridin-3-yl)prop-2-en-1-one |
| 19 | 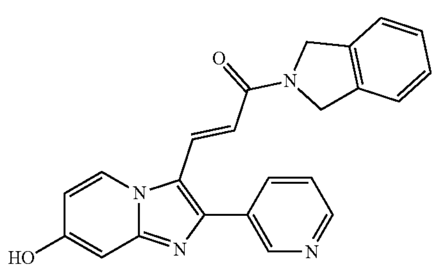 [SMILES: O=C(/C=C/c1c(-c2cccnc2)nc2cc(O)ccn12)N1Cc2ccccc2C1] | (E)-3-(7-hydroxy-2-(pyridin-3-yl)imidazo[1,2-a]pyridin-3-yl)-1-(isoindolin-2-yl)prop-2-en-1-one |
| 20 | 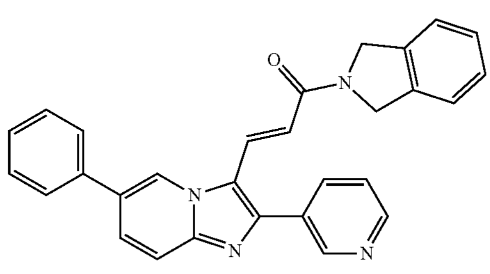 [SMILES: O=C(/C=C/c1c(-c2cccnc2)nc2ccc(-c3ccccc3)cn12)N1Cc2ccccc2C1] | (E)-1-(isoindolin-2-yl)-3-(6-phenyl-2-(pyridin-3-yl)imidazo[1,2-a]pyridin-3-yl)prop-2-en-1-one |

| Compound No. | Compound Structure | Compound Name |
|---|---|---|
| 21 | 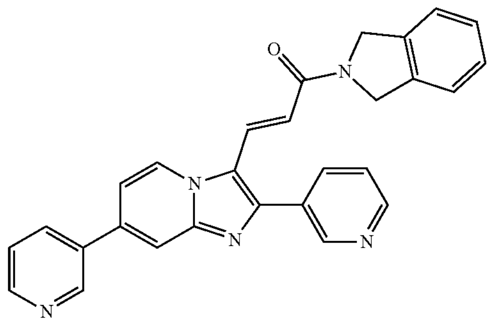 [SMILES: O=C(/C=C/c1c(-c2cccnc2)nc2cc(-c3cccnc3)ccn12)N1Cc2ccccc2C1] | (E)-3-(2,7-di(pyridin-3-yl)imidazo[1,2-a]pyridin-3-yl)-1-(isoindolin-2-yl)prop-2-en-1-one |
| 22 | 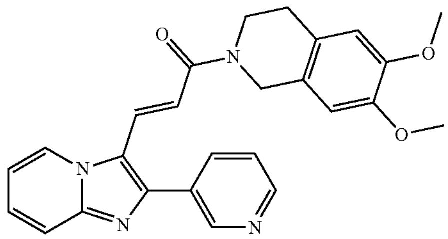 | (E)-1-(6,7-dimethoxy-3,4-dihydroisoquinolin-2(1H)-yl)-3-(2-(pyridin-3-yl)imidazo[1,2-a]pyridin-3-yl)prop-2-en-1-one |
| 23 | 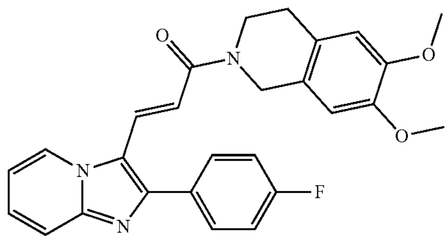 [SMILES: COc1cc2c(cc1OC)CN(C(=O)/C=C/c1c(-c3ccc(F)cc3)nc3ccccn13)CC2] | (E)-1-(6,7-dimethoxy-3,4-dihydroisoquinolin-2(1H)-yl)-3-(2-(4-fluorophenyl)imidazo[1,2-a]pyridin-3-yl)prop-2-en-1-one |
| 24 | 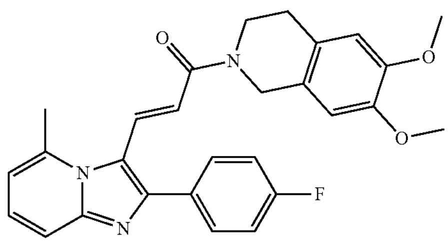 [SMILES: COc1cc2c(cc1OC)CN(C(=O)/C=C/c1c(-c3ccc(F)cc3)nc3cccc(C)n13)CC2] | (E)-1-(6,7-dimethoxy-3,4-dihydroisoquinolin-2(1H)-yl)-3-(2-(4-fluorophenyl)-5-methylimidazo[1,2-a]pyridin-3-yl)prop-2-en-1-one |
| 25 | 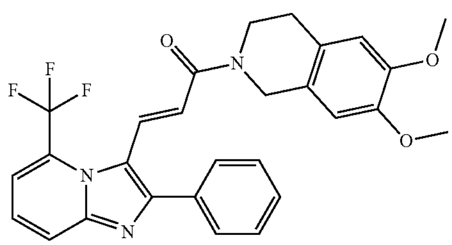 [SMILES: COc1cc2c(cc1OC)CN(C(=O)/C=C/c1c(-c3ccccc3)nc3cccc(C(F)(F)F)n13)CC2] | (E)-1-(6,7-dimethoxy-3,4-dihydroisoquinolin-2(1H)-yl)-3-(2-phenyl-5-(trifluoromethyl)imidazo[1,2-a]pyridin-3-yl)prop-2-en-1-one |
| 26 | 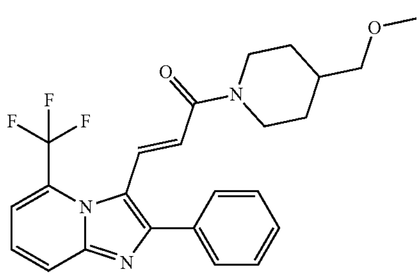 [SMILES: COCC1CCN(C(=O)/C=C/c2c(-c3ccccc3)nc3cccc(C(F)(F)F)n23)CC1] | (E)-1-(4-(methoxymethyl)piperidin-1-yl)-3-(2-phenyl-5-(trifluoromethyl)imidazo[1,2-a]pyridin-3-yl)prop-2-en-1-one |

-continued

| Compound No. | Compound Structure | Compound Name |
|---|---|---|
| 27 | 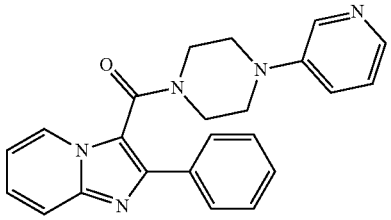 [SMILES: O=C(c1c(-c2ccccc2)nc2ccccn12)N1CCN(c2cccnc2)CC1] | (2-phenylimidazo[1,2-a]pyridin-3-yl)(4-(pyridin-3-yl)piperazin-1-yl)methanone |
| 28 | 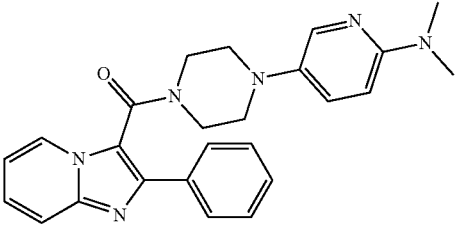 [SMILES: CN(C)c1ccc(N2CCN(C(=O)c3c(-c4ccccc4)nc4ccccn34)CC2)cn1] | (4-(6-(dimethylamino)pyridin-3-yl)piperazin-1-yl)(2-phenylimidazo[1,2-a]pyridin-3-yl)methanone |
| 29 | 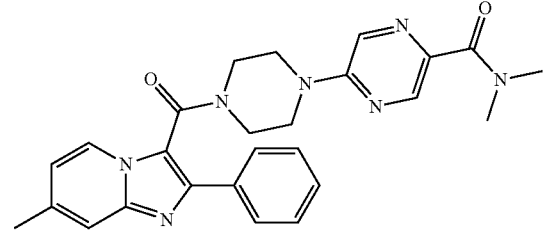 | N,N-dimethyl-5-(4-(7-methyl-2-phenylimidazo[1,2-a]pyridine-3-carbonyl)piperazin-1-yl)pyrazine-2-carboxamide |
| 30 | 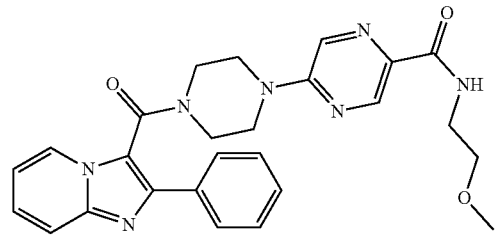 | N-(2-methoxyethyl)-5-(4-(2-phenylimidazo[1,2-a]pyridine-3-carbonyl)piperazin-1-yl)pyrazine-2-carboxamide |
| 31 | 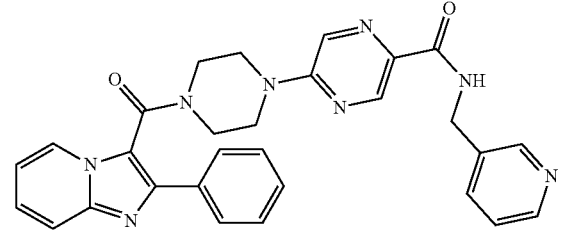 [SMILES: O=C(NCc1cccnc1)c1cnc(N2CCN(C(=O)c3c(-c4ccccc4)nc4ccccn34)CC2)cn1] | 5-(4-(2-phenylimidazo[1,2-a]pyridine-3-carbonyl)piperazin-1-yl)-N-(pyridin-3-ylmethyl)pyrazine-2-carboxamide |
| 32 | 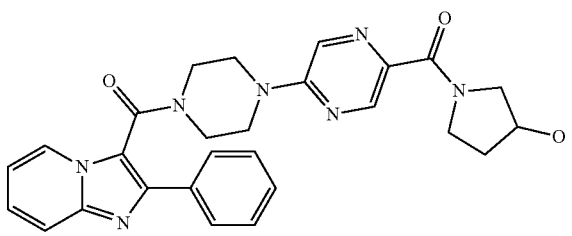 [SMILES: O=C(c1cnc(N2CCN(C(=O)c3c(-c4ccccc4)nc4ccccn34)CC2)cn1)N1CCC(O)C1] | (3-hydroxypyrrolidin-1-yl)(5-(4-(2-phenylimidazo[1,2-a]pyridine-3-carbonyl)piperazin-1-yl)pyrazin-2-yl)methanone |

-continued

| Compound No. | Compound Structure | Compound Name |
|---|---|---|
| 33 | 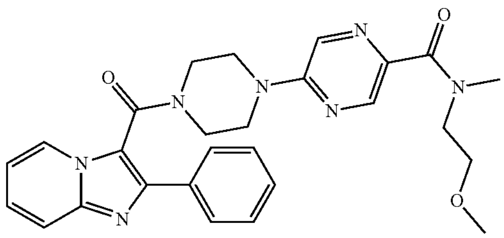 [SMILES: COCCN(C)C(=O)c1cnc(N2CCN(C(=O)c3c(-c4ccccc4)nc4ccccn34)CC2)cn1] | N-(2-methoxyethyl)-N-methyl-5-(4-(2-phenylimidazo[1,2-a]pyridine-3-carbonyl)piperazin-1-yl)pyrazine-2-carboxamide |
| 34 | 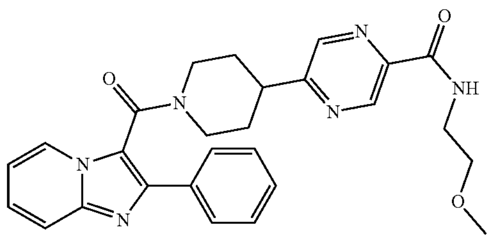 [SMILES: COCCNC(=O)c1cnc(C2CCN(C(=O)c3c(-c4ccccc4)nc4ccccn34)CC2)cn1] | N-(2-methoxyethyl)-5-(1-(2-phenylimidazo[1,2-a]pyridine-3-carbonyl)piperidin-4-yl)pyrazine-2-carboxamide |
| 35 | 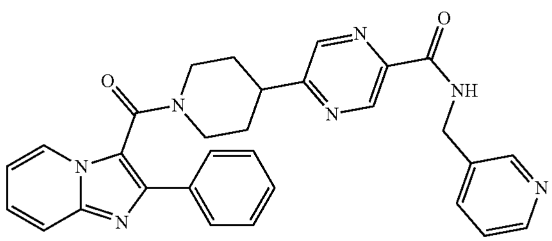 [SMILES: O=C(NCc1cccnc1)c1cnc(C2CCN(C(=O)c3c(-c4ccccc4)nc4ccccn34)CC2)cn1] | 5-(1-(2-phenylimidazo[1,2-a]pyridine-3-carbonyl)piperidin-4-yl)-N-(pyridin-3-ylmethyl)pyrazine-2-carboxamide |
| 36 | 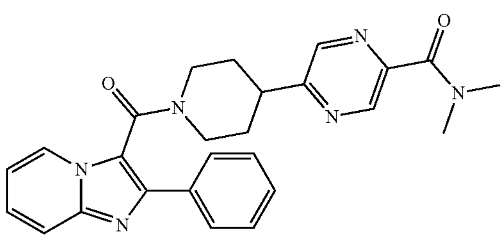 [SMILES: CN(C)C(=O)c1cnc(C2CCN(C(=O)c3c(-c4ccccc4)nc4ccccn34)CC2)cn1] | N,N-dimethyl-5-(1-(2-phenylimidazo[1,2-a]pyridine-3-carbonyl)piperidin-4-yl)pyrazine-2-carboxamide |
| 37 | 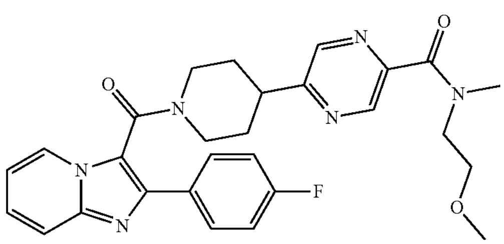 [SMILES: COCCN(C)C(=O)c1cnc(C2CCN(C(=O)c3c(-c4ccc(F)cc4)nc4ccccn34)CC2)cn1] | 5-(1-(2-(4-fluorophenyl)imidazo[1,2-a]pyridine-3-carbonyl)piperidin-4-yl)-N-(2-methoxyethyl)-N-methylpyrazine-2-carboxamide |
| 38 | 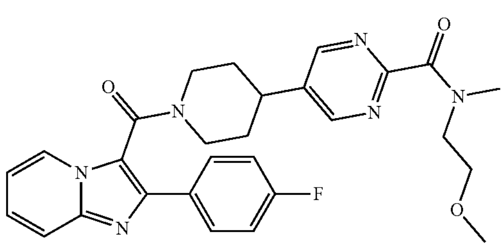 [SMILES: COCCN(C)C(=O)c1ncc(C2CCN(C(=O)c3c(-c4ccc(F)cc4)nc4ccccn34)CC2)cn1] | 5-(1-(2-(4-fluorophenyl)imidazo[1,2-a]pyridine-3-carbonyl)piperidin-4-yl)-N-(2-methoxyethyl)-N-methylpyrimidine-2-carboxamide |

-continued

| Compound No. | Compound Structure | Compound Name |
|---|---|---|
| 39 | 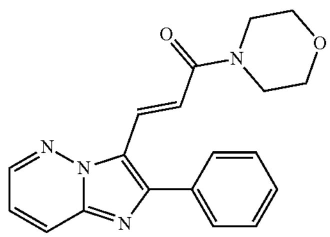 [SMILES: O=C(/C=C/c1c(-c2ccccc2)nc2cccnn12)N1CCOCC1] | (E)-1-morpholino-3-(2-phenylimidazo[1,2-b]pyridazin-3-yl)prop-2-en-1-one |
| 40 | 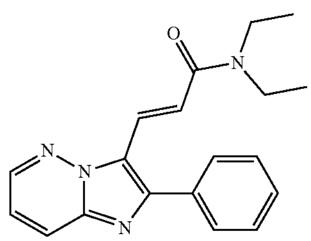 [SMILES: CCN(CC)C(=O)/C=C/c1c(-c2ccccc2)nc2cccnn12] | (E)-N,N-diethyl-3-(2-phenylimidazo[1,2-b]pyridazin-3-yl)acrylamide |
| 41 | 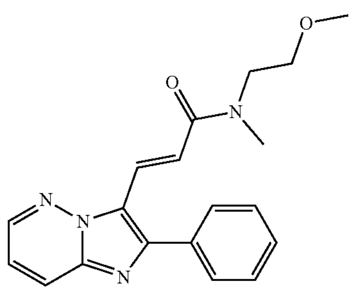 [SMILES: COCCN(C)C(=O)/C=C/c1c(-c2ccccc2)nc2cccnn12] | (E)-N-(2-methoxyethyl)-N-methyl-3-(2-phenylimidazo[1,2-b]pyridazin-3-yl)acrylamide |
| 42 | 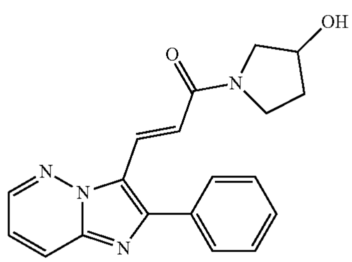 [SMILES: O=C(/C=C/c1c(-c2ccccc2)nc2cccnn12)N1CCC(O)C1] | (E)-1-(3-hydroxypyrrolidin-1-yl)-3-(2-phenylimidazo[1,2-b]pyridazin-3-yl)prop-2-en-1-one |
| 43 | 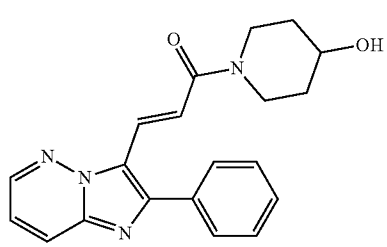 [SMILES: O=C(/C=C/c1c(-c2ccccc2)nc2cccnn12)N1CCC(O)CC1] | (E)-1-(4-hydroxypiperidin-1-yl)-3-(2-phenylimidazo[1,2-b]pyridazin-3-yl)prop-2-en-1-one |
| 44 | 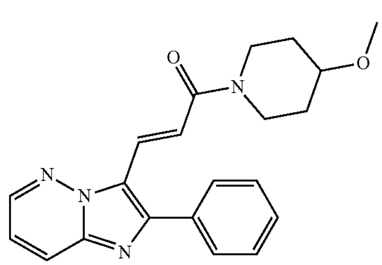 [SMILES: COC1CCN(C(=O)/C=C/c2c(-c3ccccc3)nc3cccnn23)CC1] | (E)-1-(4-methoxypiperidin-1-yl)-3-(2-phenylimidazo[1,2-b]pyridazin-3-yl)prop-2-en-1-one |

| Compound No. | Compound Structure | Compound Name |
|---|---|---|
| 45 | 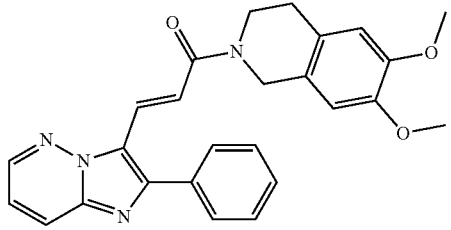 [SMILES: COc1cc2c(cc1OC)CN(C(=O)/C=C/c1c(-c3ccccc3)nc3cccnn13)CC2] | (E)-1-(6,7-dimethoxy-3,4-dihydroisoquinolin-2(1H)-yl)-3-(2-phenylimidazo[1,2-b]pyridazin-3-yl)prop-2-en-1-one |
| 46 | 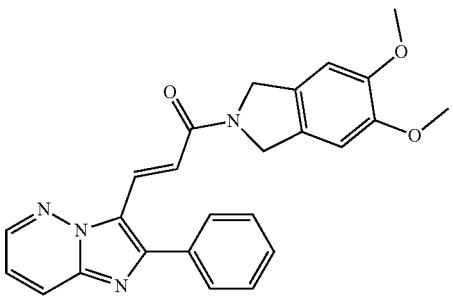 [SMILES: COc1cc2c(cc1OC)CN(C(=O)/C=C/c1c(-c3ccccc3)nc3cccnn13)C2] | (E)-1-(5,6-dimethoxyisoindolin-2-yl)-3-(2-phenylimidazo[1,2-b]pyridazin-3-yl)prop-2-en-1-one |
| 47 | 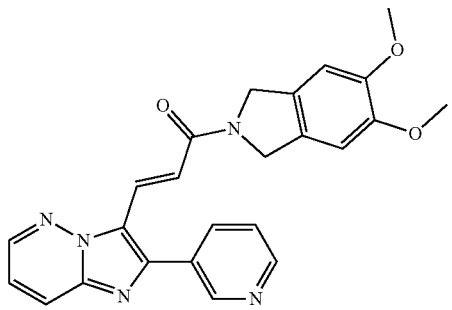 [SMILES: COc1cc2c(cc1OC)CN(C(=O)/C=C/c1c(-c3cccnc3)nc3cccnn13)C2] | (E)-1-(5,6-dimethoxyisoindolin-2-yl)-3-(2-(pyridin-3-yl)imidazo[1,2-b]pyridazin-3-yl)prop-2-en-1-one |
| 48 | 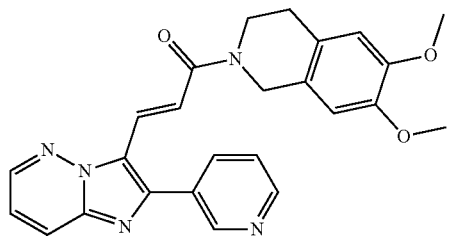 | (E)-1-(6,7-dimethoxy-3,4-dihydroisoquinolin-2(1H)-yl)-3-(2-(pyridin-3-yl)imidazo[1,2-b]pyridazin-3-yl)prop-2-en-1-one |
| 49 | 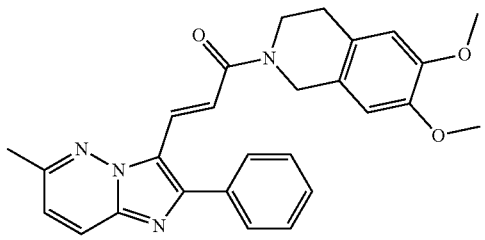 | (E)-1-(6,7-dimethoxy-3,4-dihydroisoquinolin-2(1H)-yl)-3-(6-methyl-2-phenylimidazo[1,2-b]pyridazin-3-yl)prop-2-en-1-one |

| Compound No. | Compound Structure | Compound Name |
|---|---|---|
| 50 | 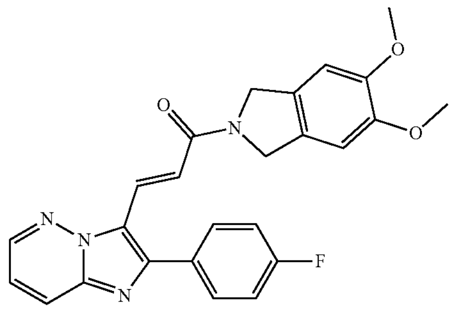 | (E)-1-(5,6-dimethoxyisoindolin-2-yl)-3-(2-(4-fluorophenyl)imidazo[1,2-b]pyridazin-3-yl)prop-2-en-1-one |
| 51 | 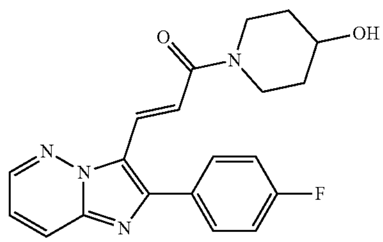 [SMILES: O=C(/C=C/c1c(-c2ccc(F)cc2)nc2cccnn12)N1CCC(O)CC1] | (E)-3-(2-(4-fluorophenyl)imidazo[1,2-b]pyridazin-3-yl)-1-(4-hydroxypiperidin-1-yl)prop-2-en-1-one |
| 52 | 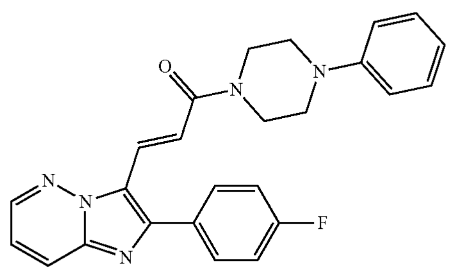 [SMILES: O=C(/C=C/c1c(-c2ccc(F)cc2)nc2cccnn12)N1CCN(c2ccccc2)CC1] | (E)-3-(2-(4-fluorophenyl)imidazo[1,2-b]pyridazin-3-yl)-1-(4-phenylpiperazin-1-yl)prop-2-en-1-one |
| 53 | 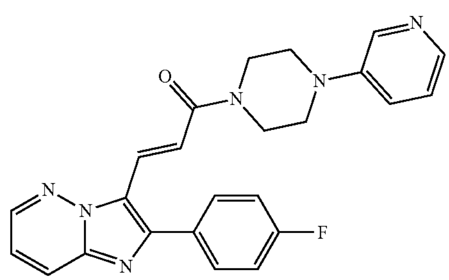 [SMILES: O=C(/C=C/c1c(-c2ccc(F)cc2)nc2cccnn12)N1CCN(c2cccnc2)CC1] | (E)-3-(2-(4-fluorophenyl)imidazo[1,2-b]pyridazin-3-yl)-1-(4-(pyridin-3-yl)piperazin-1-yl)prop-2-en-1-one |
| 54 | 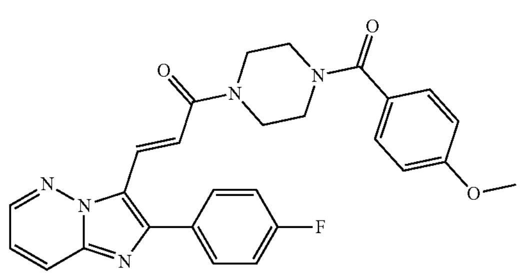 [SMILES: COc1ccc(C(=O)N2CCN(C(=O)/C=C/c3c(-c4ccc(F)cc4)nc4cccnn34)CC2)cc1] | (E)-3-(2-(4-fluorophenyl)imidazo[1,2-b]pyridazin-3-yl)-1-(4-(4-methoxybenzoyl)piperazin-1-yl)prop-2-en-1-one |

| Compound No. | Compound Structure | Compound Name |
|---|---|---|
| 55 | 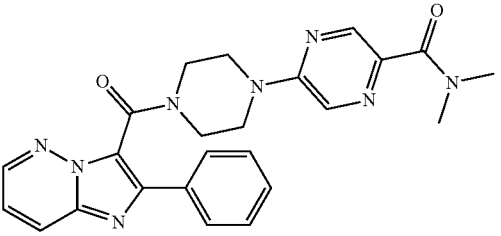 [SMILES: CN(C)C(=O)c1cnc(N2CCN(C(=O)c3c(-c4ccccc4)nc4cccnn34)CC2)cn1] | N,N-dimethyl-5-(4-(2-phenylimidazo[1,2-b]pyridazine-3-carbonyl)piperazin-1-yl)pyrazine-2-carboxamide |
| 56 | 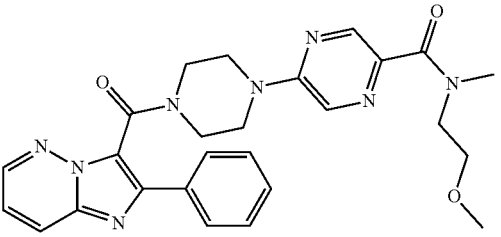 [SMILES: COCCN(C)C(=O)c1cnc(N2CCN(C(=O)c3c(-c4ccccc4)nc4cccnn34)CC2)cn1] | N-(2-methoxyethyl)-N-methyl-5-(4-(2-phenylimidazo[1,2-b]pyridazine-3-carbonyl)piperazin-1-yl)pyrazine-2-carboxamide |
| 57 | 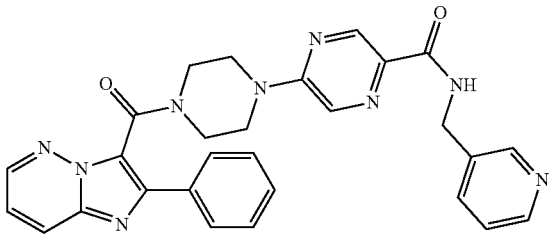 [SMILES: O=C(NCc1cccnc1)c1cnc(C2CCN(C(=O)c3c(-c4ccccc4)nc4cccnn34)CC2)cn1] | 5-(4-(2-phenylimidazo[1,2-b]pyridazine-3-carbonyl)piperazin-1-yl)-N-(pyridin-3-ylmethyl)pyrazine-2-carboxamide |
| 58 | 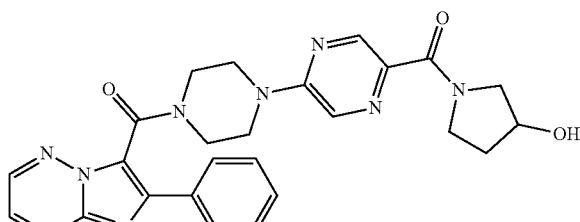 | (3-hydroxypyrrolidin-1-yl)(5-(4-(2-phenylimidazo[1,2-b]pyridazine-3-carbonyl)piperazin-1-yl)pyrazin-2-yl)methanone |
| 59 | 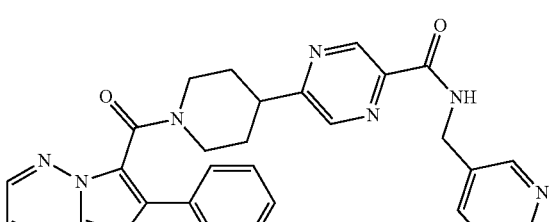 | 5-(1-(2-phenylimidazo[1,2-b]pyridazine-3-carbonyl)piperidin-4-yl)-N-(pyridin-3-ylmethyl)pyrazine-2-carboxamide |
| 60 | 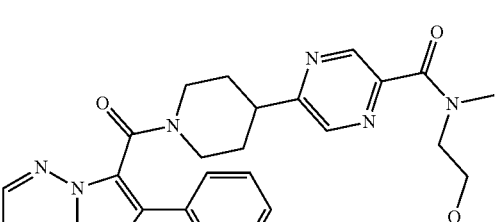 | N-(2-methoxyethyl)-N-methyl-5-(1-(2-phenylimidazo[1,2-b]pyridazine-3-carbonyl)piperidin-4-yl)pyrazine-2-carboxamide |

| Compound No. | Compound Structure | Compound Name |
|---|---|---|
| 61 | 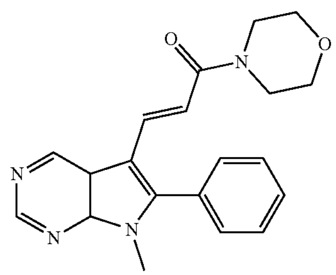 [SMILES: CN1C(c2ccccc2)=C(/C=C/C(=O)N2CCOCC2)C2C=NC=NC21] | (E)-3-(7-methyl-6-phenyl-4a,7a-dihydro-7H-pyrrolo[2,3-d]pyrimidin-5-yl)-1-morpholinoprop-2-en-1-one |
| 62 | 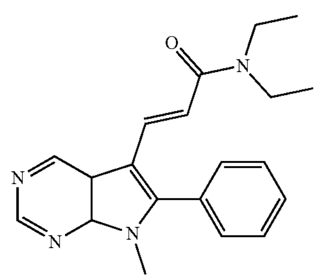 [SMILES: CCN(CC)C(=O)/C=C/C1=C(c2ccccc2)N(C)C2N=CN=CC12] | (E)-N,N-diethyl-3-(7-methyl-6-phenyl-4a,7a-dihydro-7H-pyrrolo[2,3-d]pyrimidin-5-yl)acrylamide |
| 63 | 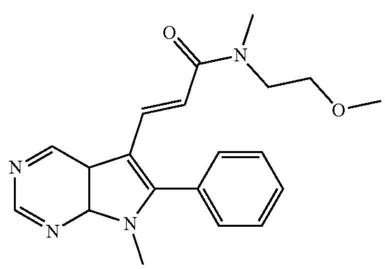 [SMILES: COCCN(C)C(=O)/C=C/C1=C(c2ccccc2)N(C)C2N=CN=CC12] | (E)-N-(2-methoxyethyl)-N-methyl-3-(7-methyl-6-phenyl-4a,7a-dihydro-7H-pyrrolo[2,3-d]pyrimidin-5-yl)acrylamide |
| 64 | 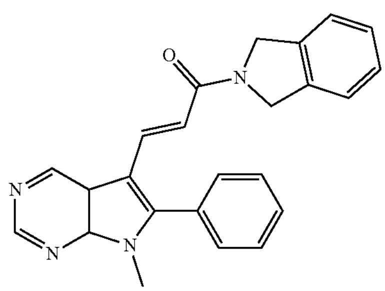 [SMILES: CN1C(c2ccccc2)=C(/C=C/C(=O)N2Cc3ccccc3C2)C2C=NC=NC21] | (E)-1-(isoindolin-2-yl)-3-(7-methyl-6-phenyl-4a,7a-dihydro-7H-pyrrolo[2,3-d]pyrimidin-5-yl)prop-2-en-1-one |
| 65 | 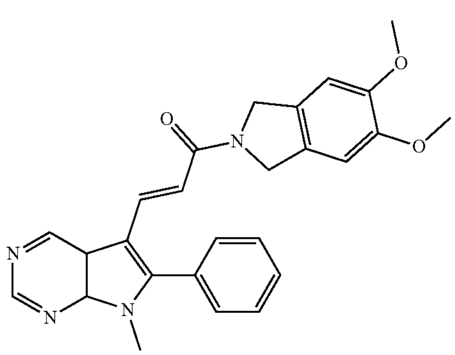 [SMILES: COc1cc2c(cc1OC)CN(C(=O)/C=C/C1=C(c3ccccc3)N(C)C3N=CN=CC13)C2] | (E)-1-(5,6-dimethoxyisoindolin-2-yl)-3-(7-methyl-6-phenyl-4a,7a-dihydro-7H-pyrrolo[2,3-d]pyrimidin-5-yl)prop-2-en-1-one |

-continued

| Compound No. | Compound Structure | Compound Name |
|---|---|---|
| 66 | 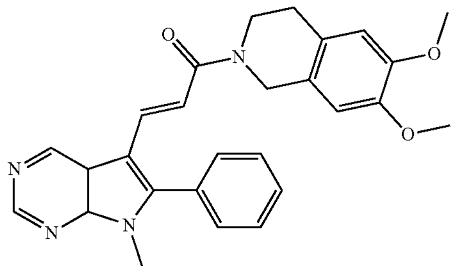 [SMILES: COc1cc2c(cc1OC)CN(C(=O)/C=C/C1=C(c3ccccc3)N(C)C3N=CN=CC13)CC2] | (E)-1-(6,7-dimethoxy-3,4-dihydroisoquinolin-2(1H)-yl)-3-(7-methyl-6-phenyl-4a,7a-dihydro-7H-pyrrolo[2,3-d]pyrimidin-5-yl)prop-2-en-1-one |
| 67 | 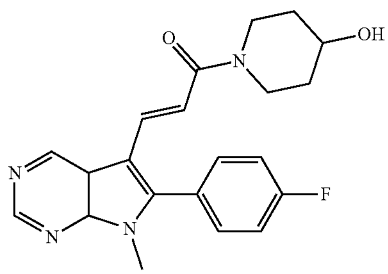 [SMILES: CN1C(c2ccc(F)cc2)=C(/C=C/C(=O)N2CCC(O)CC2)C2C=NC=NC21] | (E)-3-(6-(4-fluorophenyl)-7-methyl-4a,7a-dihydro-7H-pyrrolo[2,3-d]pyrimidin-5-yl)-1-(4-hydroxypiperidin-1-yl)prop-2-en-1-one |
| 68 | 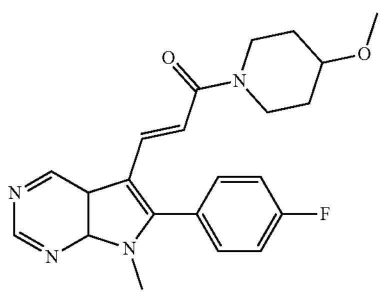 [SMILES: COC1CCN(C(=O)/C=C/C2=C(c3ccc(F)cc3)N(C)C3N=CN=CC23)CC1] | (E)-3-(6-(4-fluorophenyl)-7-methyl-4a,7a-dihydro-7H-pyrrolo[2,3-d]pyrimidin-5-yl)-1-(4-methoxypiperidin-1-yl)prop-2-en-1-one |
| 69 | 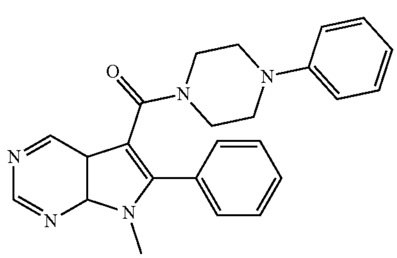 [SMILES: CN1C(c2ccccc2)=C(C(=O)N2CCN(c3ccccc3)CC2)C2C=NC=NC21] | (7-methyl-6-phenyl-4a,7a-dihydro-7H-pyrrolo[2,3-d]pyrimidin-5-yl)(4-phenylpiperazin-1-yl)methanone |
| 70 | 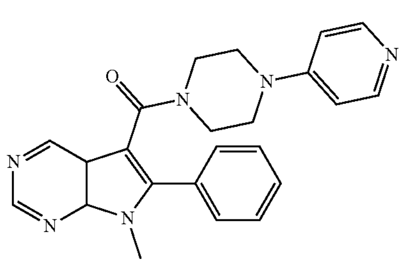 [SMILES: CN1C(c2ccccc2)=C(C(=O)N2CCN(c3ccncc3)CC2)C2C=NC=NC21] | (7-methyl-6-phenyl-4a,7a-dihydro-7H-pyrrolo[2,3-d]pyrimidin-5-yl)(4-(pyridin-4-yl)piperazin-1-yl)methanone |

-continued

| Compound No. | Compound Structure | Compound Name |
|---|---|---|
| 71 | 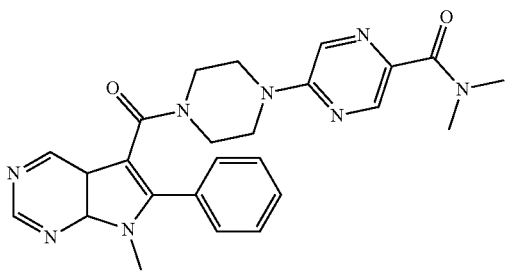 | N,N-dimethyl-5-(4-(7-methyl-6-phenyl-4a,7a-dihydro-7H-pyrrolo[2,3-d]pyrimidine-5-carbonyl)piperazin-1-yl)pyrazine-2-carboxamide |
| 72 | 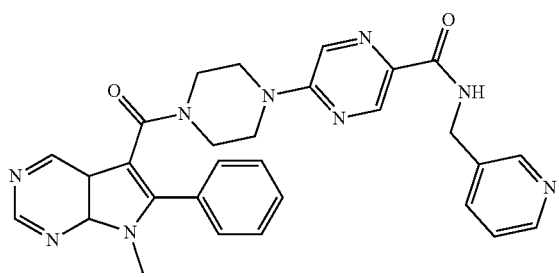 | 5-(4-(7-methyl-6-phenyl-4a,7a-dihydro-7H-pyrrolo[2,3-d]pyrimidine-5-carbonyl)piperazin-1-yl)-N-(pyridin-3-ylmethyl)pyrazine-2-carboxamide |
| 73 | 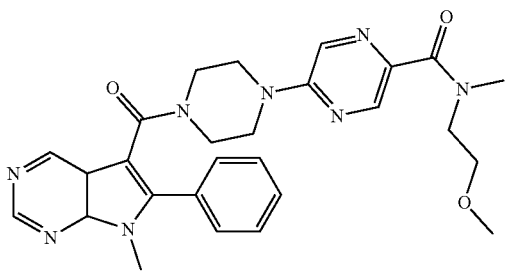 | N-(2-methoxyethyl)-N-methyl-5-(4-(7-methyl-6-phenyl-4a,7a-dihydro-7H-pyrrolo[2,3-d]pyrimidine-5-carbonyl)piperazin-1-yl)pyrazine-2-carboxamide |
| 74 | 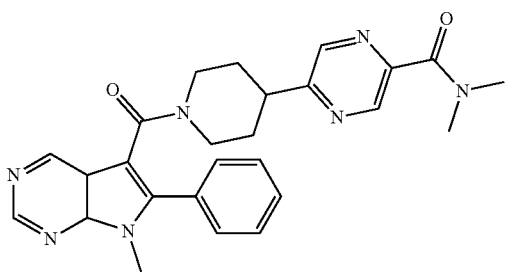 [SMILES: CN(C)C(=O)c1cnc(C2CCN(C(=O)C3=C(c4ccccc4)N(C)C4N=CN=CC34)CC2)cn1] | N,N-dimethyl-5-(1-(7-methyl-6-phenyl-4a,7a-dihydro-7H-pyrrolo[2,3-d]pyrimidine-5-carbonyl)piperidin-4-yl)pyrazine-2-carboxamide |
| 75 | 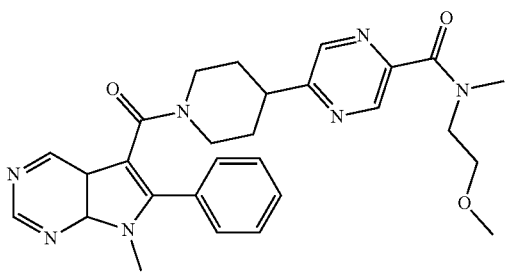 | N-(2-methoxyethyl)-N-methyl-5-(1-(7-methyl-6-phenyl-4a,7a-dihydro-7H-pyrrolo[2,3-d]pyrimidine-5-carbonyl)piperidin-4-yl)pyrazine-2-carboxamide |

-continued

| Compound No. | Compound Structure | Compound Name |
|---|---|---|
| 76 | 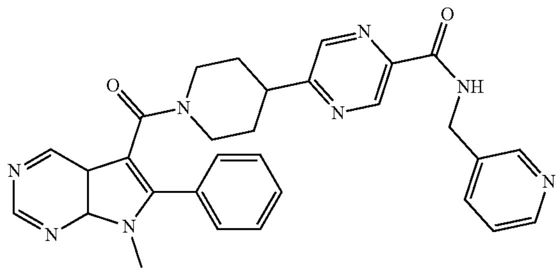 | 5-(1-(7-methyl-6-phenyl-4a,7a-dihydro-7H-pyrrolo[2,3-d]pyrimidine-5-carbonyl)piperidin-4-yl)-N-(pyridin-3-ylmethyl)pyrazine-2-carboxamide |

In a third aspect there is provided a pharmaceutical composition comprising a compound selected from Formula 1 or Formula 2, or a pharmaceutically acceptable salt thereof, as described herein, and a pharmaceutically acceptable excipient.

The composition or formulation may be useful for inhibiting cell proliferation, e.g., for treating cancer by suppressing cancer cell growth, and by blocking cancer supportive cells within the cancer microenvironment, thereby preventing cancer invasion and metastasis. The composition may include an effective amount of an inhibitor of Smad3 and a pharmaceutically acceptable excipient. The composition may be formulated for subcutaneous, intramuscular, intravenous, intraperitoneal, topical, or oral administration. For example, the composition may be in the form of a solution, a powder, a paste/cream, a tablet, or a capsule.

In a fourth aspect there is provided a method of treatment that comprises inhibiting proliferation of a cell, comprising the step of contacting the cell with an effective amount of an inhibitor of Smad3 selected from a compound of Formula 1 or Formula 2.

The method for inhibiting proliferation of a cell, includes but is not limited to inhibiting cancer cell proliferation, tumor growth, invasion, and metastasis. The method includes the step of contacting the cell with an effective amount of an inhibitor of Smad3 selected from a compound of Formula 1 or Formula 2, or any embodiments thereof as described herein. The cell may be a cancer cell, which may be within a human body. The cancer may be lung carcinoma or melanoma, including primary and metastatic cancers. Also targeted by the Smad3 inhibitor are various cells surrounding the cancer tissue or cancer stromal cells, i.e., cells in the cancer microenvironment of the primary or metastatic cancer in the human body, including vascular endothelial cells, fibroblasts, neutrophils, eosinophils, mast cells, T cells and subsets, B cells, macrophages, and NK cells within the cancer microenvironment. The targeted cell may be a metastatic cancer cell within the human body such as a cell in the lymph nodes, liver, lung, bone, kidney, brain, gastric, or colon tissues. The contacting step may involve subcutaneous, intramuscular, intravenous, intraperitoneal, topical, or oral administration. For example, the Smad3 inhibitor compound may be administered in the form of a solution, a powder, a paste/cream, a tablet, or a capsule.

In a fifth aspect there is provided a method for treating cancer by administration of an effective amount of a compound of Formula 1 or Formula 2, or composition thereof, according to any embodiment thereof as described herein, to a subject in need of treatment thereof.

The cancer may be lung carcinoma or melanoma, and may include primary and metastatic cancers. The metastatic cancer may be a cancer of the lymph nodes, liver, lung, bone, kidney, brain, gastric, liver or colon tissues.

In a sixth aspect, there is provided a compound of Formula 1 or Formula 2, or composition thereof, according to any embodiments thereof as described herein, for use in the treatment of cancer or for inhibiting proliferation of a cell.

In a seventh aspect there is provided a Smad3 inhibitor agent selected from a compound of Formula 1 or Formula 2, according to any embodiments thereof as described herein, for treating cancer or for inhibiting proliferation of a cell.

In an eighth aspect, there is provided a use of a compound of Formula 1 or Formula 2, or composition thereof, according to any embodiment thereof as described herein, for the treatment of cancer or for inhibiting proliferation of a cell.

In a ninth aspect, there is provided a use of a compound of Formula 1 or Formula 2, or composition thereof, according to any embodiment thereof as described herein, in the manufacture of a medicament for the treatment of cancer or for inhibiting proliferation of a cell.

In a tenth aspect, there is provided a process for preparing a compound of Formula 1 or Formula 2, according to any embodiment thereof as described herein, for example according to any one of Schemes 1 to 4 as described herein.

In an eleventh aspect, there is provided a method of treating or preventing cancer comprising administering a therapeutically effective amount of a compound according to the first or second aspects, or a pharmaceutically acceptable salt thereof, to a patient in need thereof.

The cancer may be selected from the group consisting of solid tumors and non-solid tumors.

The chemical compound may be administered at an amount of from 0.1 mg/Kg body weight to 2500 mg/Kg body weight. The chemical compound may be administered at an amount of from 0.1 mg/Kg body weight to 100 mg/Kg body weight.

The cancer maybe a solid tumor selected from the group consisting of lung cancer, colorectal cancer, gastric cancer, melanoma, pancreatic cancer, breast cancer, liver cancer and or prostate cancer.

The compound may be formulated for subcutaneous, intramuscular, intravenous, intraperitoneal, topical or oral administration.

In a twelfth aspect, the present invention provides compound according to the first or second aspect, for use in the treatment or prevention of cell proliferation of a cell in a subject.

The use for treating or preventing cancer in a subject.

The cancer may be lung cancer, colorectal cancer, gastric cancer, melanoma, pancreatic cancer, breast cancer, liver cancer or prostate cancer.

The compound may be formulated for subcutaneous, intramuscular, intravenous, intraperitoneal, topical or oral administration.

The compound may be administered in the form of a solution, a powder, a paste, a tablet or a capsule.

In a thirteenth aspect, the present invention provides a method of treating or preventing cancer comprising administering to a subject in need thereof (a) an effective amount of the composition according to the first or second aspect, and (b) an effective amount of at least one additional anti-cancer agent to provide a combination therapy having an enhanced therapeutic effect compared to the effect of said chemical composition and the at least one additional anti-cancer agent each administered alone.

The combination therapy has a synergistic therapeutic effect.

The cancer may be selected from the group consisting of solid tumors and non-solid tumors.

The chemical composition may be administered at an amount of from 0.1 mg/Kg body weight to 2500 mg/Kg body weight.

The chemical composition may be administered at an amount of from 0.1 mg/Kg body weight to 100 mg/Kg body weight.

The cancer may be a solid tumor selected from the group consisting of colorectal cancer, gastric cancer, melanoma, pancreatic cancer, liver cancer and prostate cancer.

The at least one additional anti-cancer agent may be a chemotherapeutic agent.

The chemotherapeutic agent may be selected from the group consisting of cyclophosphamide, chlorambucil, melphalan, mechlorethamine, ifosfamide, busulfan, lomustine, streptozocin, temozolomide, dacarbazine, cisplatin, carboplatin, oxaliplatin, procarbazine, uramustine, methotrxate, pemetrexed, fludarabine, cytarabine, fluorouracil, floxuridine, gemcitabine, capecitabine, vinblastine, vincristine, vinorelbine, etoposide, paclitaxel, docetaxel, doxorubicin, daunorubicin, epirubicin, idarubicin, mitoxantrone, bleomycin, mitomycin, hydroxyurea, topotecan, irinotecan, amsacrine, teniposide, erlotinib hydrochloride and combinations thereof.

The at least one additional anti-cancer agent may be a biologic drug. The biologic drug may be an antibody selected from the group consisting of cetuximab (Erbitux®, anti-CD24 antibody and bevacizumab (Avastin®).

The at least one additional anti-cancer agent may be halogenated xanthene or halogenated xanthene derivative. The halogenated xanthene may be Rose Bengal or a functional derivative of Rose Bengal.

The at least one additional anti-cancer agent may be Nivolumab (Opdivo®).

The at least one additional anti-cancer agent may be Pembrolizumab (Keytruda®).

The at least one additional anti-cancer agent is known to be effective in treating said cancer.

The cancer may be gastrointestinal cancer and the at least one additional anti-cancer agent is selected from the group consisting of oxaliplatin (Eloxatin®), fluorouracil (5-FU), anti-CD24 antibody, cetuximab (Erbitux®) and bevacizumab (Avastin®).

The cancer may be pancreatic cancer, and the at least one additional anti-cancer agent is selected from the group consisting of gemcitabine (Gemzar®) erlotinib hydrochlorides (Tarceva®) and humanized anti-CD24 monoclonal antibodies.

The cancer may be prostate cancer and the at least one additional anti-cancer agent is selected from the group consisting of cetuximab, (Erbitux®), bevacizumab (Avastin®) and humanized anti-CD24 monoclonal antibodies.

The chemical composition and the at least one additional anti-cancer agent may be administered simultaneously.

The chemical composition and the at least one additional anti-cancer agent may be administered in a single composition.

Each the chemical compound and the at least one additional anti-cancer agent may be administered in a separate composition.

The chemical composition and the at least one additional anti-cancer agent may be administered sequentially.

The chemical composition and the at least one additional anti-cancer agent may be administered concurrently.

The subject may be human.

In a fourteenth aspect, the present invention provides a ese of an effective amount of the chemical composition of the first or second aspects, for the preparation of a medicament for treating or preventing cancer to be administered in combination with at least one additional anti-cancer agent, thereby enhancing the anti-cancerous therapeutic effect compared to the effect of each of the medicament comprising the chemical composition and the at least one additional anti-cancer agent.

The medicament may consist of the chemical composition as the sole active agent.

The medicament comprising the chemical composition may be administered simultaneously with the at least one additional anti-cancer agent.

The medicament may comprise the chemical composition and the at least one additional anti-cancer agent that are to be administered sequentially.

The medicament may comprise the chemical composition and the at least one additional anti-cancer agent that are to be administered concurrently.

In a fifteenth aspect, the present invention provides for the use of an effective amount of the chemical composition of the first or second aspects, and an effective amount of at least one additional anti-cancer agent for the preparation of a medicament for treating cancer, wherein the collective amount of the chemical composition and the at least one additional anti-cancer agent provides for an enhanced therapeutic anti-cancer effect.

It will be appreciated that any one or more of the embodiments for one aspect may also provide one or more embodiments for another aspect as described above or herein.

BRIEF DESCRIPTION OF THE DRAWINGS

Preferred embodiments of the present disclosure will now be further described and illustrated, by way of example only, with reference to the accompanying drawings in which.

DETAILED DESCRIPTION

Figure 1:
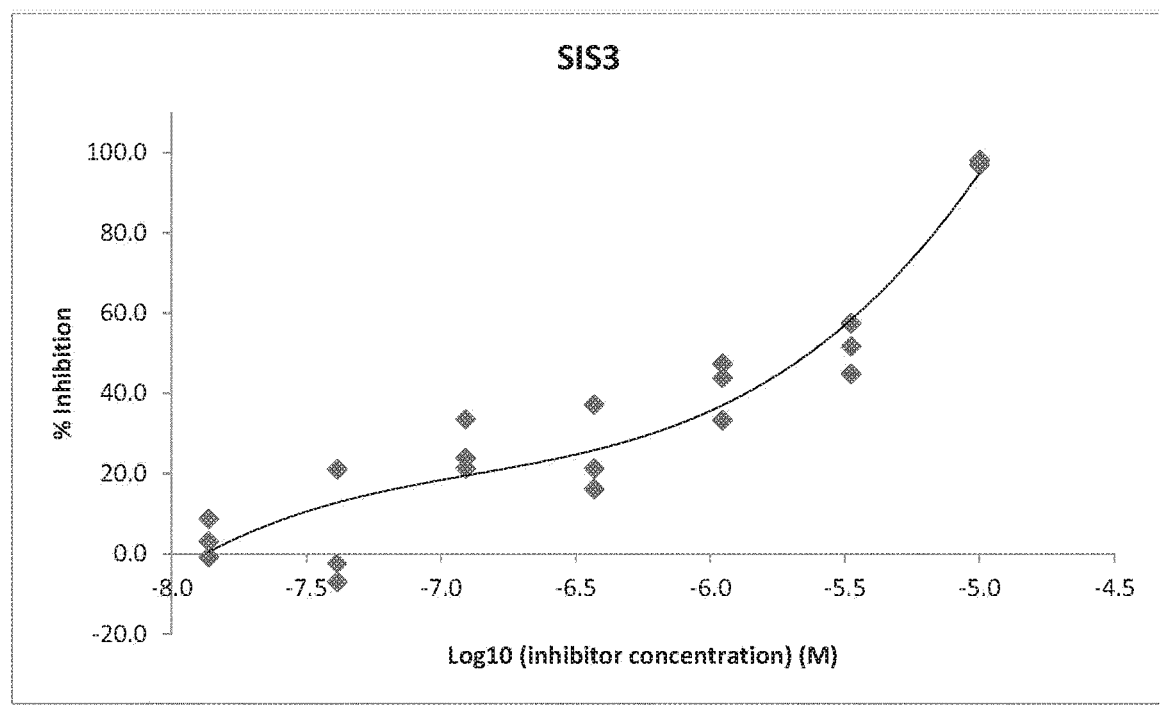
FIG. 1 shows the dose-response curve of compound SIS3, namely percentage inhibition versus concentration of compound SIS3.
Figure 2:
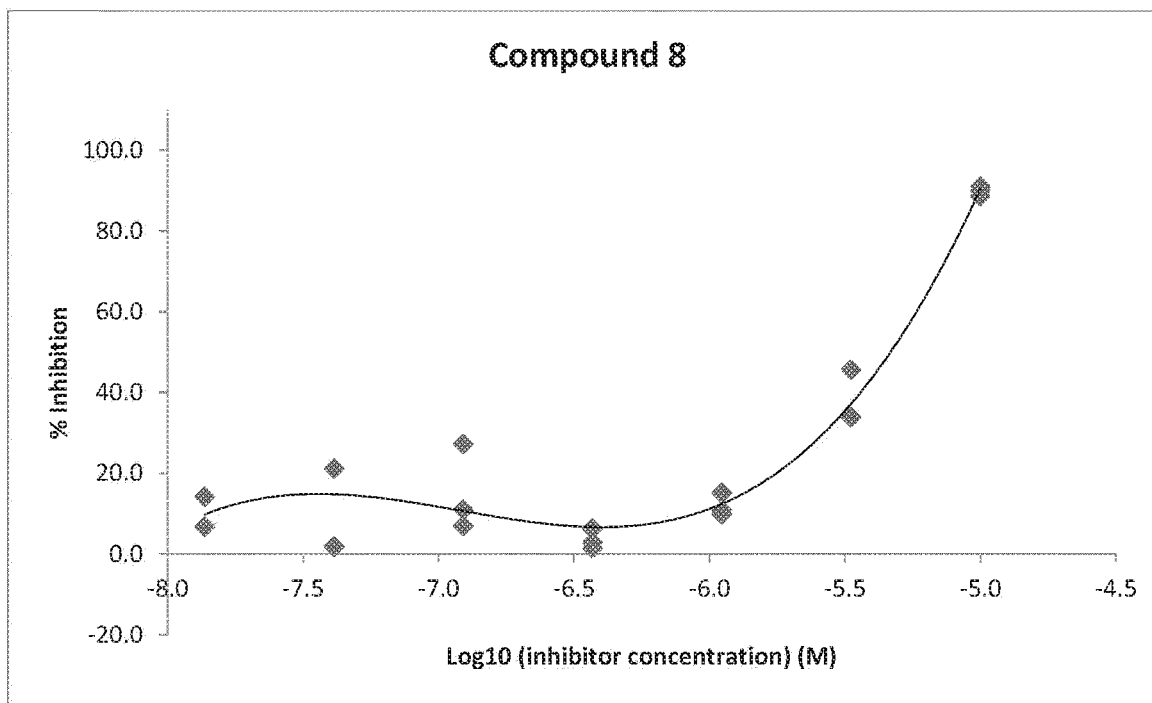
FIG. 2 shows the dose-response curve of compound 8, namely percentage inhibition versus concentration of compound 8.

The present disclosure describes the following various non-limiting embodiments, which relate to investigations undertaken to identify alternative compounds capable of inhibiting Smad3 and suitable for use in various compositions and formulations for treating cancer. It was surprisingly found that the compounds disclosed herein were capable of inhibiting Smad3 and are appropriately stable for use in compositions and formulations.

Specific Terms

The terms "carbocyclic" and "carbocyclyl" represent a monocyclic or polycyclic ring system wherein the ring atoms are all carbon atoms, e.g., of about 3 to about 20 carbon atoms, and which may be aromatic, non-aromatic, saturated, or unsaturated, and may be substituted and/or contain fused rings. Examples of such groups include aryl groups such as benzene, saturated groups such as cyclopentyl, or fully or partially hydrogenated phenyl, naphthyl and fluorenyl. It will be appreciated that the polycyclic ring system includes bicyclic and tricyclic ring systems.

"Heterocyclyl" or "heterocyclic" whether used alone, or in compound words such as heterocyclyloxy, represents a monocyclic or polycyclic ring system wherein the ring atoms are provided by at least two different elements, typically a combination of carbon and one or more of nitrogen, sulphur and oxygen, although may include other elements for ring atoms such as selenium, boron, phosphorus, bismuth and silicon, and wherein the ring system is about 3 to about 20 atoms, and which may be aromatic such as a "heteroaryl" group, non-aromatic, saturated, or unsaturated, and may be substituted and/or contain fused rings. For example, the heterocyclyl may be (i) an optionally substituted cycloalkyl or cycloalkenyl group, e.g., of about 3 to about 20 ring members, which may contain one or more heteroatoms such as nitrogen, oxygen, or sulfur (examples include pyrrolidinyl, morpholino, thiomorpholino, or fully or partially hydrogenated thienyl, furyl, pyrrolyl, thiazolyl, oxazolyl, oxazinyl, thiazinyl, pyridyl and azepinyl); (ii) an optionally substituted partially saturated monocyclic or polycyclic ring system in which an aryl (or heteroaryl) ring and a heterocyclic group are fused together to form a cyclic structure (examples include chromanyl, dihydrobenzofuryl and indolinyl); or (iii) an optionally substituted fully or partially saturated polycyclic fused ring system that has one or more bridges (examples include quinuclidinyl and dihydro-1,4-epoxynaphthyl). It will be appreciated that the polycyclic ring system includes bicyclic and tricyclic ring systems.

As will be understood, an "aromatic" group means a cyclic group having 4m+2 π electrons, where m is an integer equal to or greater than 1. As used herein, "aromatic" is used interchangeably with "aryl" to refer to an aromatic group, regardless of the valency of aromatic group.

"Aryl" whether used alone, or in compound words such as arylalkyl, aryloxy or arylthio, represents: (i) an optionally substituted mono- or polycyclic aromatic carbocyclic moiety, e.g., of about 6 to about 20 carbon atoms, such as phenyl, naphthyl or fluorenyl; or, (ii) an optionally substituted partially saturated polycyclic carbocyclic aromatic ring system in which an aryl and a cycloalkyl or cycloalkenyl group are fused together to form a cyclic structure such as a tetrahydronaphthyl, indenyl, indanyl or fluorene ring. It will be appreciated that the polycyclic ring system includes bicyclic and tricyclic ring systems.

A "hetaryl", "heteroaryl" or heteroaromatic group, is an aromatic group or ring containing one or more heteroatoms, such as N, O, S, Se, Si or P. As used herein, "heteroaromatic" is used interchangeably with "hetaryl" or "heteroaryl", and a heteroaryl group refers to monovalent aromatic groups, bivalent aromatic groups and higher multivalency aromatic groups containing one or more heteroatoms. For example, "heteroaryl" whether used alone, or in compound words such as heteroaryloxy represents: (i) an optionally substituted mono- or polycyclic aromatic organic moiety, e.g., of about 5 to about 20 ring members in which one or more of the ring members is/are element(s) other than carbon, for example nitrogen, oxygen, sulfur or silicon; the heteroatom(s) interrupting a carbocyclic ring structure and having a sufficient number of delocalized π electrons to provide aromatic character, provided that the rings do not contain adjacent oxygen and/or sulfur atoms. Typical 6-membered heteroaryl groups are pyrazinyl, pyridazinyl, pyrazolyl, pyridyl and pyrimidinyl. All regioisomers are contemplated, e.g., 2-pyridyl, 3-pyridyl and 4-pyridyl. Typical 5-membered heteroaryl rings are furyl, imidazolyl, oxazolyl, isoxazolyl, isothiazolyl, oxadiazolyl, pyrrolyl, 1,3,4-thiadiazolyl, thiazolyl, thienyl, triazolyl, and silole. All regioisomers are contemplated, e.g., 2-thienyl and 3-thienyl. Bicyclic groups typically are benzo-fused ring systems derived from the heteroaryl groups named above, e.g., benzofuryl, benzimidazolyl, benzthiazolyl, indolyl, indolizinyl, isoquinolyl, quinazolinyl, quinolyl and benzothienyl; or, (ii) an optionally substituted partially saturated polycyclic heteroaryl ring system in which a heteroaryl and a cycloalkyl or cycloalkenyl group are fused together to form a cyclic structure such as a tetrahydroquinolyl or pyrindinyl ring. It will be appreciated that the polycyclic ring system includes bicyclic and tricyclic ring systems.

The term "optionally fused" means that a group is either fused by another ring system or unfused, and "fused" refers to one or more rings that share at least one common ring atom with one or more other rings. The fusing may be provided a single common ring atom, for example a spiro compound. The fusing may be provided by at least two common atoms. Fusing may be provided by one or more carbocyclic, heterocyclic, aryl or hetaryl rings, as defined herein, or be provided by substituents of rings being joined together to form a further ring system. The fused ring may have between 5 and 10 ring atoms in size, for example a 5, 6 or 7 membered ring. The fused ring may be fused to one or more other rings, and may for example contain 1 to 4 rings.

The term "optionally substituted" means that a functional group is either substituted or unsubstituted, at any available position. Substitution can be with one or more functional groups selected from, e.g., alkyl, alkenyl, alkynyl, cycloalkyl, cycloalkenyl, aryl, heterocyclyl, heteroaryl, formyl, alkanoyl, cycloalkanoyl, aroyl, heteroaroyl, carboxyl, alkoxycarbonyl, cycloalkyloxycarbonyl, aryloxycarbonyl, heterocyclyloxycarbonyl, heteroaryloxycarbonyl, alkylaminocarbonyl, cycloalkylaminocarbonyl, arylaminocarbonyl, heterocyclylaminocarbonyl, heteroarylaminocarbonyl, cyano, alkoxy, cycloalkoxy, aryloxy, heterocyclyloxy, heteroaryloxy, alkanoate, cycloalkanoate, aryloate, heterocyclyloate, heteroaryloate, alkylcarbonylamino, cycloalkylcarbonylamino, arylcarbonylamino, heterocyclylcarbonylamino, heteroarylcarbonylamino, nitro, alkylthio, cycloalkylthio, arylthio, heterocyclylthio, heteroarylthio, alkylsulfonyl, cycloalkylsulfonyl, arylsulfonyl, heterocyclylsulfonyl, heteroarylsulfonyl, hydroxyl, halo, haloalkyl, haloaryl, haloheterocyclyl, haloheteroaryl, haloalkoxy, haloalkylsulfonyl, silylalkyl, alkenylsilylalkyl, and alkynylsilylalkyl. It will be appreciated that other groups not specifically described may also be used.

The term "halo" or "halogen" whether employed alone or in compound words such as haloalkyl, haloalkoxy or haloalkylsulfonyl, represents fluorine, chlorine, bromine or iodine. Further, when used in compound words such as haloalkyl, haloalkoxy or haloalkylsulfonyl, the alkyl may be partially halogenated or fully substituted with halogen atoms which may be independently the same or different.

Examples of haloalkyl include, without limitation, —$CH_2CH_2F$, —$CF_2CF_3$ and —$CH_2CHFCl$. Examples of haloalkoxy include, without limitation, —$OCHF_2$, —$OCF_3$, —$OCH_2CCl_3$, —$OCH_2CF_3$ and —$OCH_2CH_2CF_3$. Examples of haloalkylsulfonyl include, without limitation, —$SO_2CF_3$, —$SO_2CCl_3$, —$SO_2CH_2CF_3$ and —$SO_2CF_2CF_3$.

"Alkyl" whether used alone, or in compound words such as alkoxy, alkylthio, alkylamino, dialkylamino or haloalkyl, represents straight or branched chain hydrocarbons ranging in size from one to about 20 carbon atoms, or more. Thus alkyl moieties include, unless explicitly limited to smaller groups, moieties ranging in size, for example, from one to about 6 carbon atoms or greater, such as, methyl, ethyl, n-propyl, iso-propyl and/or butyl, pentyl, hexyl, and higher isomers, including, e.g., those straight or branched chain hydrocarbons ranging in size from about 6 to about 20 carbon atoms, or greater.

"Alkenyl" whether used alone, or in compound words such as alkenyloxy or haloalkenyl, represents straight or branched chain hydrocarbons containing at least one carbon-carbon double bond, including, unless explicitly limited to smaller groups, moieties ranging in size from two to about 6 carbon atoms or greater, such as, methylene, ethylene, 1-propenyl, 2-propenyl, and/or butenyl, pentenyl, hexenyl, and higher isomers, including, e.g., those straight or branched chain hydrocarbons ranging in size, for example, from about 6 to about 20 carbon atoms, or greater.

"Alkynyl" whether used alone, or in compound words such as alkynyloxy, represents straight or branched chain hydrocarbons containing at least one carbon-carbon triple bond, including, unless explicitly limited to smaller groups, moieties ranging in size from, e.g., two to about 6 carbon atoms or greater, such as, ethynyl, 1-propynyl, 2-propynyl, and/or butynyl, pentynyl, hexynyl, and higher isomers, including, e.g., those straight or branched chain hydrocarbons ranging in size from, e.g., about 6 to about 20 carbon atoms, or greater.

"Cycloalkyl" represents a mono- or polycarbocyclic ring system of varying sizes, e.g., from about 3 to about 20 carbon atoms, e.g., cyclopropyl, cyclobutyl, cyclopentyl, cyclohexyl or cycloheptyl. The term cycloalkyloxy represents the same groups linked through an oxygen atom such as cyclopentyloxy and cyclohexyloxy. The term cycloalkylthio represents the same groups linked through a sulfur atom such as cyclopentylthio and cyclohexylthio.

"Cycloalkenyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

"Cycloalkynyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

"Formyl" represents a —CHO moiety.

"Alkanoyl" represents a —C(=O)-alkyl group in which the alkyl group is as defined supra. In a particular embodiment, an alkanoyl ranges in size from about $C_2$-$C_{20}$. One example is acyl.

"Aroyl" represents a —C(=O)-aryl group in which the aryl group is as defined supra. In a particular embodiment, an aroyl ranges in size from about $C_7$-$C_{20}$. Examples include benzoyl and 1-naphthoyl and 2-naphthoyl.

"Heterocycloyl" represents a —C(=O)-heterocyclyl group in which the heterocylic group is as defined supra. In a particular embodiment, an heterocycloyl ranges in size from about $C_4$-$C_{20}$.

"Heteroaroyl" represents a —C(=O)-heteroaryl group in which the heteroaryl group is as defined supra. In a particular embodiment, a heteroaroyl ranges in size from about $C_6$-$C_{20}$. An example is pyridylcarbonyl.

"Carboxyl" represents a —$CO_2H$ moiety.

"Oxycarbonyl" represents a carboxylic acid ester group —$CO_2R$ which is linked to the rest of the molecule through a carbon atom.

"Alkoxycarbonyl" represents an —$CO_2$-alkyl group in which the alkyl group is as defined supra. In a particular embodiment, an alkoxycarbonyl ranges in size from about $C_2$-$C_{20}$. Examples include methoxycarbonyl and ethoxycarbonyl.

"Aryloxycarbonyl" represents an —$CO_2$-aryl group in which the aryl group is as defined supra. Examples include phenoxycarbonyl and naphthoxycarbonyl.

"Heterocyclyloxycarbonyl" represents a —$CO_2$-heterocyclyl group in which the heterocyclic group is as defined supra.

"Heteroaryloxycarbonyl" represents a —CO-heteroaryl group in which the heteroaryl group is as defined supra.

"Aminocarbonyl" represents a carboxylic acid amide group —C(=O)NHR or —C(=O)$NR_2$ which is linked to the rest of the molecule through a carbon atom.

"Alkylaminocarbonyl" represents a —C(=O)NHR or —C(=O)$NR_2$ group in which R is an alkyl group as defined supra.

"Arylaminocarbonyl" represents a —C(=O)NHR or —C(=O)$NR_2$ group in which R is an aryl group as defined supra.

"Heterocyclylaminocarbonyl" represents a —C(=O)NHR or —C(=O)$NR_2$ group in which R is a heterocyclic group as defined supra. In certain embodiments, $NR_2$ is a heterocyclic ring, which is optionally substituted.

"Heteroarylaminocarbonyl" represents a —C(=O)NHR or —C(=O)$NR_2$ group in which R is a heteroaryl group as defined supra. In certain embodiments, $NR_2$ is a heteroaryl ring, which is optionally substituted.

"Cyano" represents a —CN moiety.

"Hydroxyl" represents a —OH moiety.

"Alkoxy" represents an —O-alkyl group in which the alkyl group is as defined supra. Examples include methoxy, ethoxy, n-propoxy, iso-propoxy, and the different butoxy, pentoxy, hexyloxy and higher isomers.

"Aryloxy" represents an —O-aryl group in which the aryl group is as defined supra. Examples include, without limitation, phenoxy and naphthoxy.

"Alkenyloxy" represents an —O-alkenyl group in which the alkenyl group is as defined supra. An example is allyloxy.

"Heterocyclyloxy" represents an —O-heterocyclyl group in which the heterocyclic group is as defined supra.

"Heteroaryloxy" represents an —O-heteroaryl group in which the heteroaryl group is as defined supra. An example is pyridyloxy.

"Alkanoate" represents an —OC(=O)—R group in which R is an alkyl group as defined supra.

"Aryloate" represents a —OC(=O)—R group in which R is an aryl group as defined supra.

"Heterocyclyloate" represents an —OC(=O)—R group in which R is a heterocyclic group as defined supra.

"Heteroaryloate" represents an —OC(=O)—R group in which P is a heteroaryl group as defined supra.

"Amino" represents an —NH$_2$ moiety.

"Alkylamino" represents an —NHR or —NR$_2$ group in which R is an alkyl group as defined supra. Examples include, without limitation, methylamino, ethylamino, n-propylamino, isopropylamino, and the different butylamino, pentylamino, hexylamino and higher isomers.

"Arylamino" represents an —NHR or —NR$_2$ group in which R is an aryl group as defined supra. An example is phenylamino.

"Heterocyclylamino" represents an —NHR or —NR$_2$ group in which R is a heterocyclic group as defined supra. In certain embodiments, NR$_2$ is a heterocyclic ring, which is optionally substituted.

"Heteroarylamino" represents a —NHR or —NR$_2$ group in which R is a heteroaryl group as defined supra. In certain embodiments, NR$_2$ is a heteroaryl ring, which is optionally substituted.

"Carbonylamino" represents a carboxylic acid amide group —NHC(=O)R that is linked to the rest of the molecule through a nitrogen atom.

"Alkylcarbonylamino" represents a —NHC(=O)R group in which R is an alkyl group as defined supra.

"Arylcarbonylamino" represents an —NHC(=O)R group in which R is an aryl group as defined supra.

"Heterocyclylcarbonylamino" represents an —NHC(=O)R group in which R is a heterocyclic group as defined supra.

"Heteroarylcarbonylamino" represents an —NHC(=O)R group in which R is a heteroaryl group as defined supra.

"Nitro" represents a —NO$_2$ moiety.

"Alkylthio" represents an —S-alkyl group in which the alkyl group is as defined supra. Examples include, without limitation, methylthio, ethylthio, n-propylthio, iso propylthio, and the different butylthio, pentylthio, hexylthio and higher isomers.

"Arylthio" represents an —S-aryl group in which the aryl group is as defined supra. Examples include phenylthio and naphthylthio.

"Heterocyclylthio" represents an —S-heterocyclyl group in which the heterocyclic group is as defined supra.

"Heteroarylthio" represents an —S-heteroaryl group in which the heteroaryl group is as defined supra.

"Sulfonyl" represents an —SO$_2$R group that is linked to the rest of the molecule through a sulfur atom.

"Alkylsulfonyl" represents an —SO$_2$-alkyl group in which the alkyl group is as defined supra.

"Arylsulfonyl" represents an —SO$_2$-aryl group in which the aryl group is as defined supra.

"Heterocyclylsulfonyl" represents an —SO$_2$-heterocyclyl group in which the heterocyclic group is as defined supra.

"Heteoarylsulfonyl" presents an —SO$_2$-heteroaryl group in which the heteroaryl group is as defined supra.

"Aldehyde" represents a —C(=O)H group.

"Alkanal" represents an alkyl-(C=O)H group in which the alkyl group is as defined supra.

"Alkylsilyl" presents an alkyl group that is linked to the rest of the molecule through the silicon atom, which may be substituted with up to three independently selected alkyl groups in which each alkyl group is as defined supra.

"Alkenylsilyl" presents an alkenyl group that is linked to the rest of the molecule through the silicon atom, which may be substituted with up to three independently selected alkenyl groups in which each alkenyl group is as defined supra.

"Alkynylsilyl" presents an alkynyl group that is linked to the rest of the molecule through the silicon atom, which may be substituted with up to three independently selected alkynyl groups in which each alkenyl group is as defined supra.

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

The term "C$_{1-10}$alkyl," as used herein refers to a straight chain or branched, saturated or unsaturated hydrocarbon having from 1 to 10 carbon atoms. Representative "C$_{1-10}$alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched C$_1$-C$_8$ alkyls include, but are not limited to, -isopropyl, -sec-butyl, -isobutyl, -tert-butyl, -isopentyl, 2-methylbutyl, unsaturated C$_1$-C$_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A C$_1$-C$_8$ alkyl group can be unsubstituted or substituted with one or more groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —C$_1$-C$_8$ alkyl and aryl.

A "C$_{3-12}$carbocyclyl" is a 3-, 4-, 5-, 6-, 7- or 8-membered saturated or unsaturated non-aromatic carbocyclic ring. Representative C$_{3-12}$carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5- cycloheptatrienyl, -cyclooctyl, and -cyclooctadienyl. A $C_3$-$C_8$ carbocycle group can be unsubstituted or substituted with one or more groups including, but not limited to, —$C_{1-12}$alkyl, —O—($C_{1-12}$alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_{1-12}$alkyl and aryl.

A "$C_{3-12}$ carbocyclo" refers to a $C_3$-$C_8$ carbocycle group defined above wherein one of the carbocycle groups' hydrogen atoms is replaced with a bond.

A "$C_{1-10}$alkylene" is a straight chain, saturated hydrocarbon group of the formula —(CH$_2$)$_{1-10}$—. Examples of a $C_1$-$C_{10}$ alkylene include methylene, ethylene, propylene, butylene, pentylene, hexylene, heptylene, ocytylene, nonylene and decalene.

An "arylene" is an aryl group which has two covalent bonds and can be in the ortho, meta, or para configurations as shown in the following structures:

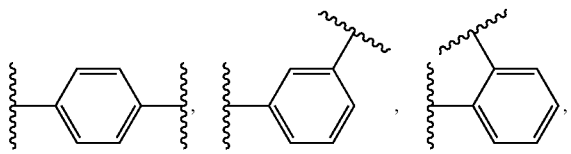

in which the phenyl group can be unsubstituted or substituted with up to four groups including, but not limited to, —$C_1$-$C_8$ alkyl, —O—($C_1$-$C_5$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_{3-12}$heterocyclyl" refers to an aromatic or non-aromatic $C_{3-12}$carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_{12}$heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_{3-12}$heterocyclo" refers to a $C_{3-12}$heterocycle group defined above wherein one of the heterocycle group's hydrogen atoms is replaced with a bond. A $C_3$-$C_{12}$ heterocyclo can be unsubstituted or substituted with up to six groups including, but not limited to, —$C_1$-$C_{12}$alkyl, —O—($C_1$-$C_{12}$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_{12}$alkyl and aryl.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡CH—).

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NR$_2$, —SO$_3^-$, —SO$_3$H, —S(=O)$_2$R, —OS(=O)$_2$OR, —S(=O)$_2$NR, S(=O)R, —OP(=O)(OR)$_2$, —P(=O)(OR)$_2$, —PO$^-$$_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, $C_2$-$C_{20}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5- thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be clearly understood that, although a number of prior art publications are referred to herein, this reference does not constitute an admission that any of these documents forms part of the common general knowledge in the art, in Australia or in any other country.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

Examples of an "amino protecting group" include, but are not limited to, 9-fluorenylmethyl carbamate (Fmoc), t-Butyl carbamate (Boc), benzyl carbamate, trifluoroacetamide, phthalimide, benzylamine, benzylideneamine, p-toluenesulfonamide, and triphenylmethylamine.

"Leaving group" refers to a functional group that can undergo an elimination reaction to form a double bond. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of an Exemplary Compound or Exemplary Conjugate. The Exemplary Compounds and Exemplary Conjugates contain at least one amino group, and accordingly acid addition salts can be formed with this amino group. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions.

Hence, a pharmaceutically acceptable salt can have one or more charged atoms and/or one or more counterion.

"Pharmaceutically acceptable solvate" or "solvate" refer to an association of one or more solvent molecules and a compound of the invention, e.g., an Exemplary Compound or Exemplary Conjugate. Examples of solvents that form pharmaceutically acceptable solvates include, but are not limited to, water, isopropanol, ethanol, methanol, DMSO, ethyl acetate, acetic acid, and ethanolamine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Examples of a "subject" include, but are not limited to, a human, rat, mouse, guinea pig, monkey, pig, goat, cow, horse, dog, cat, bird and fowl. In an exemplary embodiment, the subject is a human.

The term "inhibiting" or "inhibition," as used herein, refers to any detectable negative effect on a target biological process, such as cellular signal transduction, cell proliferation, tumorigenicity, and metastatic potential. Typically, an inhibition is reflected in a decrease of at least 10%, 20%, 30%, 40%, or 50% in target process (e.g., Smad3-mediated signaling or cancer proliferation), or any one of the downstream parameters mentioned above, when compared to a control.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the nature of the therapeutic agent, the manner of administration, and the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

Smad3 Inhibitor Compounds

The present disclosure provides compounds of Formula 1 or Formula 2, which can be described according to the following chemical structures:

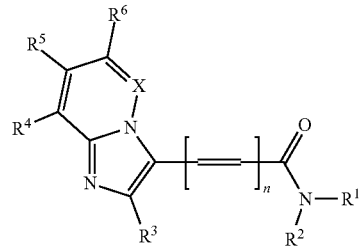

Formula 1

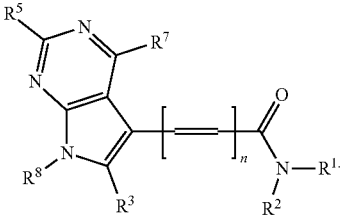

Formula 2

The above compounds of Formula 1 or Formula 2 may be further described as follows, where n represents 0 or 1, and X represents N or $CR^7$. $R^1$ and $R^2$ may be each independently selected from hydrogen, $C_{1\text{-}20}$alkyl, $C_{2\text{-}20}$alkenyl, $C_{2\text{-}20}$alkynyl, monocyclic or polycyclic carbocyclic, and monocyclic or polycyclic heterocyclic; or $R^1$ and $R^2$ join together to form a monocyclic or polycyclic heterocyclic. The $C_{1\text{-}20}$alkyl, $C_{2\text{-}20}$alkenyl, $C_{2\text{-}20}$alkynyl, may be each optionally interrupted with one or more heteroatoms (e.g. 1 to 3 heteroatoms) independently selected from O, N and S. The $C_{1\text{-}20}$alkyl, $C_{2\text{-}20}$alkenyl, $C_{2\text{-}20}$alkynyl, carbocyclic, and heterocyclic, may be each optionally substituted with one or more substituents independently selected from halo, CN, $NO_2$, $OC(O)R^9$, $C(O)R^9$, $C(O)NR^9R^{10}$, $C(O)OR^9$, OR', $OS(O)_2R^9$, $NR^9R^{10}$, $SR^9$, and $R^9$. $R^9$ and $R^{10}$ may be each independently selected from hydrogen, $C_{1\text{-}10}$alkyl, aryl$C_{1\text{-}10}$alkyl, hetaryl$C_{1\text{-}10}$alkyl, and heterocyclic. The $C_{1\text{-}10}$alkyl moiety of any one of these groups may be optionally interrupted with one or more heteroatoms independently selected from O, N and S. The $C_{1\text{-}10}$alkyl, aryl$C_{1\text{-}10}$alkyl, hetaryl$C_{1\text{-}10}$alkyl, and heterocyclic groups may be each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$. $R^{11}$ and $R^{12}$ may be each independently selected from hydrogen and $C_{1-6}$alkyl.

$R^3$, $R^4$, $R^5$, $R^6$, and $R^7$, when present, may be each independently selected from hydrogen, halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups may be each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, may be each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$; wherein $R^{11}$ and $R^{12}$ may be each independently selected from hydrogen, $C_{1-6}$alkyl, and $C_{1-6}$alkylhalo.

$R^8$, when present, may be selected from hydrogen, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups may be each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, may be each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$; wherein $R^{11}$ and $R^{12}$ may be each independently selected from hydrogen, $C_{1-6}$alkyl, and $C_{1-6}$alkylhalo.

It will be appreciated that any of the optional heteroatoms or substituents referred to above with reference to "one or more", may be any integer such as 1, 2, 3, 4, 5, 6, etc., or for example a range of 1 to 6 substituents, 1 to 3 substituents, or 1 to 2 substituents.

With reference to the above terms "n" and "X", the compounds of Formula 1 may be further described by the following chemical structures of Formula 1a or Formula 1b:

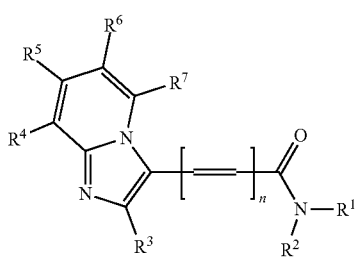

Formula 1a

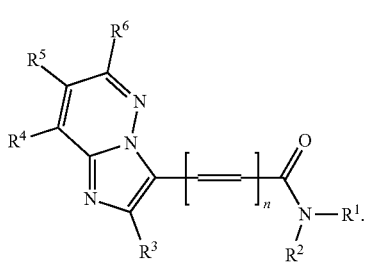

Formula 1b

The compounds of Formula 1a may be further described by the following chemical structures of Formula 1a(i) or Formula 1a(ii):

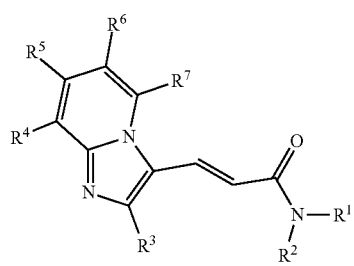

Formula 1a(i)

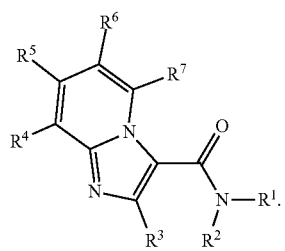

Formula 1a(ii)

The compounds of Formula 1b may be further described by the following chemical structures of Formula 1b(i) or Formula 1b(ii):

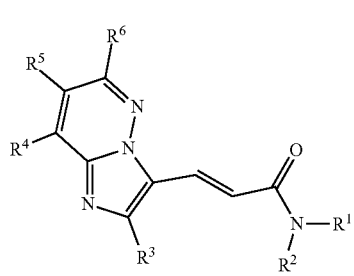

Formula 1b(i)

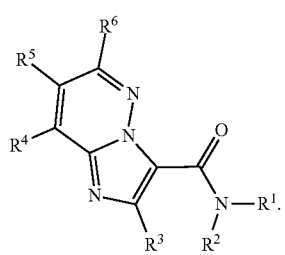

Formula 1b(ii)

The compounds of Formula 2 may be further described by the following chemical structures of Formula 2a(i) or Formula 2a(ii):

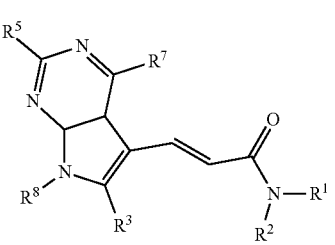

Formula 2a(i)

-continued

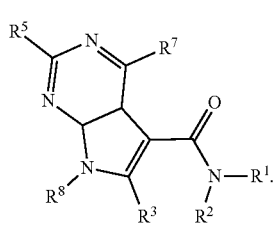

Formula 2a(ii)

The substituents of $R^1$ to $R^8$ for any one of the above chemical structures or Formulae are further described as follows.

$R^1$ and $R^2$ Substituents

For the compounds of Formula 1 or Formula 2 described herein, it will be appreciated that $R^1$ and $R^2$ are each attached to a common nitrogen atom, wherein the common nitrogen atom is itself attached to a carbonyl group (e.g. may be represented as a moiety of —C(=O)NR$^1$R$^2$). $R^1$ and $R^2$ may be independent groups or $R^1$ and $R^2$ may be joined together to form a heterocyclic group, which may be optionally substituted.

$R^1$ and $R^2$ as Independent Groups

When $R^1$ and $R^2$ are independent groups, $R^1$ and $R^2$ may be each independently selected from hydrogen, $C_{1-20}$alkyl, $C_{2-20}$alkenyl, $C_{2-20}$alkynyl, monocyclic or polycyclic carbocyclic, and monocyclic or polycyclic heterocyclic. $R^1$ and $R^2$ may be each independently selected from hydrogen, $C_{1-20}$alkyl, $C_{2-20}$alkenyl, $C_{2-20}$alkynyl. $R^1$ and $R^2$ may be each independently selected from hydrogen and $C_{1-20}$alkyl. It will be appreciated from the definitions described herein that the $C_{1-20}$alkyl may be a $C_{1-10}$alkyl, for example, which may also be optionally substituted. The $C_{1-20}$alkyl, $C_{2-20}$alkenyl, $C_{2-20}$alkynyl, may be each optionally interrupted with 1 to 3 heteroatoms independently selected from O, N and S. The $C_{1-20}$alkyl, $C_{2-20}$alkenyl, $C_{2-20}$alkynyl, may be each optionally interrupted with 1 to 3 heteroatoms independently selected from O. For example, a $C_{1-20}$alkyl group optionally interrupted with two O heteroatoms may comprise an ethylene glycol (—O—CH$_2$—CH$_2$—O—) moiety, or if optionally interrupted with a single O heteroatom may be a methoxy propanyl group (i.e. —CH$_2$—CH$_2$—CH$_2$—O—CH$_3$), for example. The $C_{1-20}$alkyl, $C_{2-20}$alkenyl, $C_{2-20}$alkynyl, carbocyclic, and heterocyclic, may be each optionally substituted with one or more substituents independently selected from halo, CN, NO$_2$, OC(O)R$^9$, C(O)R$^9$, C(O)NR$^9$R$^{10}$, C(O)OR$^9$, OR$^9$, OS(O)$_2$R$^9$, NR$^9$R$^{10}$, SR$^9$, and R$^9$.

$R^9$ and $R^{10}$ may be each independently selected from hydrogen, $C_{1-10}$alkyl, arylC$_{1-10}$alkyl, hetarylC$_{1-10}$alkyl, and heterocyclic. The $C_{1-10}$alkyl, arylC$_{1-10}$alkyl, hetarylC$_{1-10}$alkyl, and heterocyclic groups may be each optionally substituted with one or more substituents independently selected from halo, CN, NO$_2$, OC(O)R$^{11}$, C(O)R$^1$, C(O)NR$^{11}$R$^{12}$, C(O)OR$^{11}$, OR$^{11}$, OS(O)$_2$R$^{11}$, NR$^{11}$R$^{12}$, and SR$^{11}$. $R^{11}$ and $R^{12}$ may be each independently selected from hydrogen and $C_{1-6}$alkyl.

$R^1$ and $R^2$ as Joined Cyclic Group $R^1$ and $R^2$ may be joined together to form a monocyclic or polycyclic heterocyclic, which itself may be optionally substituted as described herein. The monocyclic or polycyclic heterocyclic may be a fully or partially saturated heterocyclic, for example may include groups such as pyrrolinyl, pyrrolidinyl, oxazinyl, piperidinyl or morpholinyl. The monocyclic and polycyclic heterocyclic may be saturated monocyclic heterocyclic fused to a carbocyclic group, for example fused to an aryl group such as a benzene group. The monocyclic or polycyclic heterocyclic group may be a 5 or 6 membered heterocyclic ring, which may be optionally substituted with 1-3 substituents as herein described and optionally fused with a carbocyclic or heterocyclic group, for example fused with an aryl group such as a benzene group, which itself may be optionally substituted.

$R^1$ and $R^2$ may join together to form an optionally substituted monocyclic or bicyclic heterocyclic. The bicyclic heterocyclic may be provided by a 5 or 6 membered heterocyclic ring fused with a carbocyclic or heterocyclic group, for example an aryl group such as an optionally substituted benzene group. The bicyclic heterocyclic may be a 5 or 6 membered heterocyclic ring fused to an optionally substituted benzene group, for example an optionally substituted indoline group.

With respect to the compounds of Formula 1 or Formula 2, or any embodiments thereof, the moiety —C(=O)NR$^1$R$^2$ referred to above wherein $R^1$ and $R^2$ join together to form an optionally substituted monocyclic or polycyclic heterocyclic may be provided by a group selected from Formula 3 or Formula 4:

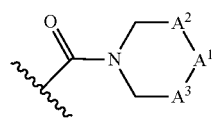

Formula 3

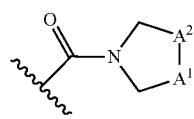

Formula 4 wherein $A^1$ may be selected from O, S, NR$^{14}$, and CR$^{14}$R$^{15}$;

$A^2$ and $A^3$ may be each independently selected from CR$^{14}$R$^{15}$;

$R^{14}$ and $R^{15}$ may be each independently selected from hydrogen, $C_{1-10}$alkyl, $C_{2-10}$alkenyl, $C_{2-10}$alkenyl, monocyclic or polycyclic carbocyclic, and monocyclic or polycyclic heterocyclic; or $R^{14}$ and $R^{15}$ if present may join together to form a carbocyclic or heterocyclic ring; and wherein the $C_{1-10}$alkyl, $C_{2-10}$alkenyl, $C_{2-10}$alkynyl, may be each optionally interrupted with one or more heteroatoms (e.g. 1 to 3 heteroatoms) independently selected from O, N and S; the $C_{1-10}$alkyl, $C_{2-10}$alkenyl, $C_{2-10}$alkynyl, carbocyclic, heterocyclic group, and heterocyclic ring, may be each optionally substituted with one or more substituents (e.g. 1 to 3 substituents) independently selected from halo, CN, NO$_2$, OC(O)R$^9$, C(O)R$^9$, C(O)NR$^9$R$^{10}$, C(O)OR$^9$, OR$^9$, OS(O)$_2$R$^9$, NR$^9$R$^{10}$, SR$^9$, and R$^9$. $R^9$ and $R^{10}$ may be each independently selected from groups as herein described. $R^9$ and $R^{10}$ may be each independently selected from hydrogen, $C_{1-10}$alkyl, arylC$_{1-10}$alkyl, hetarylC$_{1-10}$alkyl, and heterocyclic. The $C_{1-10}$alkyl moiety of any one of these groups may be optionally interrupted with one or more heteroatoms independently selected from O, N and S. The $C_{1-100}$alkyl, arylC$_{1-10}$alkyl, hetarylC$_{1-10}$alkyl, and heterocyclic groups may be each optionally substituted with 1 to 3 substituents independently selected from halo, CN, NO$_2$, OC(O)R$^{11}$, C(O)R$^{11}$, C(O)NR$^{11}$R$^{12}$, C(O)OR$^{11}$, $OR^{11}$, $OS(O)_2R^{11}$, $NR^{11}R^{12}$, and $SR^{11}$. $R^{11}$ and $R^{12}$ may be each independently selected from hydrogen and $C_{1-6}$alkyl.

The monocyclic or polycyclic carbocyclic or heterocyclic may be aromatic, for example may be a monocyclic or polycyclic aryl or heteroaryl. In one embodiment, the monocyclic or polycyclic carbocyclic is phenyl, which may be optionally substituted and optionally fused. Where the $R^{14}$ and $R^{15}$ join together to form a carbocyclic or heterocyclic ring, the carbocyclic or heterocyclic ring may be aromatic, for example may be a monocyclic or polycyclic aryl or heteroaryl. In one embodiment, the monocyclic or polycyclic carbocyclic is a benzene group, which may be optionally substituted and optionally fused.

Examples of the moiety of Formula 3 where $R^1$ and $R^2$ join together to form a monocyclic heterocyclic group may be provided by any one of Formulae 3a-c as follows:

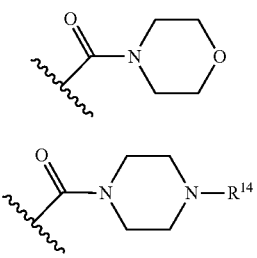

Formula 3a

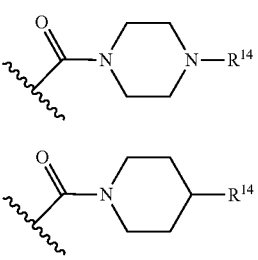

Formula 3b

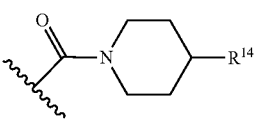

Formula 3c wherein $R^{14}$ may be provided according to any embodiments for those groups as described herein.

Further examples of the moiety of Formula 3 where $R^1$ and $R^2$ join together to form a bicyclic heterocyclic group may be provided by Formula 3d or Formula 3e as follows:

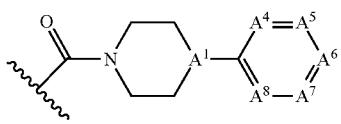

Formula 3d

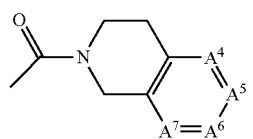

Formula 3e wherein
$A^1$ may be selected from N and CH;
$A^4$, $A^5$, $A^6$, $A^7$, and $A^8$, may be each independently selected from N and $CR^{14}$;
$R^{14}$ is selected from hydrogen, CN, $NO_2$, $OC(O)R^9$, $C(O)R^9$, $C(O)NR^9R^{10}$, $C(O)OR^9$, $OR^9$, $OS(O)_2R^9$, $NR^9R^{10}$, $SR^9$, and $R^9$; and
$R^9$ and $R^{10}$ may be each independently selected from hydrogen, $C_{1-10}$alkyl, aryl$C_{1-10}$alkyl, hetaryl$C_{1-10}$alkyl, and heterocyclic, which may be each optionally substituted and the $C_{1-10}$alkyl moiety of any one of these groups optionally interrupted with one or more heteroatoms independently selected from O, N and S.

For the above $R^9$ and $R^{10}$ groups, the $C_{1-10}$alkyl, aryl$C_{1-10}$alkyl, hetaryl$C_{1-10}$alkyl, and heterocyclic groups may be each optionally substituted with 1 to 3 substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, and $SR^{11}$. $R^{11}$ and $R^{12}$ may be each independently selected from hydrogen and $C_{1-6}$alkyl. The $C_{1-10}$alkyl, $C_{2-10}$alkenyl, $C_{2-10}$alkenyl, may be each optionally interrupted with 1 to 3 heteroatoms independently selected from O, N and S.

In an embodiment, $R^{14}$ is selected from hydrogen, $C(O)NR^9R^{10}$, $OR^9$, and $NR^9R^{10}$; and $R^9$ and $R^{10}$ are each independently selected as described above. $R^9$ and $R^{10}$ may be independently selected from hydrogen, $C_{1-6}$alkyl, monocyclic aryl$C_{1-6}$alkyl, monocyclic hetaryl$C_{1-6}$alkyl, and monocyclic heterocyclic, wherein the $C_{1-6}$alkyl moiety of any one of these groups may be optionally interrupted with one or more heteroatoms independently selected from O, N and S, and the $C_{1-6}$alkyl, monocyclic aryl$C_{1-6}$alkyl, monocyclic hetaryl$C_{1-6}$alkyl, and monocyclic heterocyclic, may be optionally substituted with 1 to 3 substituents as described above for $R^{11}$. The $C_{1-6}$alkyl, monocyclic aryl$C_{1-6}$alkyl, monocyclic hetaryl$C_{1-6}$alkyl, and monocyclic heterocyclic, may independently selected from halo, CN, $NH_2$, OH, and $OC_{1-6}$alkyl.

Examples of the moiety of Formula 3d may be provided by Formula 3d(i) or Formula 3d(ii) as follows:

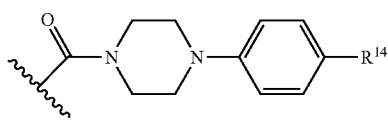

Formula 3d(i)

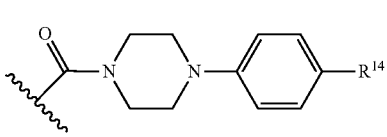

Formula 3d(ii)

wherein $R^{14}$ may be provided according to any embodiments for those groups as described above.

Examples of the moiety of Formula 3e may be provided by Formula 3e(i) or Formula 3e(ii) as follows:

Formula 3e(i)

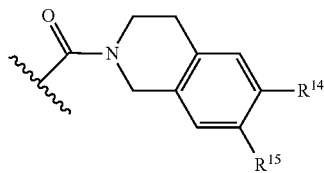

Formula 3e(i)

wherein $R^{14}$ and $R^{15}$ may be each independently selected according to any embodiments for those groups as described above.

$R^3$, $R^4$, $R^5$, $R^6$, R', and $R^8$ Substituents $R^3$, $R^4$, $R^5$, $R^6$, and $R^7$, when present, may be each independently selected from hydrogen, halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups may be each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, may be each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$; wherein $R^{11}$ and $R^{12}$ may be each independently selected from hydrogen, $C_{1-6}$alkyl, and $C_{1-6}$alkylhalo.

$R^8$, when present, may be selected from hydrogen, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups may be each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, may be each optionally substituted with one or more substituents independently selected from halo, CN, $NO_2$, $OC(O)R^{11}$, $C(O)R^{11}$, $C(O)NR^{11}R^{12}$, $C(O)OR^{11}$, $OR^{11}$, $OS(O)_2R^{11}$, $NR^{11}R^{12}$, $SR^{11}$, and $R^{11}$; wherein $R^{11}$ and $R^{12}$ may be each independently selected from hydrogen, $C_{1-6}$alkyl, and $C_{1-6}$alkylhalo.

In an embodiment, $R^3$, $R^4$, $R^5$, $R^6$, and $R^7$, may be each independently selected from hydrogen, halo, OH, CN, $NO_2$, $NH_2$, $C_{1-10}$alkyl, monocyclic heterocyclic, and monocyclic aryl; wherein the $C_{1-10}$alkyl is optionally interrupted with one or more heteroatoms selected from O, N and S, and wherein the $C_{1-10}$alkyl, heterocyclic, and aryl groups, are each optionally substituted with one or more substituents independently selected from halo, OH, CN, $NO_2$, $NH_2$, $C_{1-6}$alkyl, and $C_{1-6}$alkylhalo. In another embodiment, $R^4$, $R^5$, $R^6$, and $R^7$, may be each independently selected from hydrogen, halo, $C_{1-6}$alkyl, and $C_{1-6}$alkylhalo. $R^4$, $R^5$, $R^6$, and $R^7$, may be each independently selected from hydrogen, $C_{1-6}$alkyl, and $C_{1-6}$alkylhalo. $R^4$, $R^5$, $R^6$, and $R^7$, may be each selected from hydrogen.

In an embodiment, $R^3$ may be selected from hydrogen, halo, $C_{1-6}$alkyl, $C_{1-6}$alkylhalo, and monocyclic or bicyclic heterocyclic, and monocyclic or bicyclic aryl or hetaryl. $R^3$ may be selected from hydrogen and monocyclic or bicyclic aryl and hetaryl, wherein the aryl and hetaryl groups may be optionally substituted as described herein. $R^3$ may be selected from hydrogen and monocyclic aryl, for example phenyl, which may be optionally substituted as described above.

In an embodiment, $R^8$, when present, may be selected from hydrogen, $C_{1-6}$alkyl, $C_{1-6}$alkylhalo, and monocyclic aryl or hetaryl. $R^8$ may be hydrogen or $C_{1-6}$alkyl, for example methyl.

In an embodiment, $R^3$ is selected from hydrogen and optionally substituted monocyclic aryl or hetaryl; $R^4$, $R^5$, $R^6$, and $R^7$, are each independently selected from hydrogen, halo, $C_{1-6}$alkyl, and $C_{1-6}$alkylhalo; and $R^8$, when present, is selected from hydrogen or $C_{1-6}$alkyl.

In another embodiment, the optional substituents may be selected from any one or more of halogen, nitro, cyano, alkyl, haloalkyl, alkoxy, haloalkoxy, hydroxyl, hydroxyalkyl, carboxy, alkyloxycarbonyl, carbocycles, spirocycles, alkoxyalkyl, carboxyalkyl, acyl, aryl, aromatic heterocyclic group, heterocyclic group, arylalkyl, as described herein.

The compounds described herein may include salts, solvates, hydrates, isomers, tautomers, racemates, stereoisomers, enantiomers or diastereoisomers of those compounds. Asymmetric centers may exist in the complexes disclosed herein. These centers can be designated by the symbols "R" or "S," depending on the configuration of substituents around the chiral carbon atom. It should be understood that the present disclosure encompasses all stereochemical isomeric forms, including diastereomeric, enantiomeric, and epimeric forms, as well as D-isomers and L-isomers, and mixtures thereof. Additionally, the compounds disclosed herein may exist as geometric isomers. The present disclosure includes all cis, trans, syn (e.g. endo), anti (e.g. exo), entgegen (E), and zusammen (Z) isomers as well as the appropriate mixtures thereof. Additionally, compounds may exist as tautomers; all tautomeric isomers are provided by this disclosure.

It will also be appreciated that the compounds may comprise groups that have been suitably protected, for example amine groups that have been protected by using BOC groups. Suitable protecting groups, methods for their introduction and removal are described in Greene & Wuts, Protecting Groups in Organic Synthesis, Third Edition, 1999.

Where a compound has a net overall charge, for example where there is a substituent such as an amino group, the compound may be present in the form of a salt. In principle the counterion may be any organic or inorganic moiety that stabilizes the charge on the compound. Additionally, the compounds disclosed herein may exist in unsolvated as well as solvated forms. Polymorphic forms of the compounds are also encompassed.

Example Compounds

Proposed examples of the Smad3 inhibitor compounds of Formula 1 and Formula 2 may be provided by the following compounds:

Compounds of Formula 1

| Compound No. | Chemical Structure | Chemical Name |
| --- | --- | --- |
| Formula 1a(i) Compounds | | |
| 1 | 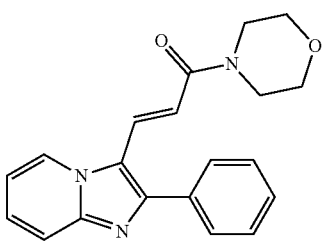 | (E)-1-morpholino-3-(2-phenylimidazo[1,2-a]pyridin-3-yl)prop-2-en-1-one |

| Compound No. | Chemical Name |
|---|---|
| 2 | (E)-N,N-diethyl-3-(2-phenylimidazo[1,2-a]pyridin-3-yl)acrylamide |
| 3 | (E)-N-(2-methoxyethyl)-N-methyl-3-(2-phenylimidazo[1,2-a]pyridin-3-yl)acrylamide |
| 4 | (E)-1-(3-hydroxypyrrolidin-1-yl)-3-(2-phenylimidazo[1,2-a]pyridin-3-yl)prop-2-en-1-one |
| 5 | (E)-1-(4-hydroxypiperidin-1-yl)-3-(2-phenylimidazo[1,2-a]pyridin-3-yl)prop-2-en-1-one |
| 6 | (E)-1-(4-methoxypiperidin-1-yl)-3-(2-phenylimidazo[1,2-a]pyridin-3-yl)prop-2-en-1-one |
| 7 | (E)-1-(3,4-dihydroisoquinolin-2(1H)-yl)-3-(2-phenylimidazo[1,2-a]pyridin-3-yl)prop-2-en-1-one |

| Compound No. | Chemical Structure | Chemical Name |
|---|---|---|
| 8 | 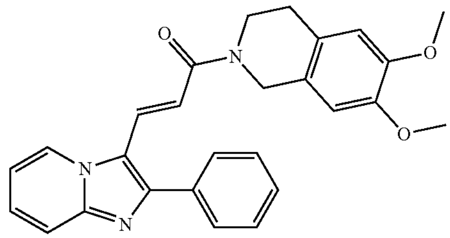 [SMILES: COc1cc2c(cc1OC)CN(C(=O)/C=C/c1c(-c3ccccc3)nc3ccccn13)CC2] | (E)-1-(6,7-dimethoxy-3,4-dihydroisoquinolin-2(1H)-yl)-3-(2-phenylimidazo[1,2-a]pyridin-3-yl)prop-2-en-1-one |
| 9 | 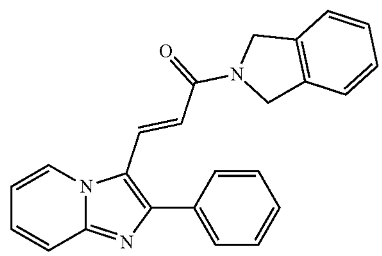 [SMILES: O=C(/C=C/c1c(-c2ccccc2)nc2ccccn12)N1Cc2ccccc2C1] | (E)-1-(isoindolin-2-yl)-3-(2-phenylimidazo[1,2-a]pyridin-3-yl)prop-2-en-1-one |
| 10 | 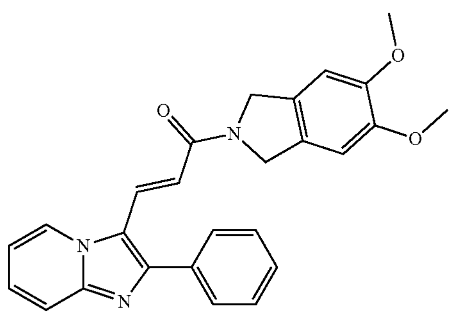 [SMILES: COc1cc2c(cc1OC)CN(C(=O)/C=C/c1c(-c3ccccc3)nc3ccccn13)C2] | (E)-1-(5,6-dimethoxyisoindolin-2-yl)-3-(2-phenylimidazo[1,2-a]pyridin-3-yl)prop-2-en-1-one |
| 11 | 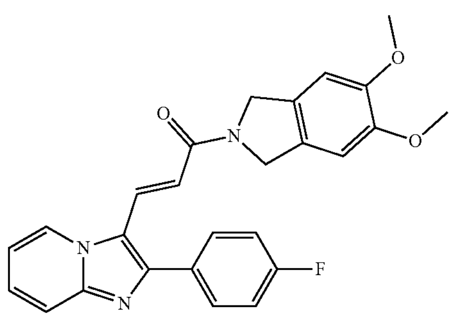 | (E)-1-(5,6-dimethoxyisoindolin-2-yl)-3-(2-(4-fluorophenyl)imidazo[1,2-a]pyridin-3-yl)prop-2-en-1-one |
| 12 | 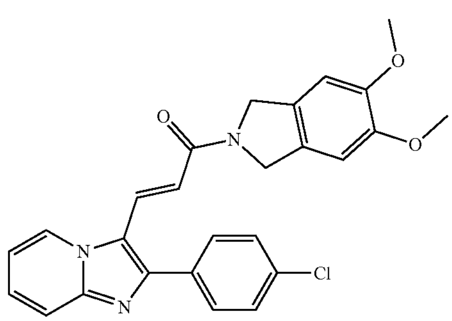 [SMILES: COc1cc2c(cc1OC)CN(C(=O)/C=C/c1c(-c3ccc(Cl)cc3)nc3ccccn13)C2] | (E)-3-(2-(4-chlorophenyl)imidazo[1,2-a]pyridin-3-yl)-1-(5,6-dimethoxyisoindolin-2-yl)prop-2-en-1-one |

| Compound No. | Chemical Structure | Chemical Name |
|---|---|---|
| 13 | 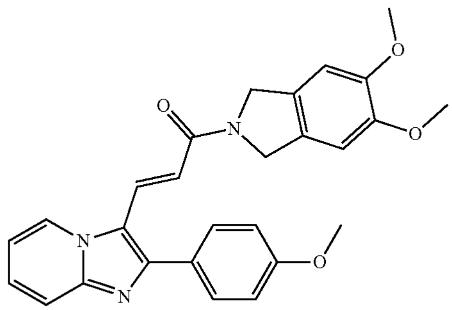 [SMILES: COc1ccc(-c2nc3ccccn3c2/C=C/C(=O)N2Cc3cc(OC)c(OC)cc3C2)cc1] | (E)-1-(5,6-dimethoxyisoindolin-2-yl)-3-(2-(4-methoxyphenyl)imidazo[1,2-a]pyridin-3-yl)prop-2-en-1-one |
| 14 | 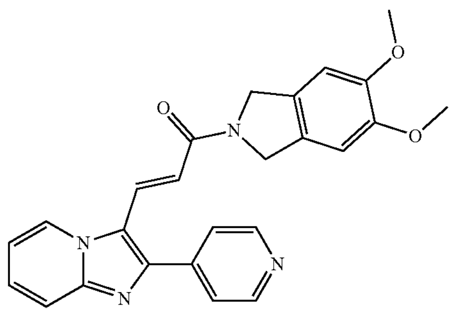 [SMILES: COc1cc2c(cc1OC)CN(C(=O)/C=C/c1c(-c3ccncc3)nc3ccccn13)C2] | (E)-1-(5,6-dimethoxyisoindolin-2-yl)-3-(2-(pyridin-4-yl)imidazo[1,2-a]pyridin-3-yl)prop-2-en-1-one |
| 15 | 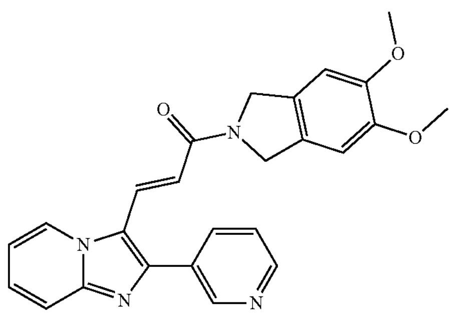 | (E)-1-(5,6-dimethoxyisoindolin-2-yl)-3-(2-(pyridin-3-yl)imidazo[1,2-a]pyridin-3-yl)prop-2-en-1-one |
| 16 | 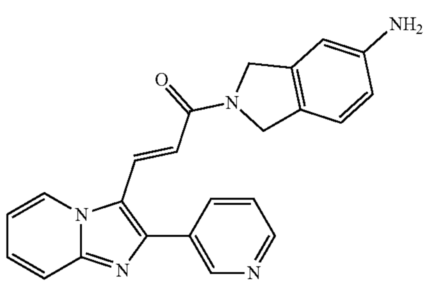 [SMILES: Nc1ccc2c(c1)CN(C(=O)/C=C/c1c(-c3cccnc3)nc3ccccn13)C2] | (E)-1-(5-aminoisoindolin-2-yl)-3-(2-(pyridin-3-yl)imidazo[1,2-a]pyridin-3-yl)prop-2-en-1-one |
| 17 | 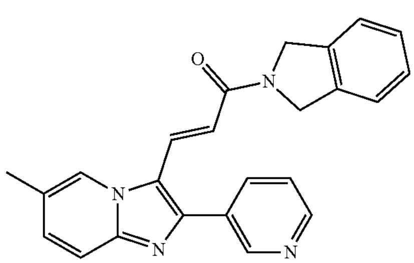 [SMILES: Cc1ccc2nc(-c3cccnc3)c(/C=C/C(=O)N3Cc4ccccc4C3)n2c1] | (E)-1-(isoindolin-2-yl)-3-(6-methyl-2-(pyridin-3-yl)imidazo[1,2-a]pyridin-3-yl)prop-2-en-1-one |

-continued

| Compound No. | Chemical Structure | Chemical Name |
|---|---|---|
| 18 | 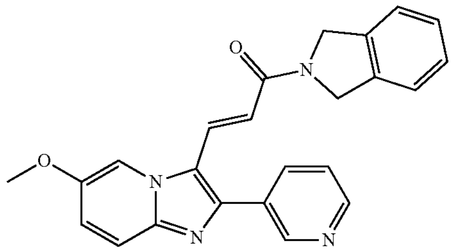 [SMILES: COc1ccc2nc(-c3cccnc3)c(/C=C/C(=O)N3Cc4ccccc4C3)n2c1] | (E)-1-(isoindolin-2-yl)-3-(6-methoxy-2-(pyridin-3-yl)imidazo[1,2-a]pyridin-3-yl)prop-2-en-1-one |
| 19 | 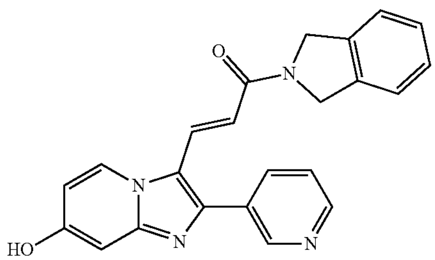 [SMILES: O=C(/C=C/c1c(-c2cccnc2)nc2cc(O)ccn12)N1Cc2ccccc2C1] | (E)-3-(7-hydroxy-2-(pyridin-3-yl)imidazo[1,2-a]pyridin-3-yl)-1-(isoindolin-2-yl)prop-2-en-1-one |
| 20 | 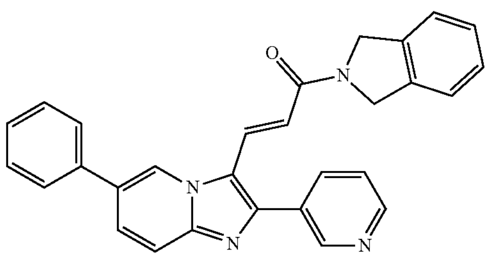 [SMILES: O=C(/C=C/c1c(-c2cccnc2)nc2ccc(-c3ccccc3)cn12)N1Cc2ccccc2C1] | (E)-1-(isoindolin-2-yl)-3-(6-phenyl-2-(pyridin-3-yl)imidazo[1,2-a]pyridin-3-yl)prop-2-en-1-one |
| 21 | 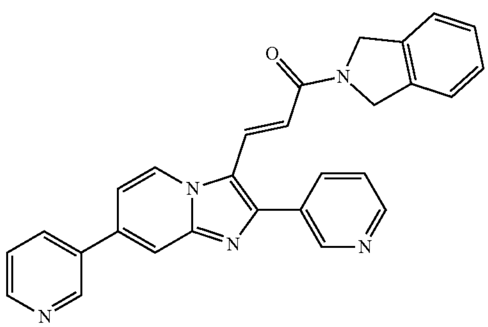 [SMILES: O=C(/C=C/c1c(-c2cccnc2)nc2cc(-c3cccnc3)ccn12)N1Cc2ccccc2C1] | (E)-3-(2,7-di(pyridin-3-yl)imidazo[1,2-a]pyridin-3-yl)-1-(isoindolin-2-yl)prop-2-en-1-one |
| 22 | 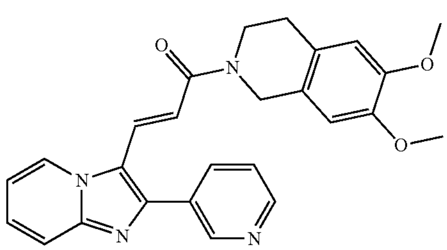 | (E)-1-(6,7-dimethoxy-3,4-dihydroisoquinolin-2(1H)-yl)-3-(2-(pyridin-3-yl)imidazo[1,2-a]pyridin-3-yl)prop-2-en-1-one |

| Compound No. | Chemical Structure | Chemical Name |
|---|---|---|
| 23 | 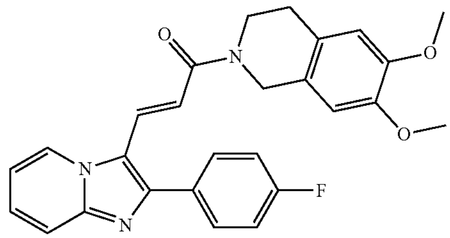 [SMILES: COc1cc2c(cc1OC)CN(C(=O)/C=C/c1c(-c3ccc(F)cc3)nc3ccccn13)CC2] | (E)-1-(6,7-dimethoxy-3,4-dihydroisoquinolin-2(1H)-yl)-3-(2-(4-fluorophenyl)imidazo[1,2-a]pyridin-3-yl)prop-2-en-1-one |
| 24 | 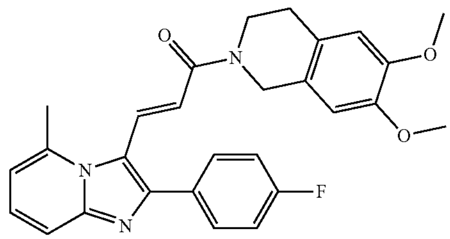 [SMILES: COc1cc2c(cc1OC)CN(C(=O)/C=C/c1c(-c3ccc(F)cc3)nc3cccc(C)n13)CC2] | (E)-1-(6,7-dimethoxy-3,4-dihydroisoquinolin-2(1H)-yl)-3-(2-(4-fluorophenyl)-5-methylimidazo[1,2-a]pyridin-3-yl)prop-2-en-1-one |
| 25 | 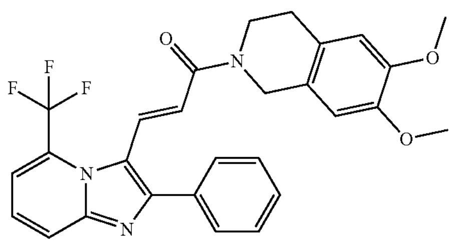 [SMILES: COc1cc2c(cc1OC)CN(C(=O)/C=C/c1c(-c3ccccc3)nc3cccc(C(F)(F)F)n13)CC2] | (E)-1-(6,7-dimethoxy-3,4-dihydroisoquinolin-2(1H)-yl)-3-(2-phenyl-5-(trifluoromethyl)imidazo[1,2-a]pyridin-3-yl)prop-2-en-1-one |
| 26 | 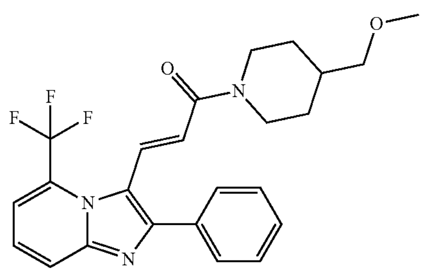 [SMILES: COCC1CCN(C(=O)/C=C/c2c(-c3ccccc3)nc3cccc(C(F)(F)F)n23)CC1] | (E)-1-(4-(methoxymethyl)piperidin-1-yl)-3-(2-phenyl-5-(trifluoromethyl)imidazo[1,2-a]pyridin-3-yl)prop-2-en-1-one |

Formula 1a(ii) Compounds

| Compound No. | Chemical Structure | Chemical Name |
|---|---|---|
| 27 | | (2-phenylimidazo[1,2-a]pyridin-3-yl)(4-(pyridin-3-yl)piperazin-1-yl)methanone |
| 28 | | (4-(6-(dimethylamino)pyridin-3-yl)piperazin-1-yl)(2-phenylimidazo[1,2-a]pyridin-3-yl)methanone |

-continued

| Compound No. | Chemical Structure | Chemical Name |
|---|---|---|
| 29 | 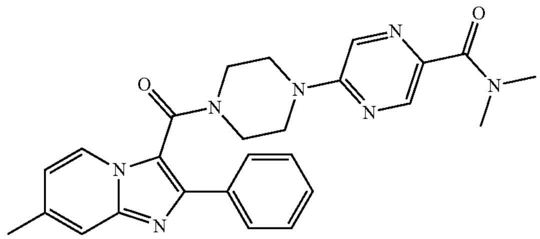 | N,N-dimethyl-5-(4-(7-methyl-2-phenylimidazo[1,2-a]pyridine-3-carbonyl)piperazin-1-yl)pyrazine-2-carboxamide |
| 30 | 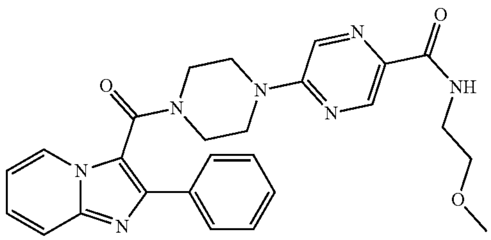 [SMILES: COCCNC(=O)c1cnc(N2CCN(C(=O)c3c(-c4ccccc4)nc4ccccn34)CC2)cn1] | N-(2-methoxyethyl)-5-(4-(2-phenylimidazo[1,2-a]pyridine-3-carbonyl)piperazin-1-yl)pyrazine-2-carboxamide |
| 31 | 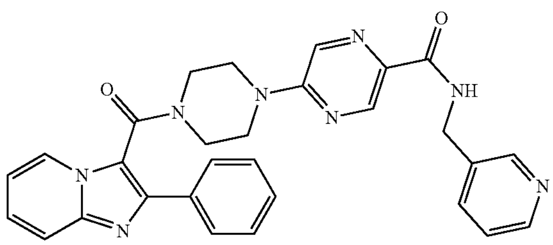 | 5-(4-(2-phenylimidazo[1,2-a]pyridine-3-carbonyl)piperazin-1-yl)-N-(pyridin-3-ylmethyl)pyrazine-2-carboxamide |
| 32 | 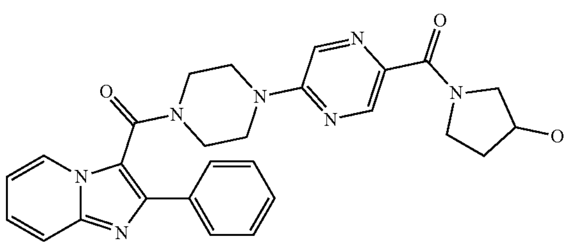 [SMILES: O=C(c1cnc(N2CCN(C(=O)c3c(-c4ccccc4)nc4ccccn34)CC2)cn1)N1CCC(O)C1] | (3-hydroxypyrrolidin-1-yl)(5-(4-(2-phenylimidazo[1,2-a]pyridine-3-carbonyl)piperazin-1-yl)pyrazin-2-yl)methanone |
| 33 | 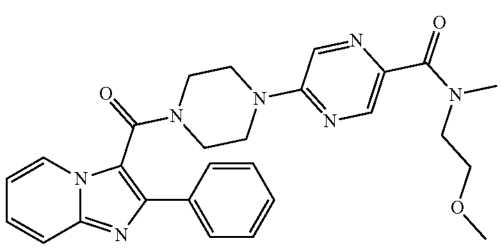 [SMILES: COCCN(C)C(=O)c1cnc(N2CCN(C(=O)c3c(-c4ccccc4)nc4ccccn34)CC2)cn1] | N-(2-methoxyethyl)-N-methyl-5-(4-(2-phenylimidazo[1,2-a]pyridine-3-carbonyl)piperazin-1-yl)pyrazine-2-carboxamide |
| 34 | 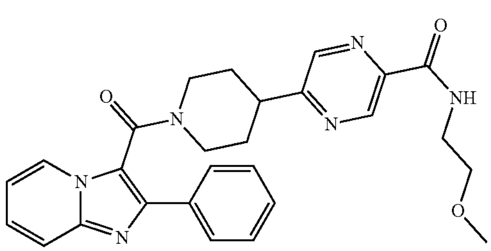 | N-(2-methoxyethyl)-5-(1-(2-phenylimidazo[1,2-a]pyridine-3-carbonyl)piperidin-4-yl)pyrazine-2-carboxamide |

| Compound No. | Chemical Structure | Chemical Name |
| --- | --- | --- |
| 35 | 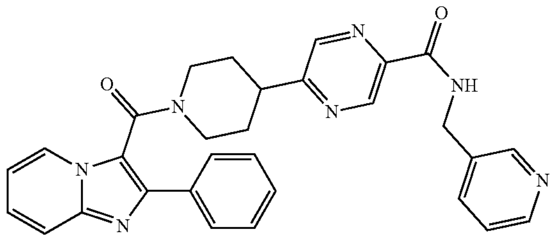 | 5-(1-(2-phenylimidazo[1,2-a]pyridine-3-carbonyl)piperidin-4-yl)-N-(pyridin-3-ylmethyl)pyrazine-2-carboxamide |
| 36 | 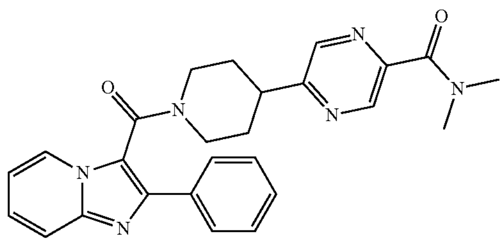 [SMILES: CN(C)C(=O)c1cnc(C2CCN(C(=O)c3c(-c4ccccc4)nc4ccccn34)CC2)cn1] | N,N-dimethyl-5-(1-(2-phenylimidazo[1,2-a]pyridine-3-carbonyl)piperidin-4-yl)pyrazine-2-carboxamide |
| 37 | 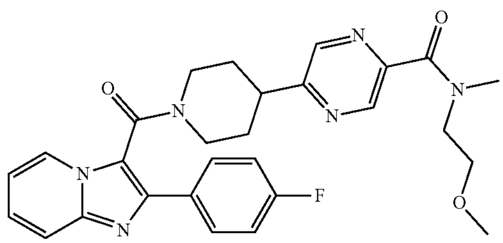 [SMILES: COCCN(C)C(=O)c1cnc(C2CCN(C(=O)c3c(-c4ccc(F)cc4)nc4ccccn34)CC2)cn1] | 5-(1-(2-(4-fluorophenyl)imidazo[1,2-\a]pyridine-3-carbonyl)piperidin-4-yl)-N-(2-methoxyethyl)-N-methylpyrazine-2-carboxamide |
| 38 | 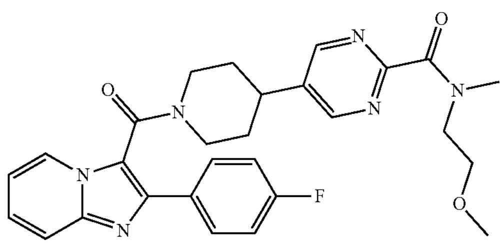 | 5-(1-(2-(4-fluorophenyl)imidazo[1,2-a]pyridine-3-carbonyl)piperidin-4-yl)-N-(2-methoxyethyl)-N-methylpyrimidine-2-carboxamide |
| Formula 1b(i) Compounds | | |
| 39 | 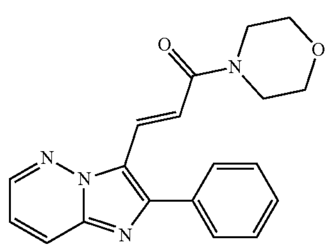 [SMILES: O=C(/C=C/c1c(-c2ccccc2)nc2cccnn12)N1CCOCC1] | (E)-1-morpholino-3-(2-phenylimidazo[1,2-b]pyridazin-3-yl)prop-2-en-1-one |
| 40 | 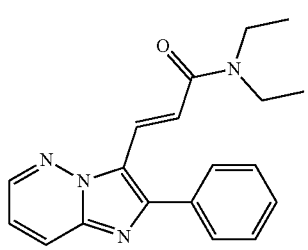 [SMILES: CCN(CC)C(=O)/C=C/c1c(-c2ccccc2)nc2cccnn12] | (E)-N,N-diethyl-3-(2-phenylimidazo[1,2-b]pyridazin-3-yl)acrylamide |

| Compound No. | Chemical Structure | Chemical Name |
|---|---|---|
| 41 | 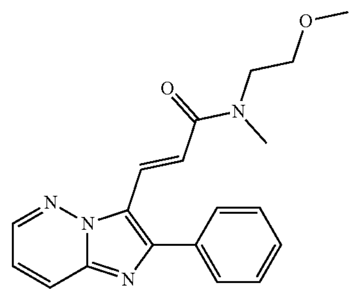 [SMILES: COCCN(C)C(=O)/C=C/c1c(-c2ccccc2)nc2cccnn12] | (E)-N-(2-methoxyethyl)-N-methyl-3-(2-phenylimidazo[1,2-b]pyridazin-3-yl)acrylamide |
| 42 | 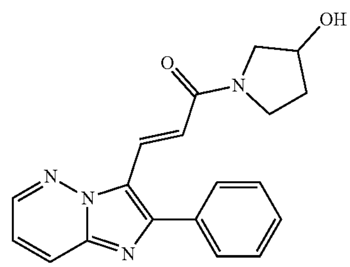 [SMILES: O=C(/C=C/c1c(-c2ccccc2)nc2cccnn12)N1CCC(O)C1] | (E)-1-(3-hydroxypyrrolidin-1-yl)-3-(2-phenylimidazo[1,2-b]pyridazin-3-yl)prop-2-en-1-one |
| 43 | 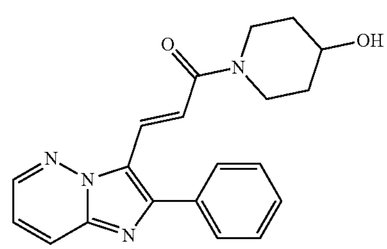 [SMILES: O=C(/C=C/c1c(-c2ccccc2)nc2cccnn12)N1CCC(O)CC1] | (E)-1-(4-hydroxypiperidin-1-yl)-3-(2-phenylimidazo[1,2-b]pyridazin-3-yl)prop-2-en-1-one |
| 44 | 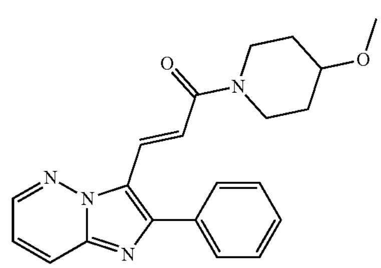 | (E)-1-(4-methoxypiperidin-1-yl)-3-(2-phenylimidazo[1,2-b]pyridazin-3-yl)prop-2-en-1-one |
| 45 | 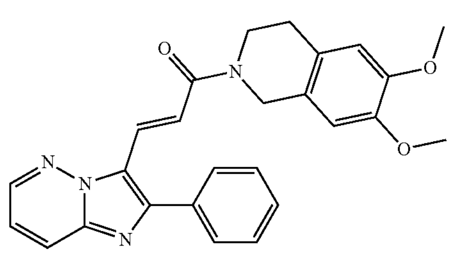 [SMILES: COc1cc2c(cc1OC)CN(C(=O)/C=C/c1c(-c3ccccc3)nc3cccnn13)CC2] | (E)-1-(6,7-dimethoxy-3,4-dihydroisoquinolin-2(1H)-yl)-3-(2-phenylimidazo[1,2-b]pyridazin-3-yl)prop-2-en-1-one |

| Compound No. | Chemical Name |
|---|---|
| 46 | (E)-1-(5,6-dimethoxyisoindolin-2-yl)-3-(2-phenylimidazo[1,2-b]pyridazin-3-yl)prop-2-en-1-one |
| 47 | (E)-1-(5,6-dimethoxyisoindolin-2-yl)-3-(2-(pyridin-3-yl)imidazo[1,2-b]pyridazin-3-yl)prop-2-en-1-one |
| 48 | (E)-1-(6,7-dimethoxy-3,4-dihydroisoquinolin-2(1H)-yl)-3-(2-(pyridin-3-yl)imidazo[1,2-b]pyridazin-3-yl)prop-2-en-1-one |
| 49 | (E)-1-(6,7-dimethoxy-3,4-dihydroisoquinolin-2(1H)-yl)-3-(6-methyl-2-phenylimidazo[1,2-b]pyridazin-3-yl)prop-2-en-1-one |
| 50 | (E)-1-(5,6-dimethoxyisoindolin-2-yl)-3-(2-(4-fluorophenyl)imidazo[1,2-b]pyridazin-3-yl)prop-2-en-1-one |

-continued

| Compound No. | Chemical Structure | Chemical Name |
|---|---|---|
| 51 | 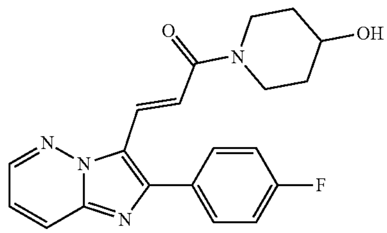 [SMILES: O=C(/C=C/c1c(-c2ccc(F)cc2)nc2cccnn12)N1CCC(O)CC1] | (E)-3-(2-(4-fluorophenyl)imidazo[1,2-b]pyridazin-3-yl)-1-(4-hydroxypiperidin-1-yl)prop-2-en-1-one |
| 52 | 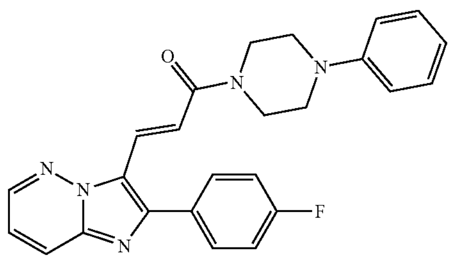 [SMILES: O=C(/C=C/c1c(-c2ccc(F)cc2)nc2cccnn12)N1CCN(c2ccccc2)CC1] | (E)-3-(2-(4-fluorophenyl)imidazo[1,2-b]pyridazin-3-yl)-1-(4-phenylpiperazin-1-yl)prop-2-en-1-one |
| 53 | 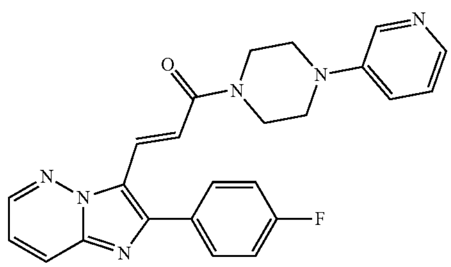 [SMILES: O=C(/C=C/c1c(-c2ccc(F)cc2)nc2cccnn12)N1CCN(c2cccnc2)CC1] | (E)-3-(2-(4-fluorophenyl)imidazo[1,2-b]pyridazin-3-yl)-1-(4-(pyridin-3-yl)piperazin-1-yl)prop-2-en-1-one |
| 54 | 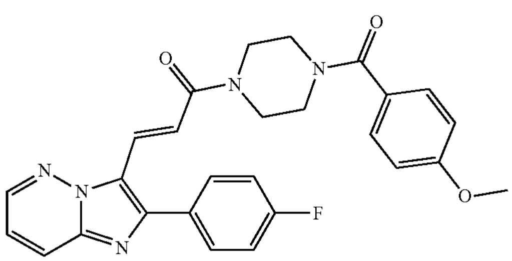 [SMILES: COc1ccc(C(=O)N2CCN(C(=O)/C=C/c3c(-c4ccc(F)cc4)nc4cccnn34)CC2)cc1] | (E)-3-(2-(4-fluorophenyl)imidazo[1,2-b]pyridazin-3-yl)-1-(4-(4-methoxybenzoyl)piperazin-1-yl)prop-2-en-1-one |
| Formula 1b(ii) Compounds | | |
| 55 | 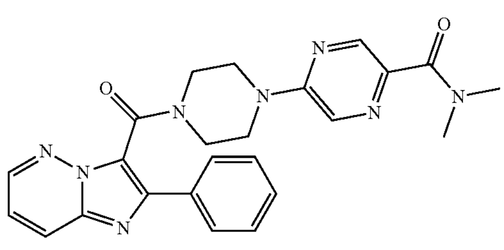 [SMILES: CN(C)C(=O)c1cnc(N2CCN(C(=O)c3c(-c4ccccc4)nc4cccnn34)CC2)cn1] | N,N-dimethyl-5-(4-(2-phenylimidazo[1,2-b]pyridazine-3-carbonyl)piperazin-1-yl)pyrazine-2-carboxamide |
| 56 | 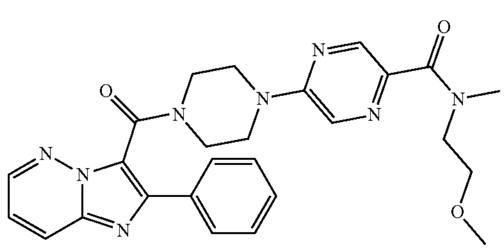 [SMILES: COCCN(C)C(=O)c1cnc(N2CCN(C(=O)c3c(-c4ccccc4)nc4cccnn34)CC2)cn1] | N-(2-methoxyethyl)-N-methyl-5-(4-(2-phenylimidazo[1,2-b]pyridazine-3-carbonyl)piperazin-1-yl)pyrazine-2-carboxamide |

-continued

| Compound No. | Chemical Structure | Chemical Name |
|---|---|---|
| 57 | 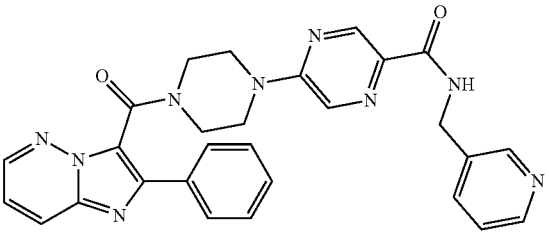 [SMILES: O=C(NCc1cccnc1)c1cnc(N2CCN(C(=O)c3c(-c4ccccc4)nc4cccnn34)CC2)cn1] | 5-(4-(2-phenylimidazo[1,2-b]pyridazine-3-carbonyl)piperazin-1-yl)-N-(pyridin-3-ylmethyl)pyrazine-2-carboxamide |
| 58 | 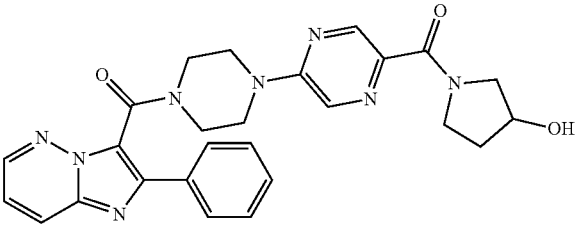 [SMILES: O=C(c1cnc(N2CCN(C(=O)c3c(-c4ccccc4)nc4cccnn34)CC2)cn1)N1CCC(O)C1] | (3-hydroxypyrrolidin-1-yl)(5-(4-(2-phenylimidazo[1,2-b]pyridazine-3-carbonyl)piperazin-1-yl)pyrazin-2-yl)methanone |
| 59 | 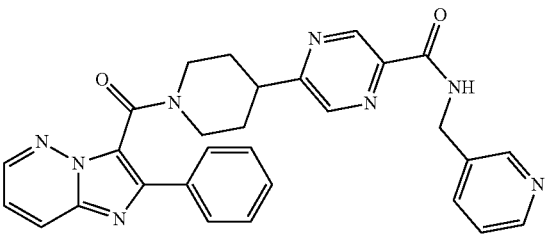 [SMILES: O=C(NCc1cccnc1)c1cnc(C2CCN(C(=O)c3c(-c4ccccc4)nc4cccnn34)CC2)cn1] | 5-(1-(2-phenylimidazo[1,2-b]pyridazine-3-carbonyl)piperidin-4-yl)-N-(pyridin-3-ylmethyl)pyrazine-2-carboxamide |
| 60 | 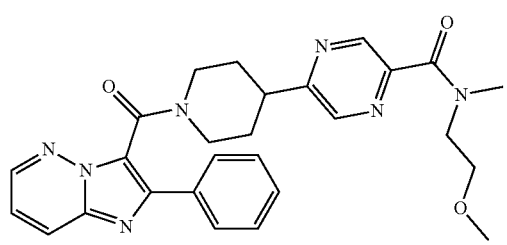 [SMILES: COCCN(C)C(=O)c1cnc(C2CCN(C(=O)c3c(-c4ccccc4)nc4cccnn34)CC2)cn1] | N-(2-methoxyethyl)-N-methyl-5-(1-(2-phenylimidazo[1,2-b]pyridazine-3-carbonyl)piperidin-4-yl)pyrazine-2-carboxamide |

Compounds of Formula 2

| Compound No. | Chemical Structure | Chemical Name |
|---|---|---|
| | Formula 2a(i) Compounds | |
| 61 | 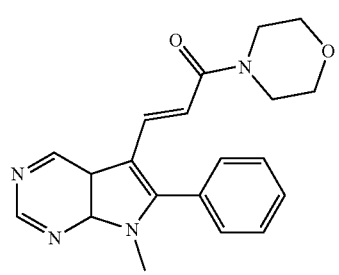 [SMILES: CN1C(c2ccccc2)=C(/C=C/C(=O)N2CCOCC2)C2C=NC=NC21] | (E)-3-(7-methyl-6-phenyl-4a,7a-dihydro-7H-pyrrolo[2,3-d]pyrimidin-5-yl)-1-morpholinoprop-2-en-1-one |

| Compound No. | Chemical Structure | Chemical Name |
|---|---|---|
| 62 | 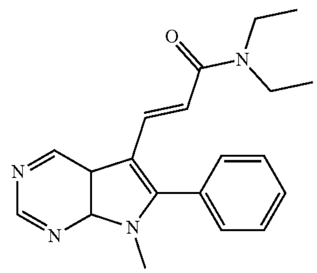 [SMILES: CCN(CC)C(=O)/C=C/C1=C(c2ccccc2)N(C)C2N=CN=CC12] | (E)-N,N-diethyl-3-(7-methyl-6-phenyl-4a,7a-dihydro-7H-pyrrolo[2,3-d]pyrimidin-5-yl)acrylamide |
| 63 | 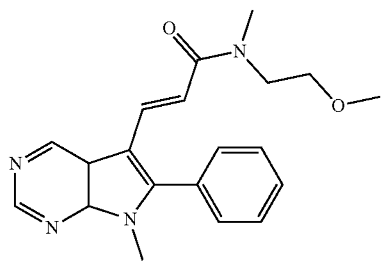 [SMILES: COCCN(C)C(=O)/C=C/C1=C(c2ccccc2)N(C)C2N=CN=CC12] | (E)-N-(2-methoxyethyl)-N-methyl-3-(7-methyl-6-phenyl-4a,7a-dihydro-7H-pyrrolo[2,3-d]pyrimidin-5-yl)acrylamide |
| 64 | 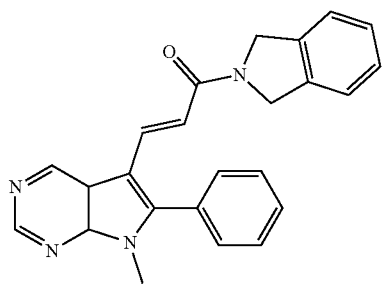 [SMILES: CN1C(c2ccccc2)=C(/C=C/C(=O)N2Cc3ccccc3C2)C2C=NC=NC21] | (E)-1-(isoindolin-2-yl)-3-(7-methyl-6-phenyl-4a,7a-dihydro-7H-pyrrolo[2,3-d]pyrimidin-5-yl)prop-2-en-1-one |
| 65 | 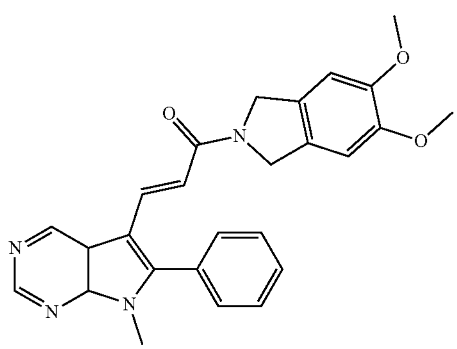 [SMILES: COc1cc2c(cc1OC)CN(C(=O)/C=C/C1=C(c3ccccc3)N(C)C3N=CN=CC13)C2] | (E)-1-(5,6-dimethoxyisoindolin-2-yl)-3-(7-methyl-6-phenyl-4a,7a-dihydro-7H-pyrrolo[2,3-d]pyrimidin-5-yl)prop-2-en-1-one |
| 66 | 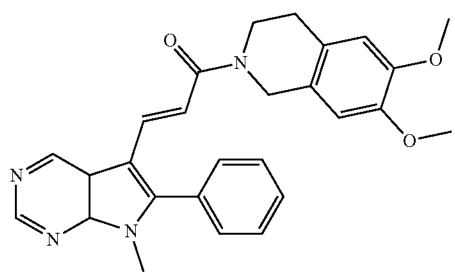 [SMILES: COc1cc2c(cc1OC)CN(C(=O)/C=C/C1=C(c3ccccc3)N(C)C3N=CN=CC13)CC2] | (E)-1-(6,7-dimethoxy-3,4-dihydroisoquinolin-2(1H)-yl)-3-(7-methyl-6-phenyl-4a,7a-dihydro-7H-pyrrolo[2,3-d]pyrimidin-5-yl)prop-2-en-1-one |

| Compound No. | Chemical Structure | Chemical Name |
|---|---|---|
| 67 | | (E)-3-(6-(4-fluorophenyl)-7-methyl-4a,7a-dihydro-7H-pyrrolo[2,3-d]pyrimidin-5-yl)-1-(4-hydroxypiperidin-1-yl)prop-2-en-1-one |
| 68 | | (E)-3-(6-(4-fluorophenyl)-7-methyl-4a,7a-dihydro-7H-pyrrolo[2,3-d]pyrimidin-5-yl)-1-(4-methoxypiperidin-1-yl)prop-2-en-1-one |

Formula 2a(ii) Compounds

| Compound No. | Chemical Structure | Chemical Name |
|---|---|---|
| 69 | 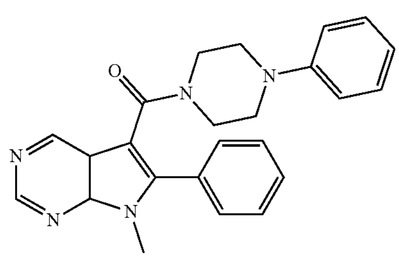 [SMILES: CN1C(c2ccccc2)=C(C(=O)N2CCN(c3ccccc3)CC2)C2C=NC=NC21] | (7-methyl-6-phenyl-4a,7a-dihydro-7H-pyrrolo[2,3-d]pyrimidin-5-yl)(4-phenylpiperazin-1-yl)methanone |
| 70 | 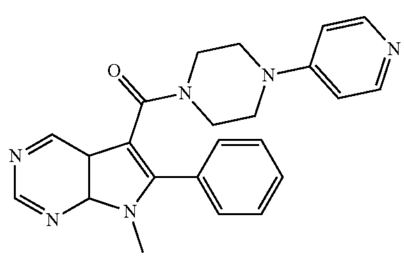 [SMILES: CN1C(c2ccccc2)=C(C(=O)N2CCN(c3ccncc3)CC2)C2C=NC=NC21] | (7-methyl-6-phenyl-4a,7a-dihydro-7H-pyrrolo[2,3-d]pyrimidin-5-yl)(4-(pyridin-4-yl)piperazin-1-yl)methanone |
| 71 | 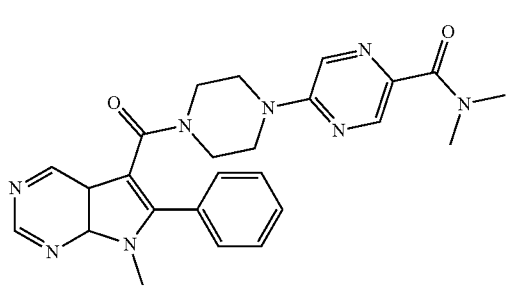 | N,N-dimethyl-5-(4-(7-methyl-6-phenyl-4a,7a-dihydro-7H-pyrrolo[2,3-d]pyrimidine-5-carbonyl)piperazin-1-yl)pyrazine-2-carboxamide |

| Compound No. | Chemical Structure | Chemical Name |
| --- | --- | --- |
| 72 | 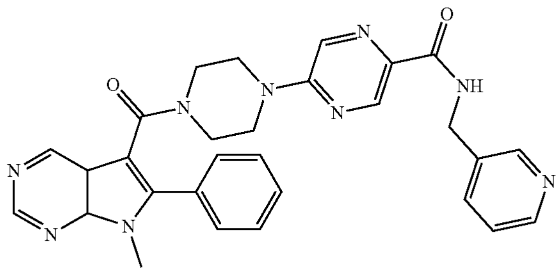 | 5-(4-(7-methyl-6-phenyl-4a,7a-dihydro-7H-pyrrolo[2,3-d]pyrimidine-5-carbonyl)piperazin-1-yl)-N-(pyridin-3-ylmethyl)pyrazine-2-carboxamide |
| 73 | 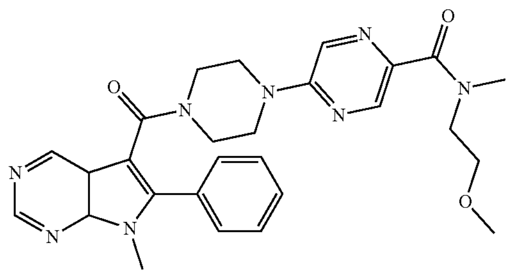 [SMILES: COCCN(C)C(=O)c1cnc(N2CCN(C(=O)C3=C(c4ccccc4)N(C)C4N=CN=CC34)CC2)cn1] | N-(2-methoxyethyl)-N-methyl-5-(4-(7-methyl-6-phenyl-4a,7a-dihydro-7H-pyrrolo[2,3-d]pyrimidine-5-carbonyl)piperazin-1-yl)pyrazine-2-carboxamide |
| 74 | 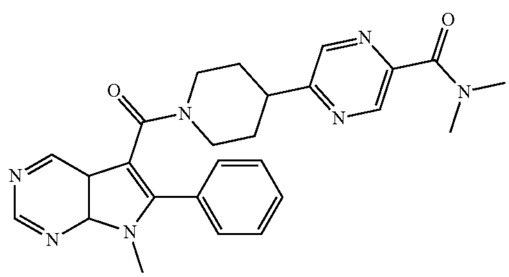 | N,N-dimethyl-5-(1-(7-methyl-6-phenyl-4a,7a-dihydro-7H-pyrrolo[2,3-d]pyrimidine-5-carbonyl)piperidin-4-yl)pyrazine-2-carboxamide |
| 75 | 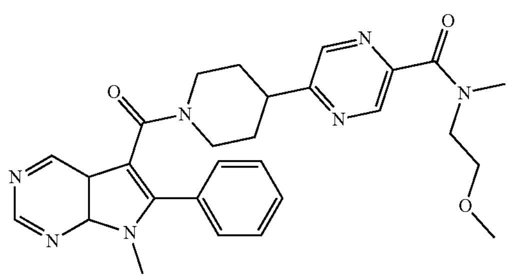 [SMILES: COCCN(C)C(=O)c1cnc(C2CCN(C(=O)C3=C(c4ccccc4)N(C)C4N=CN=CC34)CC2)cn1] | N-(2-methoxyethyl)-N-methyl-5-(1-(7-methyl-6-phenyl-4a,7a-dihydro-7H-pyrrolo[2,3-d]pyrimidine-5-carbonyl)piperidin-4-yl)pyrazine-2-carboxamide |
| 76 | 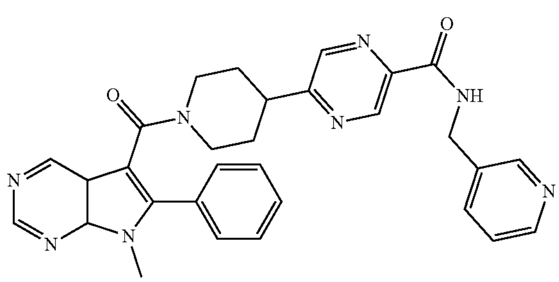 [SMILES: CN1C(c2ccccc2)=C(C(=O)N2CCC(c3cnc(C(=O)NCc4cccnc4)cn3)CC2)C2C=NC=NC21] | 5-(1-(7-methyl-6-phenyl-4a,7a-dihydro-7H-pyrrolo[2,3-d]pyrimidine-5-carbonyl)piperidin-4-yl)-N-(pyridin-3-ylmethyl)pyrazine-2-carboxamide |

Methods of Treatment and Cell Inhibition

The present disclosure provides a method for inhibiting proliferation of a cell, comprising the step of contacting the cell with an effective amount of an inhibitor of Smad3 selected from a compound of Formula 1 or Formula 2.

There is also provided a method for treating cancer by administration of an effective amount of a compound of Formula 1 or Formula 2, or composition thereof, according to any embodiment thereof as described herein, to a subject in need of treatment thereof.

The method for inhibiting proliferation of a cell, includes but is not limited to inhibiting cancer cell proliferation, tumor growth, invasion, and metastasis. The method includes the step of contacting the cell with an effective amount of an inhibitor of Smad3 selected from a compound of Formula 1 or Formula 2, or any embodiments thereof as described herein. The cell may be a cancer cell, which may be within a human body. The cancer may be lung carcinoma or melanoma, including primary and metastatic cancers. Also targeted by the Smad3 inhibitor are various cells surrounding the cancer tissue or cancer stromal cells, i.e., cells in the cancer microenvironment of the primary or metastatic cancer in the human body, including vascular endothelial cells, fibroblasts, neutrophils, eosinophils, mast cells, T cells and subsets, B cells, macrophages, and NK cells within the cancer microenvironment. The targeted cell may be a metastatic cancer cell within the human body such as a cell in the lymph nodes, liver, lung, bone, kidney, brain, gastric, or colon tissues. In other words, the metastatic cancer may be a cancer of the lymph nodes, liver, lung, bone, kidney, brain, gastric, or colon tissues. The contacting step may involve subcutaneous, intramuscular, intravenous, intraperitoneal, topical, or oral administration. For example, the Smad3 inhibitor compound may be administered in the form of a solution, a powder, a paste/cream, a tablet, or a capsule.

The anti-cancer effects of a Smad3 inhibitor of the present disclosure can be demonstrated in in vivo assays. For example, a Smad3 inhibitor can be injected into animals that have a compromised immune system (e.g., nude mice, SCID mice, or NOD/SCID mice) and therefore permit xenograft tumors. Injection methods can be subcutaneous, intramuscular, intravenous, intraperitoneal, or intratumoral in nature. Tumor development is subsequently monitored by various means, such as measuring tumor volume and scoring secondary lesions due to metastases, in comparison with a control group of animals with similar tumors but not given the inhibitor. The Examples section of this disclosure provides detailed description of some exemplary in vivo assays. An inhibitory effect is detected when a negative effect on tumor growth or metastasis is established in the test group. The negative effect may be at least a 10% decrease; or the decrease may be at least 20%, 30%, 40%, 50%, 60%, 70%, 80%, or 90%.

Pharmaceutical Compositions

The present disclosure also provides a pharmaceutical composition comprising a compound selected from Formula 1 or Formula 2, or a pharmaceutically acceptable salt thereof, as described herein, and a pharmaceutically acceptable excipient.

The composition or formulation may be useful for inhibiting cell proliferation, e.g., for treating cancer by suppressing cancer cell growth, and by blocking cancer supportive cells within the cancer microenvironment, thereby preventing cancer invasion and metastasis. The composition may include an effective amount of an inhibitor of Smad3 and a pharmaceutically acceptable excipient. The composition may be formulated for subcutaneous, intramuscular, intravenous, intraperitoneal, topical, or oral administration. For example, the composition may be in the form of a solution, a powder, a paste/cream, a tablet, or a capsule.

The pharmaceutical compositions may be suitable for use in a variety of drug delivery systems. Suitable formulations for use in the present disclosure may be found in Remington's Pharmaceutical Sciences, Mack Publishing Company, Philadelphia, Pa., 17th ed. (1985). For a brief review of methods for drug delivery, see, Langer, Science 249: 1527-1533 (1990).

The pharmaceutical compositions may be administered by various routes, e.g., oral, topical, subcutaneous, transdermal, intramuscular, intravenous, or intraperitoneal. The routes of administering the pharmaceutical compositions may comprise local delivery to an organ or tissue suffering from a condition exacerbated by TGF-β/Smad3 mediated signaling (e.g., intratumor injection to a tumor) at daily doses of about 0.01-2500 mg, for example 2.5-500 mg, of a Smad3 inhibitor for a 70 kg adult human per day. The appropriate dose may be administered in a single daily dose or as divided doses presented at appropriate intervals, for example as two, three, four, or more subdoses per day.

For preparing pharmaceutical compositions containing a Smad3 inhibitor, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component. In tablets, the active ingredient (an inhibitor of TGF-β/Smad3 signaling) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets may contain between about 5% to about 70% by weight of the active ingredient of an inhibitor of Smad3. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a Smad3 inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a Smad3 inhibitor) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a Smad3 signaling inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, for example from 5 to 9, or from 7 to 8.

The pharmaceutical compositions comprising a Smad3 inhibitor can be administered for prophylactic and/or therapeutic treatments. In therapeutic applications, compositions are administered to a patient already suffering from a condition that may be exacerbated by the TGF-β/Smad3 mediated cellular signaling in an amount sufficient to prevent, cure, reverse, or at least partially slow or arrest the symptoms of the condition and its complications, such as the onset, progression, and metastasis of certain types of cancer. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing a Smad3 inhibitor are administered to a patient susceptible to or otherwise at risk of developing a disease or condition in which excessive TGF-β/Smad3 mediated signaling is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of a Smad3 inhibitor sufficient to effectively inhibit cellular signaling mediated by Smad3 in the patient, either therapeutically or prophylactically.

Pharmaceutical Formulations

When used for pharmaceutical purposes, the Smad3 inhibitor may be generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. Biochemistry 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the compounds. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's Pharmaceutical Sciences, Mack Publishing Company, Philadelphia, Pa., 17th ed. (1985).

Administration of Formulations

The formulations containing a Smad3 inhibitor compound may be delivered to any tissue or organ using any delivery method known to the ordinarily skilled artisan. They may be formulated for subcutaneous, intramuscular, intravenous, intraperitoneal, or intratumor injection, or for oral ingestion or for topical application.

The formulations are typically administered to a cell. The cell may be provided as part of a tissue, such as an epithelial membrane, or as an isolated cell, such as in tissue culture. The cell can be provided in vivo, ex vivo, or in vitro.

The formulations may be introduced into the tissue of interest in vivo or ex vivo by a variety of methods. They may be introduced into cells by such methods as microinjection, calcium phosphate precipitation, liposome fusion, ultrasound, electroporation, or biolistics. They may be taken up directly by the tissue of interest, for example, when the targeted tissue is the skin.

The compounds or compositions may be administered ex vivo to cells or tissues explanted from a patient, then returned to the patient. Examples of ex vivo administration of therapeutic gene constructs include Nolta et al., Proc Natl. Acad. Sci. USA 93(6):2414-9 (1996); Koc et al., Seminars in Oncology 23(1):46-65 (1996); Raper et al., Annals of Surgery 223(2):116-26 (1996); Dalesandro et al., J. Thorac. Cardi. Surg., 11(2):416-22 (1996); and Makarov et al., Proc. Natl. Acad. Sci. USA 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of a compound to be administered, the physician should evaluate the particular compound being used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present disclosure, doses of compounds may range from about 0.1 µg-100 mg per patient as typical. Doses may generally range between about 0.01 and about 100 µg per kilogram of body weight, for example between about 0.1 and about 50 µg/kg of body weight.

The present disclosure provides pharmaceutical formulations or compositions, both for veterinary and for human medical use, which comprise one or more compounds of Formula 1 or Formula 2, or any embodiments thereof as described herein or any pharmaceutically acceptable salts thereof, with one or more pharmaceutically acceptable carriers and/or excipients, and optionally any other therapeutic ingredients, stabilisers, or the like.

The carrier(s) or excipients must be pharmaceutically acceptable in the sense of being compatible with the other ingredients sugar), hydroxyethylstarch (HES), dextrates (e.g., cyclodextrins, such as 2-hydroxypropyl-o-cyclodextrin and sulfobutylether-o-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), and in "Handbook of Pharmaceutical Excipients", Third Ed., Ed. A. H. Kibbe, Pharmaceutical Press, 2000.

Processes for Preparing the Smad3 Inhibitor Compounds

A process for preparing a compound of Formula 1a(i) or 1b(i) may comprise reacting a compound of Formula 6 with a compound of Formula 7:

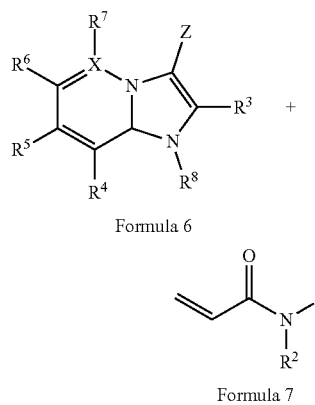

wherein $R^1$ to $R^8$ may be any embodiment of those groups as described herein, and Z is a leaving group, for example a halide group such as iodo.

The Smad3 inhibitor compounds may be prepared by processes according to any one of Schemes 1 to 4 as described below and herein.

Scheme 1: General Procedure for preparing Compounds with the Formula 1a(i) and 1b(i)

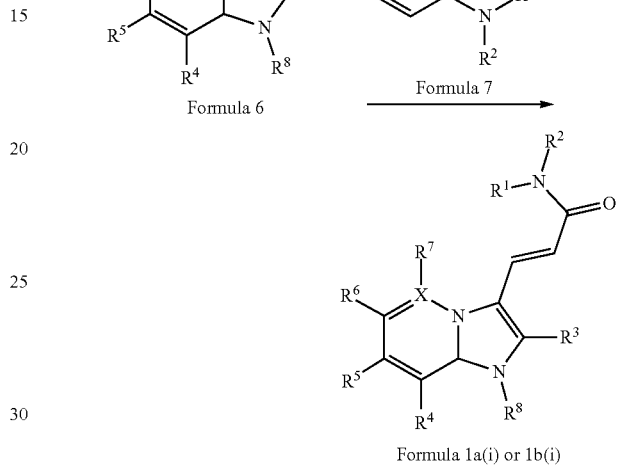

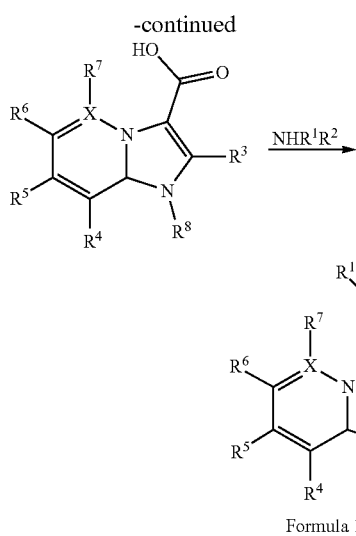

Formula 1a(ii)/1b(ii)

Scheme 3: General Procedure for preparing Compounds with the Formula 2a(i)

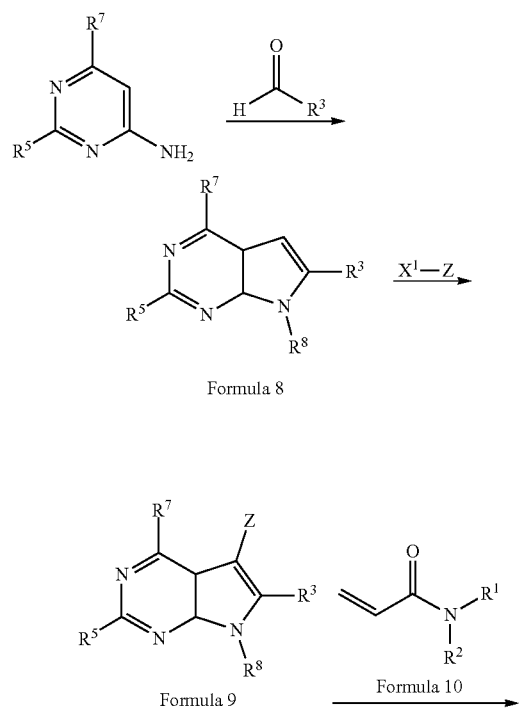

Formula 8

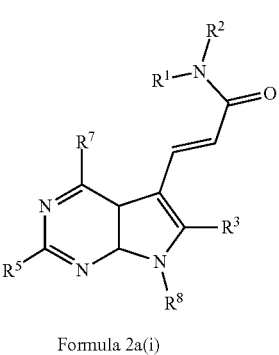

Formula 9       Formula 10

Scheme 4: General Procedure for preparing Compounds with the Formula 2a(ii)

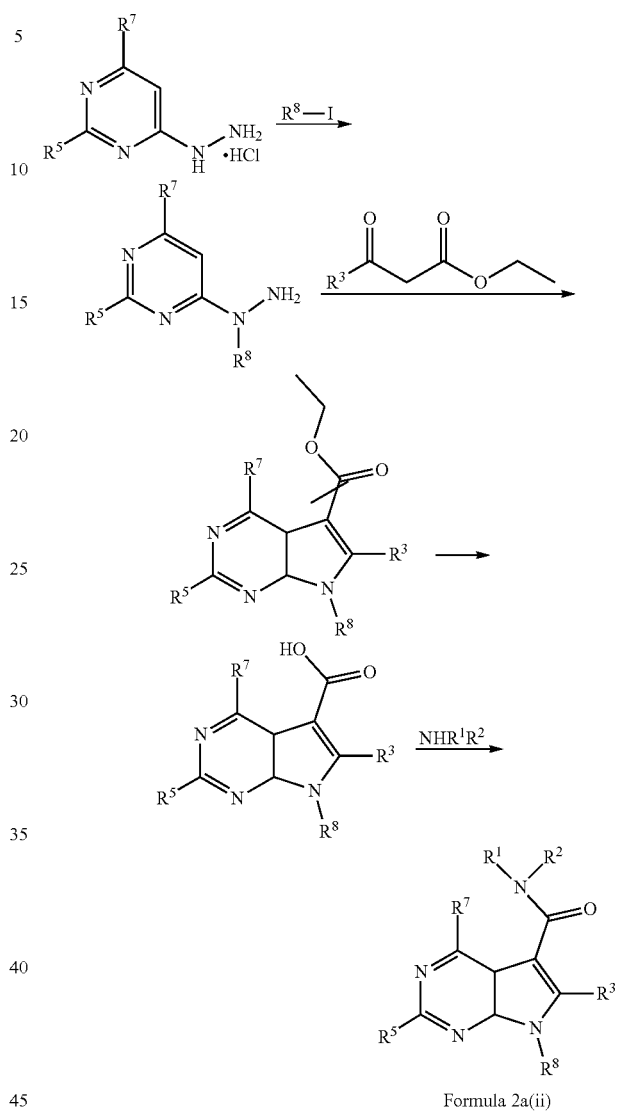

Formula 2a(ii)

It will be appreciated that processes, reagents and conditions described above are examples only, and other processes, reagents and conditions, may be used to prepare the Smad3 inhibitor compounds of the present disclosure.

Examples

The present disclosure is further described by the following examples. It is to be understood that the following description is for the purpose of describing particular embodiments only and is not intended to be limiting with respect to the above description.

A. General Synthetic Methods

Typically, reaction progress may be monitored by thin layer chromatography (TLC), IR, HPLC-MS, if desired. Intermediates and products may be purified by chromatography on silica gel, recrystallization, HPLC and/or reverse phase HPLC. Starting materials and reagents are either commercially available or may be prepared by one skilled in the art using methods described in the chemical literature and in the Examples provided below.

B. Preparation of Compounds of Formula 1a(i)

Preparation of a Compound of Formula 5a
(2-phenylimidazo[1,2-a]pyridine)

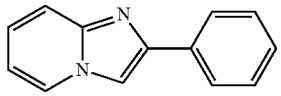

To a solution of 2-aminopyridine (2.0 g, 0.02 mol) in nitromethane (5.0 mL) was added benzaldehyde (2.5 g, 0.024 mol) and FeCl$_3$ (320 mg, 2 mmol) at room temperature. The solution was heated to 90° C. for 4 h. The solution was cooled to room temperature and water (10 mL) was added. The mixture was extracted with ethyl acetate (3×20 mL) and the combined organic layer was dried with Mg$_2$SO$_4$. The mixture was filtered and the filtrate concentrated in vacuo. The residue was purified by silica gel flash column chromatography with 20% ethyl acetate in hexane as the mobile phase, to afford 2-phenylimidazo[1,2-a]pyridine (2.3 g, 60%) as a white solid.
LCMS (ESMS): m/z: 195.3 (M$^+$+1).

Preparation of a Compound of Formula 6a
(3-iodo-2-phenyl-imidazo[1,2-a]pyridine)

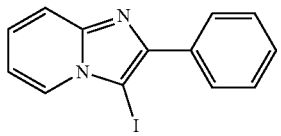 [SMILES: Ic1c(-c2ccccc2)nc2ccccn12]

To a solution of 2-phenylimidazo[1,2-a]pyridine (2.3 g, 0.01 mol) in DMF (15 mL) was added N-iodosuccinimide (2.7 g, 12 mmol) at room temperature. The solution was stirred at room temperature for 3 h. Water (30 mL) was added, and the solution was extracted with ethyl acetate (3×20 mL). The combined organic layer was dried with Mg$_2$SO$_4$. The mixture was filtered and the filtrate was concentrated in vacuo. The residue was purified by silica gel flash column chromatography with 10% ethyl acetate in hexane as the mobile phase, to afford 3-iodo-2-phenyl-imidazo[1,2-a]pyridine (2.6 g, 80%) as a white solid.
LCMS (ESMS): m/z: 321.9 (M$^+$+1).

Preparation of a Compound of Formula 7a (1-(6,7-dimethoxy-3,4-dihydroisoquinolin-2(1H)-yl)prop-2-en-1-one)

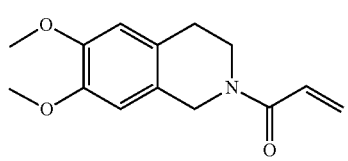 [SMILES: C=CC(=O)N1CCc2cc(OC)c(OC)cc2C1]

To a solution of 6,7-dimethoxy-1,2,3,4-tetrahydroisoquinoline (1.0 g, 5 mmol) in THF (10 mL) was added K$_2$CO$_3$ (1.4 g, 10 mmol) and acryloyl chloride (540 mg, 6 mmol) at room temperature. The mixture was heated at 50° C. for 3 h. The mixture was cooled and water (5 mL) was added. The mixture was extracted with ethyl acetate (3×15 mL) and the combined organic layer was dried with Mg$_2$SO$_4$. The mixture was filtered and the filtrate was concentrated in vacuo. The residue was purified by silica gel flash column chromatography with 20% ethyl acetate in hexane as the mobile phase to afford 1-(6,7-dimethoxy-3,4-dihydroisoquinolin-2(1H)-yl)prop-2-en-1-one (1.17 g, 95%) as a white solid.
LCMS (ESMS): m/z: 248.3 (M$^+$+1).

Preparation of a Compound of Formula 1a(i) ((E)-1-(6,7-dimethoxy-3,4-dihydroisoquinolin-2(1H)-yl)-3-(2-phenylimidazo[1,2-a]pyridin-3-yl)prop-2-en-1-one) (Compound 8)

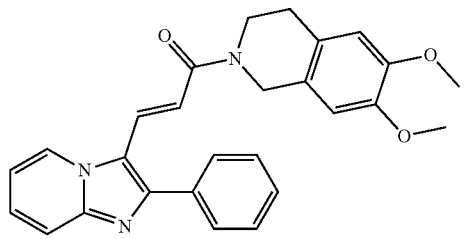 [SMILES: COc1cc2c(cc1OC)CN(C(=O)/C=C/c1c(-c3ccccc3)nc3ccccn13)CC2]

To a solution of 3-iodo-2-phenyl-imidazo[1,2-a]pyridine (50 mg, 0.16 mmol) in DMF (5 mL) was added 1-(6,7-dimethoxy-3,4-dihydroisoquinolin-2(1H)-yl)prop-2-en-1-one (46 mg, 0.19 mmol), Pd(OAc)$_2$ (3.5 mg, 0.02 mmol), tetrabutyl ammonium chloride (51.8 mg, 0.19 mmol) and K$_2$CO$_3$ (43 mg, 0.31 mmol) at room temperature. The mixture was heated at 100° C. for 12 h. The solution was cooled to room temperature and water (10 mL) was added. The mixture was extracted with ethyl acetate (3×10 mL) and the combined organic layer was dried with Mg$_2$SO$_4$. The mixture was filtered and the filtrate was concentrated in vacuo. The residue was purified by silica gel flash column chromatography with 50% ethyl acetate in hexane as the mobile phase to afford (E)-1-(6,7-dimethoxy-3,4-dihydroisoquinolin-2(1H)-yl)-3-(2-phenylimidazo[1,2-a]pyridin-3-yl)prop-2-en-1-one (Compound 8) (47 mg, 70%) as a white foam.
LCMS (ESMS): m/z: 440.1 (M$^+$+1).

C. Preparation of Compounds of Formula 1b(i)

Preparation of a Compound of Formula 5b
(2-phenylimidazo[1,2-b]pyridazine)

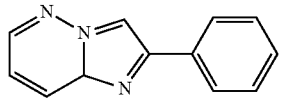

To a solution of 3-aminopyridazine (5.0 g, 0.05 mol) in ethanol (50 mL) was added NaHCO$_3$ (13.0 g, 0.16 mol) and 2-bromo-1-phenyl-ethanone (12.4 g, 0.06 mol) at room temperature. The mixture was heated under reflux for 12 h.

The solution was cooled to room temperature and the solvent was evaporated in vacuo. The residue was purified by silica gel flash column chromatography with 20% ethyl acetate in hexane as the mobile phase to afford 2-phenylimidazo[1,2-b]pyridazine (4.0 g, 40%) as a white solid.

LCMS (ESMS): m/z: 196.3 (M$^+$+1).

It will be appreciated that a compound of Formula 1b(i) may be prepared according to the process described above for compounds of Formula 1a(i).

D. Assay Methods

Materials

1. TGFβ/Smad Signaling Pathway SBE Reporter—HEK293 Cell Line BPS Bioscience Catalog #: 60653
2. Human TGFβ1 (BPS Bioscience #90900-1)
3. SIS3 (Sigma #S0447): inhibitor of TGFβ pathway. Prepare stock soln. in DMSO
4. Growth medium: MEM medium (Invitrogen #11095-080)+10% FBS (ATCC #30-2020)+1% non-essential amino acids (Lonza #13-114E)+1 mM Na pyruvate (Lonza #13-115E)+1% Penicillin/Streptomycin (ATCC #30-2300)+400 μg/ml of Geneticin (Invitrogen #11811-031)
5. Assay medium: MEM medium+0.5% FBS+1% non-essential amino acids+1 mM Na pyruvate+1% Pen/Strep
6. 96-well tissue culture-treated white clear-bottom assay plate (Corning #3610)
7. ONE-Step™ Luciferase Assay System (BPS, Cat. #60690)

Method

SBE reporter-HEK293 cells were harvested from culture in growth medium and seeded at a density of ~10,000 cells per well into a white clear-bottom 96-well microplate in 100 μl of assay medium. The plate containing cells was incubated at 37° C. in a CO$_2$ incubator. 24 h after seeding, cells were washed with 100 μL of assay buffer and treated with three-fold serial dilution of compounds in 50 μl assay medium. Cells were incubated at 37° C. in a CO$_2$ incubator for 4 h. For control wells, 50 μl assay medium was added with no inhibitor. Each treatment was performed in triplicate. After 4 h of incubation, 5 μl of human TGFβ1 in assay medium was added to cells (final TGFβ1 concentration=20 ng/ml). 5 μl of assay medium was added to the unstimulated control wells (for determining the basal activity). The plate with cells was incubated at 37° C. in CO$_2$ incubator overnight (~18 h).

After 18 h of incubation, Luciferase assay was performed using ONE-Step™ Luciferase Assay System according to the protocol provided: 50 μl of ONE-Step™ Luciferase reagent was added per well and shook at room temperature for ~10 min. Luminescence was measured using a luminometer. Compound 8 (Mw 439.5) was shown to be soluble in DMSO and had an IC$_{50}$ (μM) of 3.531, which compares favourably to the SIS3 compound IC$_{50}$ (μM) of 2.963.

1. In Vivo Syngeneic Model

In order to evaluate the in vivo efficacy of SIS3 and novel compounds of the present invention, a study has been conducted in treatment of the subcutaneous B16-F10 syngeneic models.

The compounds used in the study are SIS3 and Compound 8 referred to above and as described with respect to the present invention, as test articles. Compound 8 is referred to hereinafter as MO-00005.

1.1 Study Materials

1.1.1 Test Articles

The following are the particulars of the test articles as used in the in vivo syngeneic model:

| Test article name 1: | SIS3 (HCL salt) |
|---|---|
| Physical description: | Yellow powder |
| Storage conditions: | 25° C. |
| Amount: | 500 mg |
| Purity: | 98% |
| Molecular Weight: | 453.5 |

| Test article name 2: | MO-00005 |
|---|---|
| Physical description: | Yellow Foam |
| Storage conditions: | 25° C. |
| Amount: | 1,300 mg |
| Purity: | 98% |
| Molecular Weight: | 439.5 |

1.1.2 Vehicle Information

| Vehicle name: | DMSO |
|---|---|
| Supplier: | Sigma |
| Action: | Vehicle |
| Physical description: | Transparent liquid |
| Storage conditions: | Room temperature |
| Stability: | 3 years |
| Cat No.: | N/A |
| Purity: | 99% |

| Vehicle name: | PEG 300 |
|---|---|
| Supplier: | Sinopharm Chemical Reagent |
| Action: | Vehicle |
| Physical description: | Transparent liquid |
| Storage conditions: | Room temperature |
| Stability: | N/A |
| Cat No.: | 30150728 |
| Purity: | N/A |

| Vehicle name: | Polysorbate 80 |
|---|---|
| Supplier: | SIGMA |
| Action: | Vehicle |
| Physical description: | Transparent liquid |
| Storage conditions: | Room temperature |
| Stability: | N/A |

-continued

| Vehicle name: | Polysorbate 80 |
| --- | --- |
| Cat No.: | 3CBM6513V |
| Vehicle name: | PBS |
| Supplier: | Corning cellgro |
| Action: | Vehicle |
| Storage conditions: | 4° C. |
| Cat No.: | 21-040-CVR |

1.1.3 Reagent

The following reagents were used
DMEM Medium: Corning cellgro, Cat No.: R10-013-CV
FBS: GIBCO, Cat No.: 10270-106
PBS: Corning cellgro, Cat No.: 21-040-CVR
Trypsin-EDTA: GIBCO, REF: 25200-072
Penicillin-Streptomycin: GIBCO, REF: 15140-122

1.2 Animals and Feeding

1.2.1 Animals

Animal species and strain: $C_{57}BL/6$ mice
History of treatment: Naive
Sex, age and weight: Female, 6-8 weeks
Breeder/supplier: Shanghai SLAC Laboratory Animal Co. Ltd
Adaptation: At least 7 days
Room: SPF Room
Room temperature: 20-26° C.
Room relative humidity: 40-70%
Light cycle: Fluorescent light for 12-hour light (08:00-20:00) and 12-hour dark
Animal hosting: 2-5 mice/cage each group
Food: Free access to food
Water: Free access to water (municipal tap water filtered by reverse osmosis or high-pressure sterilizer)

A total of 120 $C_{57}BL/6$ mice were used in this study (30 mice were used as spares). The animals were specific pathogen free and approximately 6-8 weeks old upon arrival at testing laboratories.

1.2.2 Animal Environment

The room was supplied for housing with HEPA filtered air at the rate of 15-25 air changes per hour. The temperature was maintained at 20-26° C. (68-79° F.) with a relative humidity of 40-70%. Temperature and humidity were continuously monitored and recorded. Illumination were fluorescent light for 12-hour light (08:00-20:00) and 12-hour dark.

1.2.3 Food and Water

Animals had ad libitum access to rodent food.
Water, from the municipal water supply, was filtered by reverse osmosis or high-pressure sterilizer adjusted to pH 2-3 with HCl.

1.3 Experimental Procedures

1.3.1 Cell Culture

B16-F10 cell was maintained at 37° C. under 5% $CO_2$ in DMEM medium supplemented with 10% FBS and were subsequently cultured within 10 passages before inoculated into the mice.

One day before cell harvest for implantation, 25% fresh culture medium was added to the culture flask to keep the cell grow in log phase. At the harvest day, the confluence of the cultured cell should not be less than 70% or exceed 90%.

1.3.2 Grouping

B16-F10 cells ($3\times10^5$ in 100 μL of serum-free medium) were inoculated to each of $C_{57}BL/6$ mice via s.c. under anesthesia by 3-4% isoflurane. 1 days after inoculation, mice were randomized based on body weight into 5 groups (group 1-5) shown in Table 1. Each group contains 15 mice.

When average tumor volume reached 35-60 $mm^3$, 15 mice were randomized into group 6. The day of inoculation was denoted as day 0.

TABLE 1

| Study design of efficacy study for B16-F10 | | | | |
| --- | --- | --- | --- | --- |
| Group | N | Test Articles | Dose (mg/kg) | Dosing Regime |
| 1 | 15 | Vehicle (2% DMSO + 30% PEG300 +2% Tween80 + $H_2O$) | N/A | i.p. QD*3 weeks |
| 2 | 15 | SIS3 | 10 | i.p. QD*3 weeks |
| 3 | 15 | SIS3 | 30 | i.p. QD*3 weeks |
| 4 | 15 | MO-00005 | 10 | i.p. QD*3 weeks |
| 5 | 15 | MO-00005 | 30 | i.p. QD*3 weeks |
| 6 | 15 | MO-00005 | 100 | i.p. QD*3 weeks |

N: animal number per group
Dosing volume: adjust dosing volume based on body weight (10 uL/g)

1.3.2 Testing Article Dosing Solution Preparation

TABLE 2

| Formulation and Storage | | | | |
| --- | --- | --- | --- | --- |
| Compound | Preparation instruction | Concentration (mg/mL) | Storage condition | Preparation Frequency |
| SIS3 | 50 mg/mL SIS3 stock solution were prepared at the beginning of the study. 0.04 mL 25 mL stock solution were diluted in 0.6 ml PEG, 0.04 mL Tween 80 and 1.32 mL PBS | 1 | 4° C. | Freshly prepared |
| SIS3 | 150 mg/mL SIS3 stock solution were prepared at the beginning of the study. 0.04 mL 25 mL stock solution were diluted in 0.6 ml PEG, 0.04 mL Tween 80 and 1.32 mL PBS | 3 | 4° C. | Freshly prepared |
| MO00005 | 50 mg/mL MO-0005 stock solution were prepared at the beginning of the study. 0.04 mL 25 mL stock solution were diluted in 0.6 ml PEG, 0.04 mL Tween 80 and 1.32 mL PBS | 1 | 4° C. | Freshly prepared |

TABLE 2-continued

Formulation and Storage

| Compound | Preparation instruction | Concentration (mg/mL) | Storage condition | Preparation Frequency |
|---|---|---|---|---|
| MO00005 | 150 mg/mL MO-0005 stock solution were prepared at the beginning of the study. 0.04 mL 25 mL stock solution were diluted in 0.6ml PEG, 0.04 mL Tween 80 and 1.32 mL PBS | 3 | 4° C. | Freshly prepared |
| MO00005 | 50 mg/mL MO-0005 stock solution were prepared at the beginning of the study. 0.04 mL 25 mL stock solution were diluted in 0.6 ml PEG, 0.04 mL Tween 80 and 1.32 mL PBS | 10 | 4° C. | Freshly prepared |

1.3.2 Body Weight Measurements

Body weight was measured on Day 4, 5, 6, 8, 11, 13, 15 and 18 after inoculation. When required, body weight was measured daily.

1.3.3 Tumor Volume Measurement

Tumor dimensions were measured on Day 4, 5, 6, 8, 11, 13, 15 and 18, after inoculation in 2 dimensions with calipers.

When required, tumor volume was measured daily. The tumor volume (V) was calculated as follows: $V = (length \times width^2)/2$.

The individual relative tumor volume (RTV) was calculated as follows: $RTV = V_t/V_0$, where $V_t$ was the volume on each day, and $V_0$ was the volume at the beginning of the treatment.

Tumor growth inhibition (TGI), $TGI = (1 - (T_i - T_0)/(C_i - C_0)) \times 100\%$; $T_i$ and $C_i$ as the mean tumor volumes of the treatment and control groups on the measurement day; $T_0$ and $C_0$ as the mean tumor volumes of the treatment and control groups on day 0

1.4 Statistics

Results were expressed as mean±S.E.M. Comparisons between two groups were made by Dunnett's multi-comparison test, $p < 0.05$ were considered as significant.

1.5 Results

1.5.1 Body Weight and Clinical Observations

Figure 3:
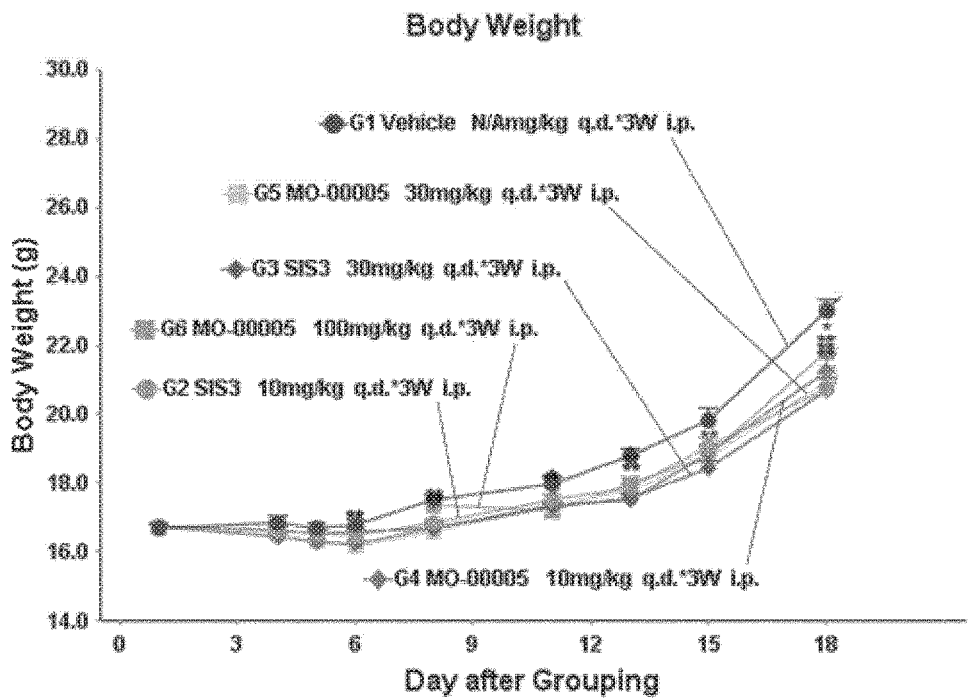
FIG. 3 shows body weights of mice in different groups during a B16-F10 syngeneic model.

The results of body weights in the tumor bearing mice were shown in FIG. 3 and Table 3.

TABLE 3

Body weight (g) of Mice in Different Groups

| Day | G1 Vehicle N/Amg/kg q.d. * 3W i.p. | | G2 SIS3 10 mg/kg q.d. * 3W i.p. | | | G3 SIS3 30 mg/kg q.d. * 3W i.p. | | | G4 MO-00005 10 mg/kg q.d. * 3W i.p. | | | G5 MO-00005 30 mg/kg q.d. * 3W i.p. | | | G6 MO-00005 100 mg/kg q.d. * 3W i.p. | | |
|---|---|---|---|---|---|---|---|---|---|---|---|---|---|---|---|---|---|
| | Mean | SEM | Mean | SEM | P Value | Mean | SEM | P Value | Mean | SEM | P Value | Mean | SEM | P Value | Mean | SEM | P Value |
| 1 | 16.69 | 0.09 | 16.72 | 0.09 | 1.00 | 16.72 | 0.08 | 1.00 | 16.73 | 0.09 | 0.99 | 16.70 | 0.09 | 1.00 | N/A | N/A | N/A |
| 4 | 16.85 | 0.20 | 16.64 | 0.13 | 0.81 | 16.66 | 0.10 | 0.83 | 16.41 | 0.11 | 0.19 | 16.54 | 0.09 | 0.44 | N/A | N/A | N/A |
| 5 | 16.67 | 0.19 | 16.55 | 0.13 | 0.97 | 16.55 | 0.10 | 0.95 | 16.26 | 0.12 | 0.22 | 16.32 | 0.08 | 0.30 | N/A | N/A | N/A |
| 6 | 16.78 | 0.16 | 16.50 | 0.13 | 0.36 | 16.59 | 0.11 | 0.67 | 16.21 | 0.13 | 0.01 | 16.18 | 0.09 | 0.00 | N/A | N/A | N/A |
| 8 | 17.50 | 0.16 | 16.83 | 0.11 | 0.00 | 16.69 | 0.12 | 0.00 | 16.67 | 0.11 | 0.00 | 16.60 | 0.14 | 0.00 | 17.36 | 0.17 | 0.93 |
| 11 | 17.99 | 0.17 | 17.53 | 0.14 | 0.12 | 17.30 | 0.12 | 0.01 | 17.33 | 0.14 | 0.01 | 17.36 | 0.14 | 0.02 | 17.20 | 0.17 | 0.00 |
| 13 | 18.78 | 0.20 | 17.84 | 0.14 | 0.00 | 17.53 | 0.14 | 0.00 | 17.51 | 0.22 | 0.00 | 17.78 | 0.18 | 0.00 | 17.95 | 0.23 | 0.01 |
| 15 | 19.82 | 0.36 | 19.04 | 0.27 | 0.30 | 18.45 | 0.19 | 0.01 | 18.85 | 0.27 | 0.13 | 18.73 | 0.27 | 0.07 | 18.78 | 0.24 | 0.08 |
| 18 | 23.01 | 0.28 | 20.77 | 0.44 | 0.00 | 20.70 | 0.33 | 0.00 | 21.26 | 0.51 | 0.02 | 20.93 | 0.50 | 0.00 | 21.82 | 0.42 | 0.19 |

1.5.2 Tumor Volume (TV) and Relative Tumor Volume (RTV)

Figure 4:
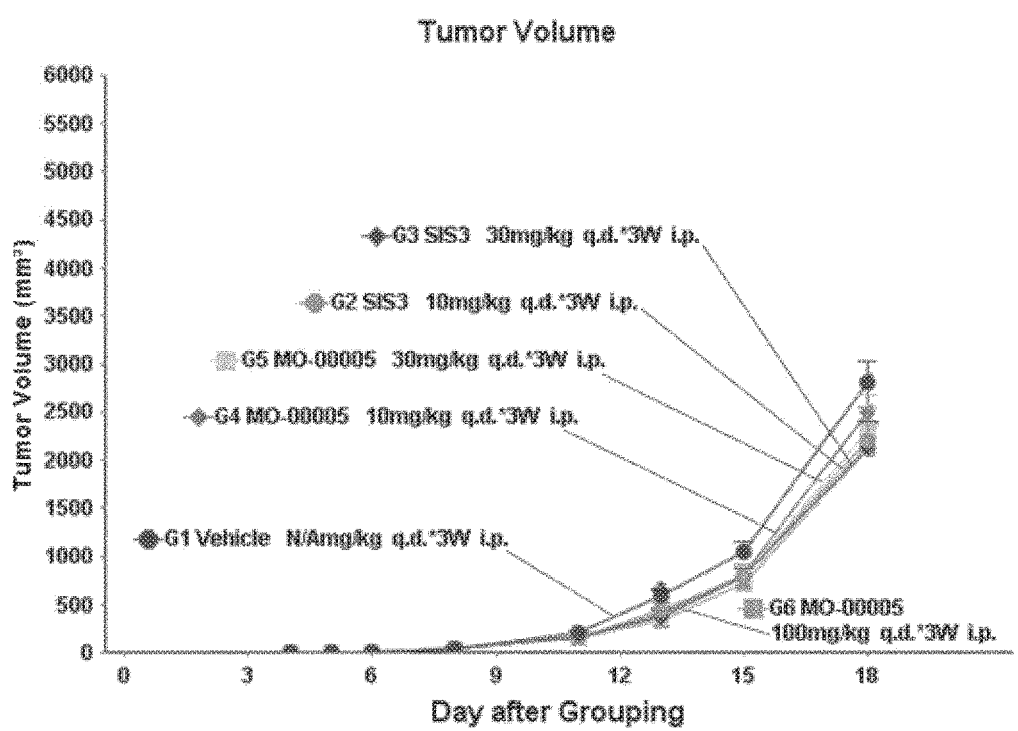
FIG. 4 shows tumor sizes of mice in different groups during the B16-F10 syngeneic model.
Figure 5:
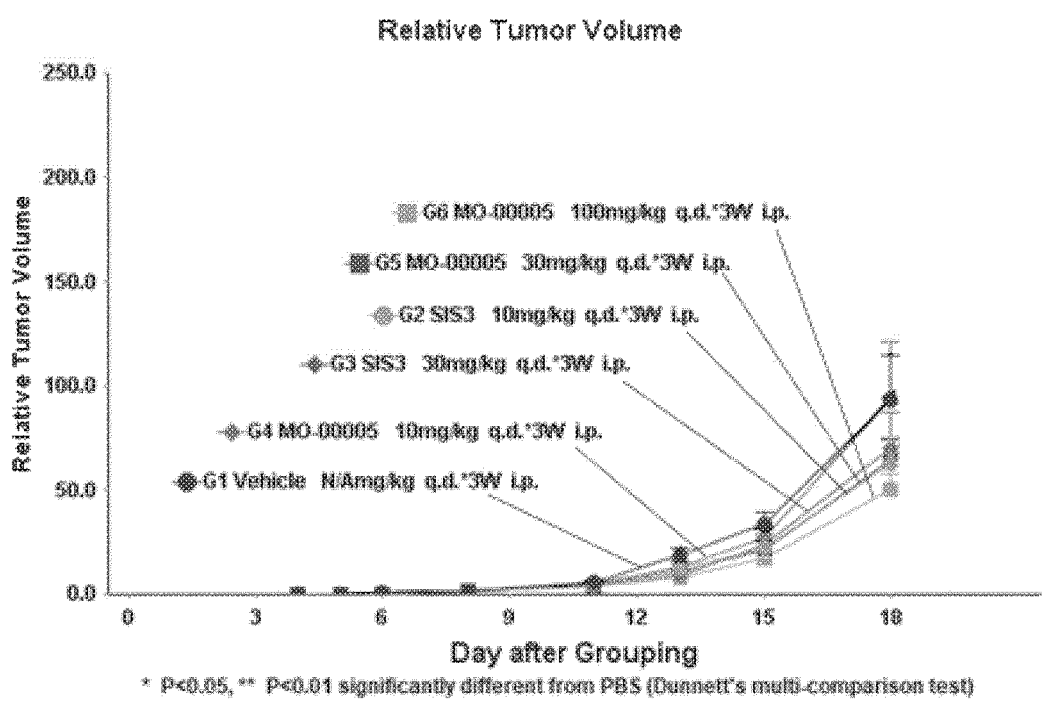
FIG. 5 shows the relative tumor volume of mice in different groups during the B16-F10 syngeneic model.

The tumor sizes of the different groups at different time points are shown in FIG. 4 and Table 4. The relative tumor volume at different time points were shown in FIG. 5 and Table 5.

TABLE 4

Tumor Sizes in the Different Treatment Groups (mm3)

| | G1 Vehicle N/Amg/kg q.d. * 3W i.p. | | G2 SIS3 10 mg/kg q.d. * 3W i.p. | | | G3 SIS3 30 mg/kg q.d. * 3W i.p. | | |
|---|---|---|---|---|---|---|---|---|
| Day | Mean | SEM | Mean | SEM | P Value | Mean | SEM | P Value |
| 4 | 0.95 | 0.43 | 0.87 | 0.35 | 1.00 | 0.28 | 0.14 | 0.31 |
| 5 | 1.29 | 0.49 | 1.10 | 0.41 | 0.99 | 0.46 | 0.19 | 0.27 |
| 6 | 5.33 | 1.49 | 3.36 | 0.58 | 0.32 | 3.44 | 0.53 | 0.36 |
| 8 | 47.04 | 8.34 | 43.65 | 6.95 | 1.00 | 49.16 | 8.18 | 1.00 |
| 11 | 206.00 | 23.42 | 156.77 | 24.38 | 0.45 | 163.60 | 28.56 | 0.67 |
| 13 | 589.86 | 60.00 | 443.17 | 67.88 | 0.35 | 379.84 | 57.13 | 0.05 |
| 15 | 1051.65 | 99.43 | 793.01 | 124.58 | 0.25 | 786.37 | 99.57 | 0.23 |
| 18 | 2805.36 | 217.66 | 2209.13 | 342.75 | 0.50 | 2131.42 | 267.02 | 0.40 |

| | G4 MO-00005 10 mg/kg q.d. * 3W i.p. | | | G5 MO-00005 30 mg/kg q.d. * 3W i.p. | | | G6 MO-00005 100 mg/kg q.d. * 3W i.p. | | |
|---|---|---|---|---|---|---|---|---|---|
| Day | Mean | SEM | P Value | Mean | SEM | P Value | Mean | SEM | P Value |
| 4 | 0.62 | 0.25 | 0.84 | 0.36 | 0.16 | 0.42 | N/A | N/A | N/A |
| 5 | 0.75 | 0.28 | 0.64 | 0.56 | 0.25 | 0.38 | N/A | N/A | N/A |
| 6 | 4.31 | 0.61 | 0.83 | 5.33 | 0.76 | 1.00 | N/A | N/A | N/A |
| 8 | 38.42 | 5.25 | 0.85 | 47.99 | 7.58 | 1.00 | 42.19 | 0.78 | 0.97 |
| 11 | 151.84 | 18.92 | 0.26 | 165.30 | 32.37 | 0.76 | 155.10 | 11.19 | 0.19 |
| 13 | 416.04 | 47.32 | 0.10 | 376.62 | 47.80 | 0.03 | 335.85 | 30.71 | 0.00 |
| 15 | 816.24 | 77.40 | 0.33 | 794.11 | 119.61 | 0.25 | 724.03 | 70.93 | 0.09 |
| 18 | 2500.45 | 309.87 | 0.93 | 2303.09 | 370.07 | 0.66 | 2107.22 | 288.72 | 0.37 |

TABLE 5

Relative tumor volume Mice in Different Groups

| | G1 Vehicle N/Amg/kg q.d. * 3W i.p. | | G2 SIS3 10 mg/kg q.d. * 3W i.p. | | | G3 SIS3 30 mg/kg q.d. * 3W i.p. | | | G4 MO-00005 10 mg/kg q.d. * 3W i.p. | | | G5 MO-00005 30 mg/kg q.d. * 3W i.p. | | | G6 MO-00005 100 mg/kg q.d. * 3W i.p. | | |
|---|---|---|---|---|---|---|---|---|---|---|---|---|---|---|---|---|
| Day | Mean | SEM | Mean | SEM | P Value | Mean | SEM | P Value | Mean | SEM | P Value | Mean | SEM | P Value | Mean | SEM | P Value |
| 4 | 0.02 | 0.01 | 0.04 | 0.02 | 0.78 | 0.01 | 0.00 | 0.28 | 0.04 | 0.02 | 0.91 | 0.01 | 0.00 | 0.12 | | | |
| 5 | 0.03 | 0.01 | 0.05 | 0.02 | 0.86 | 0.01 | 0.01 | 0.23 | 0.04 | 0.02 | 0.95 | 0.01 | 0.00 | 0.09 | | | |
| 6 | 0.16 | 0.04 | 0.12 | 0.03 | 0.81 | 0.12 | 0.03 | 0.81 | 0.19 | 0.06 | 0.96 | 0.16 | 0.03 | 1.00 | | | |
| 8 | 1.00 | 0.00 | 1.00 | 0.00 | | 1.00 | 0.00 | | 1.00 | 0.00 | | 1.00 | 0.00 | | 1.00 | 0.00 | |
| 11 | 5.69 | 0.71 | 4.07 | 0.66 | 0.25 | 3.98 | 0.66 | 0.20 | 4.80 | 0.83 | 0.77 | 3.76 | 0.42 | 0.12 | 3.70 | 0.29 | 0.11 |
| 13 | 18.33 | 3.69 | 12.20 | 2.41 | 0.50 | 9.22 | 1.29 | 0.09 | 12.93 | 2.47 | 0.62 | 10.44 | 1.68 | 0.20 | 7.98 | 0.76 | 0.03 |
| 15 | 33.19 | 6.27 | 22.19 | 4.49 | 0.47 | 23.71 | 5.25 | 0.66 | 26.76 | 4.74 | 0.88 | 21.61 | 3.76 | 0.37 | 17.31 | 1.81 | 0.07 |
| 18 | 93.16 | 21.19 | 62.21 | 12.29 | 0.57 | 70.14 | 17.45 | 0.81 | 93.48 | 27.25 | 1.00 | 63.87 | 10.35 | 0.62 | 50.47 | 7.14 | 0.29 |

1.5.3 Tumor Growth Inhibition (TGI)

Tumor growth inhibition (TGI), TGI=(1−(Ti−T0)/(Ci−C0))×100%; Ti and Ci as the mean tumor volumes of the treatment and control groups on the measurement day; T0 and C0 as the mean tumor volumes of the treatment and control groups on day 0. TGI=(1−(Ti−T0)/(Ci−C0))×100%. The TGI of the different groups at different time points were shown in Table 6.

TABLE 6

Tumor growth inhibition (%) in different groups

| | G1 Vehicle N/Amg/kg q.d. * 3W i.p. | G2 SIS3 10 mg/kg q.d. * 3W i.p. | | G3 SIS3 30 mg/kg q.d. * 3W i.p. | | G4 MO-00005 10 mg/kg q.d. * 3W i.p. | | G5 MO-00005 30 mg/kg q.d. * 3W i.p. | | G6 MO-00005 100 mg/kg q.d. * 3Wi.p. | |
|---|---|---|---|---|---|---|---|---|---|---|---|
| Day | Mean | Mean | TGI | Mean | TGI | Mean | TGI | Mean | TGI | Mean | TGI |
| 4  | 0.95    | 0.87    | N/A | 0.28    | N/A | 0.62    | N/A | 0.36    | N/A | N/A     | N/A |
| 5  | 1.29    | 1.1     | N/A | 0.46    | N/A | 0.75    | N/A | 0.56    | N/A | N/A     | N/A |
| 6  | 5.33    | 3.36    | N/A | 3.44    | N/A | 4.31    | N/A | 5.33    | N/A | N/A     | N/A |
| 8  | 47.04   | 43.65   | N/A | 49.16   | N/A | 38.42   | N/A | 47.99   | N/A | 42.19   | N/A |
| 11 | 206     | 156.77  | 29% | 163.6   | 28% | 151.84  | 29% | 165.3   | 26% | 155.1   | 29% |
| 13 | 589.86  | 443.17  | 26% | 379.84  | 39% | 416.04  | 30% | 376.62  | 39% | 335.85  | 46% |
| 15 | 1051.65 | 793.01  | 25% | 786.37  | 27% | 816.24  | 23% | 794.11  | 26% | 724.03  | 32% |
| 18 | 2805.36 | 2209.13 | 21% | 2131.42 | 25% | 2500.45 | 11% | 2303.09 | 18% | 2107.22 | 25% |

Note:
The TGI is calculated based on tumor volume of Day 8, since tumor volume before Day 8 is estimated value.

Note: The TGI is calculated based on tumor volume of Day 8, since tumor volume before Day 8 is estimated value.

1.6 Results Summary and Discussion

In this study, the efficacy of the test article was evaluated in the treatment of B16-F10 syngeneic model in female $C_{57}BL/6$ mice.

The test compound SIS3 as single agent treatment at 10 mg/kg and 30 mg/kg showed anti-tumor response as compared with vehicle treatment with TGI, and significant efficacy on tumor weight, with dose response. MO-00005 as single agent treatment at 10 mg/kg, 30 mg/kg and 100 mg/kg produced anti-tumor response as compared with vehicle treatment with TGI with dose response; and significant efficacy on tumor weight, with dose response.

In summary, the test compound SIS3 and MO-00005, as single agent treatment with the dosing schedule, produced significant anti-tumor activity against the B16-F10 syngeneic model with dose response in this study.

This animal efficacy proof of concept (POC) model has been performed for the effect of compound (MO-00005) as a single agent in cancer treatment. In this experimental, the cancer inhibition effect of MO-00005 was evaluated in an mice melanoma syngeneic model.

The result demonstrated that MO-00005 inhibits the growth of cancer with doses of 10, 30 and 100 mg per kg. The effect is also dose dependent.

An approximate 50% reduction of tumor weight compared to the control group, was observed after 18 days of the experiment for the high dose group.

The results demonstrated the usefulness of the present invention for both prophylactic and advanced tumor treatment.

2. Aqueous Solubility Assay

2.1 Objective

Poorly soluble compounds can dramatically reduce productivity in drug discovery and development. Solubility assays involve assessment of kinetic solubility (from DMSO stock solution) using a shake-flask technique in a plate format and LC/MS/MS analysis.

Solubility information helps in interpreting results from other in vitro assays, recognizing compounds that are solubility limited, and prioritizing compounds for further development.

2.2 Materials and Methods

2.2.1 Test Article

The compounds used in the study are SIS3 and Compound 8 referred to above and as described with respect to the present invention, as test articles.

Compound 8 is referred to hereinafter as MO-00005.

SIS3 and M00005 are basic compounds. SIS3 is supplied as the hydrochloride salt, and M00005, which is compound 8 referred to above, is supplied as the free base.

2.2.2 HPLC System

Pump: Agilent 1200 Quaternary Pump
Autosampler: Agilent 1200
Column thermostat: Agilent 1200

2.2.3 MS System

Detector: Sciex API-3000 Mass Spectrometer,
Data System: Analyst Version ver. 1.6.2 All LC components were controlled by the Analyst software.
Data Acquisition: Computer Dell Optiplex 755 with Windows XP Professional.
Result tables processed using Excel 2010

2.2.4 Chromatographic Conditions

Analytical Column: YMC ODS-AM S-3 120A, 3×50 mm column with Guard.
Flow Rate: 500 ul/min
Mobil Phase: Isocratic 50% acetonitrile: 50% 20 mM Ammonium Acetate pH 4. Back Pressure: 1400 psi
Column Temperature: Ambient,
Autosampler Setting: Injection Volume: 5 ul, Loop Volume: 100 ul, Tray Temperature: 4° C.
Needle wash: Vial position 100. Needle wash solution: 50% Methanol water

2.2.5 Mass Spectrometer Conditions

Ion Source: TurboIonspray™
Nebulizer gas: Nitrogen setting 10
Auxiliary gas: Air at 4/min flow rate, 4050° C.

CAD gas: Nitrogen at setting 3
Curtain gas: Nitrogen at setting 8
IonSpray Voltage: 5200

2.2.6 Lens Voltage

Declustering Potential (DP): 30, Focusing Potential (FP): 200; Entrance Potential (EP): 10
Collision Cell Ext Potential (CXP): 15
Compound dependent: Collision Energy (CE) volts, M01: 30, M05:40
Scan Mode: Positive Ion—MRM
Settings Q1 and Q3 set to unit resolution
Channels (Q1→Q3) m/z:
SIS3:454→261
M00005: 440→247

2.2.6 Retention Times

SIS3: 2.5 min, M00005: 0.82 min

2.2.7 Buffer Preparation Instruction (100 mM Buffering Capacity)

Unbuffered DI water: Check the Conductivity of the DI water, Conductivity should be less than 50 microSieverts

2.2.8 Carbonate Buffer pH 10.0 (30 mL)

Component Mass Molarity
Sodium bicarbonate (mw: 84 g/mol) 0.11628 g 0.0461 M
Sodium carbonate (anhydrous) (mw: 106 g/mol) 0.17127 g 0.0539 M
Tris Buffer pH 7.7 (100 mL)
Add 0.363 g of tris to 30 mL water. Check pH at room temperature the pH should be 7.7 with acetic acid.

Acetate Buffer pH 3.6 (30 mL)
Component Mass Molarity
Sodium Acetate (anhydrous) (mw: 82 g/mol) 0.01188 g 0.0048 M
Acetic Acid (mw: 60.05 g/mol) 0.17145 g 0.0952 M (0.17145 g=0.17145 ul)

2.2.9 Solubility Evaluation Procedure

Solubility experiments were run overnight (24 hours) in jitterbug shaker, and the following steps used:
(i) Start the Jitterbug incubator shaker and set temperature to 25° C.
(ii) Prepare buffers at 3 levels pH 3.6, pH 7.7, pH 10 (100 mM) and also DI water.
(iii) Buffer preparation for each pH level is given below.
(iv) Weigh approx. 3 mg of each compound into 1 mL autosampler vials (4 vials for each compound.
(v) Add 1 mL of water to first vial, 1 mL of the various buffers to each of the other vials.
(vi) Load into shaker and set timer for 24 hours
(vii) Prepare standard solutions in the range 1 ug/mL to 5 ng/mL and keep them out at the same temperature as the solubility samples
(viii) Remove vials, transfer contents to Eppendorf and centrifuge at 14K rpm for 5-10 mins.
(ix) Transfer clear solution to autosampler vials and dilute as necessary to fall within calibration range.
(x) Assay samples—test one sample with an initial dilution of 1:1000 if signal is too high, continue diluting sample until it is within calibration range. Then run all samples at this dilution.
(xi) Run samples in duplicate and estimate aqueous solubility.

2.3 Results and Discussion

Both SIS3 and M00005 are basic compounds. SIS3 is supplied as the hydrochloride salt, and M00005 is supplied as the free base.

As such, it may be expected that the hydrochloride salt will have better solubility in unbuffered aqueous solutions. There the thermodynamic equilibrium dissolution concentrations of both compounds were determined also in buffered solutions at pH 4, 7.7, and 10.4 in addition to unbuffered water. Results for SIS3 are shown in Table 7 below.

TABLE 7

| Sample Name | Peak1 | Peak2 | Peak3 | Total | Conc. (ng/mL) | Dilution Factor | Conc. Of Sample (ug/mL) |
|---|---|---|---|---|---|---|---|
| SIS3 in water | 3.94E+04 | 8.86E+04 | 7.17E+04 | 2.00E+05 | 1767.81 | 10.00 | 17.7 |
| SIS3 pH 4.03 | 4.53E+04 | 7.54E+04 | 7.38E+04 | 1.95E+05 | 1721.83 | 10.00 | 17.2 |
| SIS3 pH 7.70 | 4.01E+03 | 4.00E+04 | 3.47E+04 | 7.87E+04 | 698.14 | 10.00 | 7.0 |
| SIS3 pH 10.63 | 0.00E+00 | 1.43E+04 | 1.22E+04 | 2.65E+04 | 236.55 | 10.00 | 2.4 |

The data shows that solubility of SIS3 decreases with higher pH as would be expected for a basic compound. The solubility in unbuffered water is similar to that at pH 4.03 because the free base has been neutralized as the hydrochloride salt.

The results for MO-00005 are shown in Table 8 below.

TABLE 8

| Sample Name | Analyte Peak Area (counts) | Calculated Conc. (ng/mL) | Dilution factor | Conc. Of sample (ug/mL) |
|---|---|---|---|---|
| MO0005 water sol | 3.34E+05 | 321 | 1000 | 321 |
| MO0005 pH 4.03 | 6.19E+05 | 598 | 1000 | 598 |
| MO0005 pH 7.7 | 2.81E+05 | 269 | 1000 | 269 |
| MO0005 pH 10.63 | 2.92E+05 | 280 | 1000 | 280 |

The data shows that solubility of MO-0005 decreases with higher pH as would be expected for a basic compound.

The solubility in unbuffered water much lower to that at pH 4.03 because it is the free base.

2.4 Conclusions and Inferences

Based on the result, the aqueous solubility of MO-0005 is 35 times the solubility of SIS3 at a pH of 4.0 (598 ug/mL vs 17.2 ug/mL).

At pH 10.63, the aqueous solubility of MO-0005 is 117 times the solubility of SIS3 (280 ug/mL vs 2.4 ug/mL).

The overall conclusion is that M00005 has supplier aqueous solubility to SIS3 at different pH.

This will have profound advantage for M00005 over SIS3 on further drug development and clinical applicability.

3. Cytochrome P450 (CYP) Inhibition Assay

3.1 Objectives

Cytochrome P450 (CYP) inhibition is one of the most common types of drug-drug interactions (DDI). When a drug inhibits a specific CYP isoform, it will reduce the metabolic activity toward a concomitant drug that is metabolized by this inhibited CYP isoform, resulting in the increase in the bioavailability of the victim drug, often to a point that toxicity is induced.

Regulatory agencies have issued guidances recommending that all new molecular entity (NME) be screened for CYP inhibition liability, especially for CYP1A2, CYP2B6, CYP2C8, CYP2C9, CYP2C19, CYP2D6, and CYP3A4. To determine the inhibition of the major CYP enzymes, specific drug substrates in human liver microsomes are used.

In this experiment, the inhibition of SIS3 and M00005 on 3 major CYPs (2C9, 2D6 and 3A4) are determined.

3.2 Materials and Methods

3.2.1 Test Article

The compounds used in the study are SIS3 and Compound 8 referred to above and as described with respect to the present invention, as test articles.

Compound 8 is referred to hereinafter as MO-00005.

SIS3 and M00005 are basic compounds. SIS3 is supplied as the hydrochloride salt, and M00005, which is compound 8 referred to above, is supplied as the free base.

3.2.2 Biologics

FAMILY: CYP450
SUB FAMILY: CYP2; CYP3
PROTEIN NAME: CYP2C9, CYP2D6, CYP3A4
UNIPROT NUMBER: P11712, P10635, P08684, P08684
GENE NAME: CYP2C9, CYP2D6, CYP3A4 (midazolam substrate), CYP3A4 (testosterone substrate),
GENE ID: 1559, 1565, 1576,
GENE ALIASES: P450IIC9, CPD6|P450-DB1|CYP2D|,
SPECIES: Human
CONSTRUCT DETAILS: Microsomes

3.2.2 Source

TISSUE: Liver

3.2.3 Assay Information

ASSAY TYPE: Biochemical
ASSAY SUB TYPE: Enzymatic
FUNCTIONAL MODE: Antagonist

3.2.4 Detection Method

HPLC-MS/MS

3.2.5 Measured Response

Peak Area Response

3.2.6 Testing Information

SUBSTRATE: Diclofenac

3.3 Method and Procedure

The method is a general method to determine the CYP inhibition and can be referenced in the following publication:

Elizabeth A. Dierks, Karen R. Stams, Heng-Keang Lim, Georgia Cornelius, Honglu Zhang and Simon E. Ball, "A method for the simultaneous evaluation of the activities of seven major human drug-metabolizing cytochrome P450s using an in vitro cocktail of probe substrates and fast gradient liquid chromatography tandem mass spectrometry". Drug Metabolism and Disposition January 2001, 29 (1) 23-29.

3.4 Results and Discussion

The result for the CYPs inhibition (%) of SIS3 at 10 uM concentration is shown in the following table 9:

TABLE 9

| Assay | Concentration (uM) | Inhibition (%) |
|---|---|---|
| CYP2C9 inhibition (HLM, diclofenac substrate) | 10 | 79.7661 |
| CYP2D6 inhibition (HLM, dextromethorphan substrate) | 10 | 19.1641 |
| CYP3A inhibition (HLM, midazolam substrate) | 10 | 20.5499 |
| CYP3A inhibition (HLM, testosterone substrate) | 10 | 9.29377 |

The result for the CYPs inhibition (%) of MO-0005 at 10 uM concentration is shown in the following table 10:

TABLE 10

| Assay | Concentration (uM) | Inhibition (%) |
|---|---|---|
| CYP2C9 inhibition (HLM, diclofenac substrate) | 10 | 66.9462 |
| CYP2D6 inhibition (HLM, dextromethorphan substrate) | 10 | −2.74E+00 |
| CYP3A inhibition (HLM, midazolam substrate) | 10 | 41.3425 |
| CYP3A inhibition (HLM, testosterone substrate) | 10 | 2.22053 |

3.5 Conclusions and Inferences

From the above result, MO-0005 has less CYP inhibition than SIS3 under the same concentration on $CYP2C_9$, CYP2D6 and CYP3A4 (testosterone substrate).

This indicates the overall superior profile for MO-0005 to SIS3 in terms of potential drug-drug interactions.

4. Combination Therapy

Further, the present invention relates to the use of the novel chemical compounds of the present invention for combination therapy for the treatment and prevention of cancer, particularly to combinations of said the novel chemical compounds with at least one additional anti-cancer therapeutic agent, for enhanced anti-cancer effect, which is preferably synergistic.

The invention claimed is:

1. A compound of Formula 1 (a)(i), or a pharmaceutically acceptable salt thereof:

Formula 1a(i)

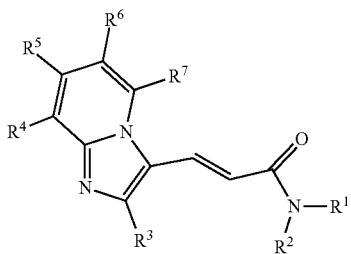

wherein:
the moiety —C(=O)NR'$R^2$ is selected from

Formula 3e(i)

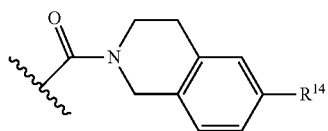

Formula 3e(ii)

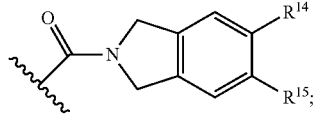

$R^{14}$ and $R^{15}$ are each selected from hydrogen, CN, $NO_2$, OC(O)$R^9$, C(O)$R^9$, C(O)NR$^9$R$^{10}$, C(O)OR$^9$, OR$^9$, OS(O)$_2$R$^9$, NR$^9$R$^{10}$, SR$^9$, and R$^9$;

$R^9$ and $R^{10}$ are each independently selected from hydrogen, $C_{1-10}$alkyl, aryl$C_{1-10}$alkyl, hetaryl$C_{1-10}$alkyl, and heterocyclic; the $C_{1-10}$alkyl moiety of any one of these groups is uninterrupted or interrupted with one or more heteroatoms independently selected from O, N and S; and the $C_{1-10}$alkyl, aryl$C_{1-10}$alkyl, hetaryl$C_{1-10}$alkyl, and heterocyclic groups are each unsubstituted or substituted with 1 to 3 substituents independently selected from halo, CN, $NO_2$, OC(O)$R^{11}$, C(O)$R^{11}$, C(O)NR$^{11}$R$^{12}$, C(O)OR$^{11}$, OR$^{11}$, OS(O)$_2$R$^{11}$, NR$^{11}$R$^{12}$, and SR$^{11}$; and $R^{11}$ and $R^{12}$ are each independently selected from hydrogen, $C_{1-6}$alkyl and $C_{1-6}$alkylhalo;

$R^4$, $R^5$, $R^6$, and $R^7$, are each independently selected from hydrogen, halo, CN, $NO_2$, OC(O)$R^{11}$, C(O)$R^{11}$, C(O)NR$^{11}$R$^{12}$, C(O)OR$^{11}$, OR$^{11}$, OS(O)$_2$R$^{11}$, NR$^{11}$R$^{12}$, SR$^{11}$, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl;
wherein the $C_{1-10}$alkyl, $C_{2-10}$alkenyl and $C_{2-10}$alkynyl groups are each optionally interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, are each optionally substituted with one or more substituents independently selected from halo, CN, $NO_2$, OC(O)$R^{11}$, C(O)$R^{11}$, C(O)NR$^{11}$R$^{12}$, C(O)OR$^{11}$, OR$^{11}$, OS(O)$_2$R$^{11}$, NR$^{11}$R$^{12}$, SR$^{11}$, and R$^{11}$; wherein $R^{11}$ and $R^{12}$ are each independently selected from hydrogen, $C_{1-6}$alkyl, and $C_{1-6}$alkylhalo; and $R^3$ is selected from hydrogen, halo, CN, $NO_2$, OC(O)$R^{11}$, C(O)$R^{11}$, C(O)NR$^{11}$R$^{12}$, C(O)OR$^{11}$, OR$^{11}$, OS(O)$_2$R$^{11}$, NR$^{11}$R$^{12}$, SR$^{11}$, $C_{1-10}$alkyl, $C_{2-10}$alkenyl, $C_{2-10}$alkynyl, $C_{3-10}$cycloalkyl, monocyclic or bicyclic heterocyclic, and monocyclic or bicyclic aryl; wherein the $C_{1-10}$alkyl, $C_{2-10}$alkenyl and $C_{2-10}$alkynyl groups are each uninterrupted or interrupted with one or more heteroatoms selected from O, N and S, and wherein the $C_{1-10}$alkyl, $C_{2-10}$alkenyl, $C_{2-10}$alkynyl, $C_{3-10}$cycloalkyl, heterocyclic, and aryl groups, are each unsubstituted or substituted with one or more substituents independently selected from halo, CN, $NO_2$, OC(O)$R^{11}$, C(O)$R^{11}$, C(O)NR$^{11}$R$^{12}$, C(O)OR$^{11}$, OR$^{11}$, OS(O)$_2$R$^{11}$, NR$^{11}$R$^{12}$, SR$^{11}$, and R$^{11}$; wherein $R^{11}$ is selected from hydrogen, $C_{2-6}$alkyl, and $C_{1-6}$alkylhalo and $R^{12}$ is selected from hydrogen, $C_{1-6}$alkyl, and $C_{1-6}$alkylhalo.

2. The compound according to claim 1, wherein $R^{14}$ and $R^{15}$ are each independently selected from hydrogen, C(O)NR$^9$R$^{10}$, OR$^9$, and NR$^9$R$^{10}$; and $R^9$ and $R^{10}$ are each independently selected from hydrogen, $C_{1-6}$alkyl, monocyclic aryl$C_{1-6}$alkyl, monocyclic hetaryl$C_{1-6}$alkyl, and monocyclic heterocyclic, wherein the $C_{1-6}$alkyl moiety of any one of these groups is optionally interrupted with one or more heteroatoms independently selected from O, N and S, and the $C_{1-6}$alkyl, monocyclic aryl$C_{1-6}$alkyl, monocyclic hetaryl$C_{1-6}$alkyl, and monocyclic heterocyclic, is optionally substituted with 1 to 3 substituents independently selected from halo, CN, $NH_2$, OH, and $OC_{1-6}$alkyl.

3. The compound according to claim 1, wherein $R^4$, $R^5$, $R^6$, and $R^7$, are each independently selected from hydrogen, halo, OH, CN, $NO_2$, $NH_2$, $C_{1-10}$alkyl, monocyclic heterocyclic, and monocyclic aryl; wherein the $C_{1-10}$alkyl is optionally interrupted with one or more heteroatoms selected from O, N and S, and wherein the $C_{1-10}$alkyl, heterocyclic, and aryl groups, are each optionally substituted with one or more substituents independently selected from halo, OH, CN, $NO_2$, $NH_2$, $C_{1-6}$alkyl, and $C_{1-6}$alkylhalo; and $R^3$ is selected from hydrogen, halo, OH, CN, $NO_2$, $NH_2$, $C_{1-10}$alkyl, monocyclic heterocyclic, and monocyclic aryl; wherein the $C_{1-10}$alkyl is uninterrupted or interrupted with one or more heteroatoms selected from O, N and S, and wherein the $C_{1-10}$alkyl, heterocyclic, and aryl groups, are each unsubstituted or substituted with one or more substituents independently selected from halo, OH, CN, $NO_2$, $NH_2$, $C_{2-6}$alkyl, and $C_{1-6}$alkylhalo.

4. The compound according to claim 1, wherein $R^3$ is selected from hydrogen, halo, $C_{1-6}$alkyl, $C_{1-6}$alkylhalo, and monocyclic heterocyclic, and monocyclic aryl or hetaryl.

5. The compound according to claim 1, wherein $R^4$, $R^5$, $R^6$, and $R^7$, are each independently selected from hydrogen, halo, $C_{1-6}$alkyl, and $C_{1-6}$alkylhalo.

6. A compound selected from any one of the following compounds, or a pharmaceutically acceptable salt thereof:

| Compound No. | Compound Structure | Compound Name |
| --- | --- | --- |
| 7 | 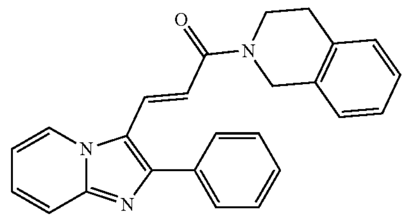 [SMILES: O=C(/C=C/c1c(-c2ccccc2)nc2ccccn12)N1CCc2ccccc2C1] | (E)-1-(3,4-dihydroisoquinolin-2(1H)-yl)-3-(2-phenylimidazo[1,2-a]pyridin-3-yl)prop-2-en-1-one |
| 8 | 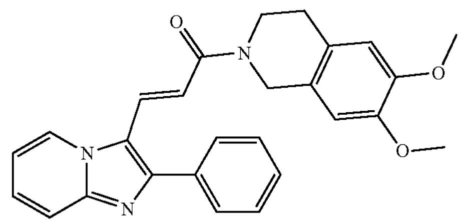 [SMILES: COc1cc2c(cc1OC)CN(C(=O)/C=C/c1c(-c3ccccc3)nc3ccccn13)CC2] | (E)-1-(6,7-dimethoxy-3,4-dihydroisoquinolin-2(1H)-yl)-3-(2-phenylimidazo[1,2-a]pyridin-3-yl)prop-2-en-1-one |
| 9 | 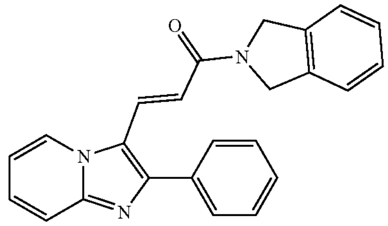 [SMILES: O=C(/C=C/c1c(-c2ccccc2)nc2ccccn12)N1Cc2ccccc2C1] | (E)-1-(isoindolin-2-yl)-3-(2-phenylimidazo[1,2-a]pyridin-3-yl)prop-2-en-1-one |
| 10 | 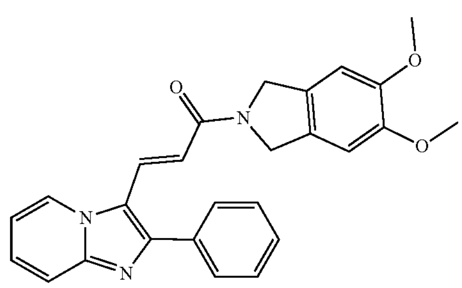 [SMILES: COc1cc2c(cc1OC)CN(C(=O)/C=C/c1c(-c3ccccc3)nc3ccccn13)C2] | (E)-1-(5,6-dimethoxyisoindolin-2-yl)-3-(2-phenylimidazo[1,2-a]pyridin-3-yl)prop-2-en-1-one |
| 11 | 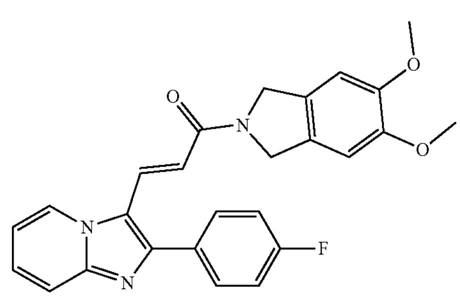 [SMILES: COc1cc2c(cc1OC)CN(C(=O)/C=C/c1c(-c3ccc(F)cc3)nc3ccccn13)C2] | (E)-1-(5,6-dimethoxyisoindolin-2-yl)-3-(2-(4-fluorophenyl)imidazo[1,2-a]pyridin-3-yl)prop-2-en-1-one |

-continued

| Compound No. | Compound Structure | Compound Name |
| --- | --- | --- |
| 12 | 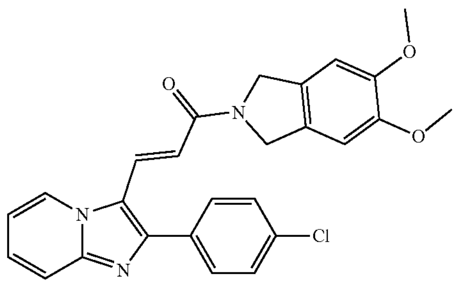 [SMILES: COc1cc2c(cc1OC)CN(C(=O)/C=C/c1c(-c3ccc(Cl)cc3)nc3ccccn13)C2] | (E)-3-(2-(4-chlorophenyl)imidazo[1,2-a]pyridin-3-yl)-1-(5,6-dimethoxyisoindolin-2-yl)prop-2-en-1-one |
| 13 | 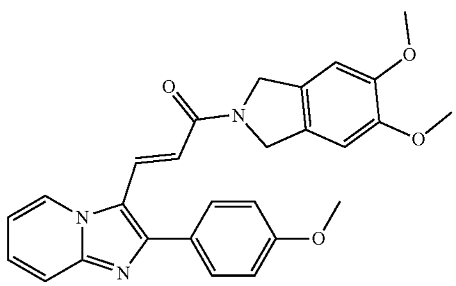 [SMILES: COc1ccc(-c2nc3ccccn3c2/C=C/C(=O)N2Cc3cc(OC)c(OC)cc3C2)cc1] | (E)-1-(5,6-dimethoxyisoindolin-2-yl)-3-(2-(4-methoxyphenyl)imidazo[1,2-a]pyridin-3-yl)prop-2-en-1-one |
| 14 | 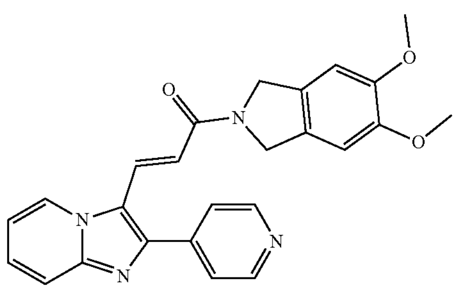 [SMILES: COc1cc2c(cc1OC)CN(C(=O)/C=C/c1c(-c3ccncc3)nc3ccccn13)C2] | (E)-1-(5,6-dimethoxyisoindolin-2-yl)-3-(2-(pyridin-4-yl)imidazo[1,2-a]pyridin-3-yl)prop-2-en-1-one |
| 15 | 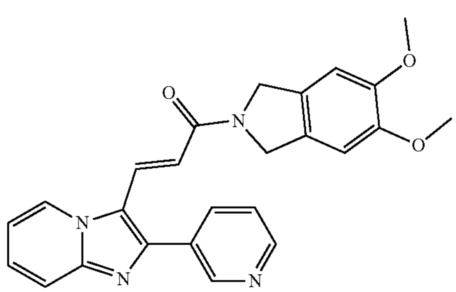 [SMILES: COc1cc2c(cc1OC)CN(C(=O)/C=C/c1c(-c3cccnc3)nc3ccccn13)C2] | (E)-1-(5,6-dimethoxyisoindolin-2-yl)-3-(2-(pyridin-3-yl)imidazo[1,2-a]pyridin-3-yl)prop-2-en-1-one |
| 16 | 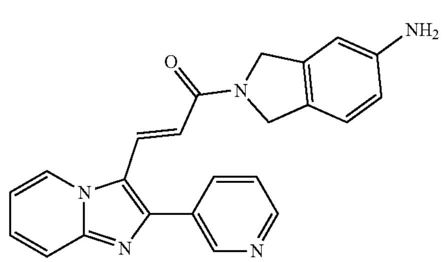 [SMILES: Nc1ccc2c(c1)CN(C(=O)/C=C/c1c(-c3cccnc3)nc3ccccn13)C2] | (E)-1-(5-aminoisoindolin-2-yl)-3-(2-(pyridin-3-yl)imidazo[1,2-a]pyridin-3-yl)prop-2-en-1-one |

-continued

| Compound No. | Compound Structure | Compound Name |
|---|---|---|
| 17 | 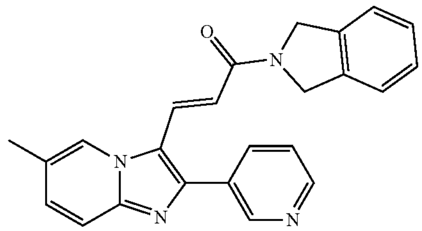 [SMILES: Cc1ccc2nc(-c3cccnc3)c(/C=C/C(=O)N3Cc4ccccc4C3)n2c1] | (E)-1-(isoindolin-2-yl)-3-(6-methyl-2-(pyridin-3-yl)imidazo[1,2-a]pyridin-3-yl)prop-2-en-1-one |
| 18 | 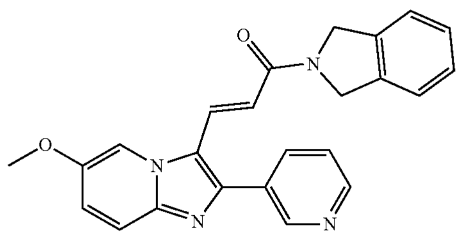 [SMILES: COc1ccc2nc(-c3cccnc3)c(/C=C/C(=O)N3Cc4ccccc4C3)n2c1] | (E)-1-(isoindolin-2-yl)-3-(6-methoxy-2-(pyridin-3-yl)imidazo[1,2-a]pyridin-3-yl)prop-2-en-1-one |
| 19 | 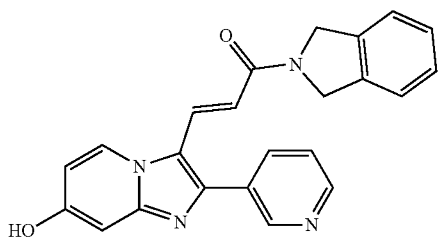 [SMILES: O=C(/C=C/c1c(-c2cccnc2)nc2cc(O)ccn12)N1Cc2ccccc2C1] | (E)-3-(7-hydroxy-2-(pyridin-3-yl)imidazo[1,2-alpyridin-3-yl)-1-(isoindolin-2-yl)prop-2-en-1-one |
| 20 | 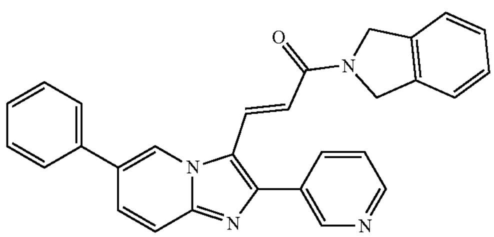 [SMILES: O=C(/C=C/c1c(-c2cccnc2)nc2ccc(-c3ccccc3)cn12)N1Cc2ccccc2C1] | (E)-1-(isoindolin-2-yl)-3-(6-phenyl-2-(pyridin-3-yl)imidazo[1,2-a]pyridin-3-yl)prop-2-en-1-one |
| 21 | 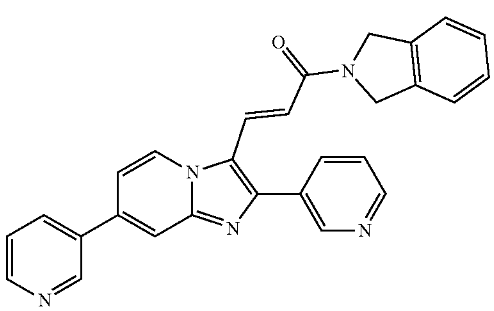 [SMILES: O=C(/C=C/c1c(-c2cccnc2)nc2cc(-c3cccnc3)ccn12)N1Cc2ccccc2C1] | (E)-3-(2,7-di(pyridin-3-yl)imidazo[1,2-a]pyridin-3-yl)-1-(isoindolin-2-yl)prop-2-en-1-one |
| 22 | 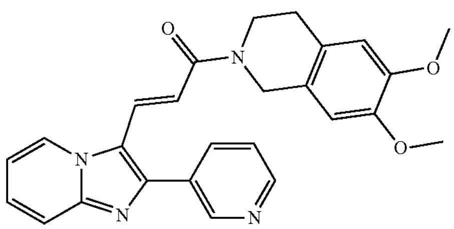 [SMILES: COc1cc2c(cc1OC)CN(C(=O)/C=C/c1c(-c3cccnc3)nc3ccccn13)CC2] | (E)-1-(6,7-dimethoxy-3,4-dihydroisoquinolin-2(1H)-yl)-3-(2-(pyridin-3-yl)imidazo[1,2-a]pyridin-3-yl)prop-2-en-1-one |

| Compound No. | Compound Structure | Compound Name |
|---|---|---|
| 23 | 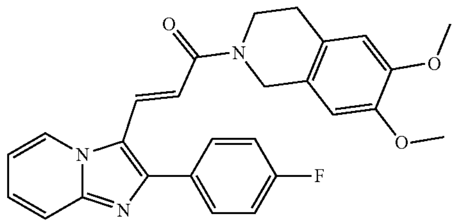 [SMILES: COc1cc2c(cc1OC)CN(C(=O)/C=C/c1c(-c3ccc(F)cc3)nc3ccccn13)CC2] | (E)-1-(6,7-dimethoxy-3,4-dihydroisoquinolin-2(1H)-yl)-3-(2-(4-fluorophenyl)imidazo[1,2-a]pyridin-3-yl)prop-2-en-1-one |
| 24 | 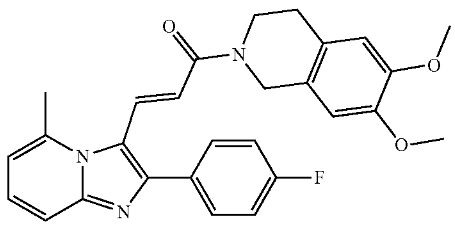 [SMILES: COc1cc2c(cc1OC)CN(C(=O)/C=C/c1c(-c3ccc(F)cc3)nc3cccc(C)n13)CC2] | (E)-1-(6,7-dimethoxy-3,4-dihydroisoquinolin-2(1H)-yl)-3-(2-(4-fluorophenyl)-5-methylimidazo[1,2-a]pyridin-3-yl)prop-2-en-1-one |
| 25 | 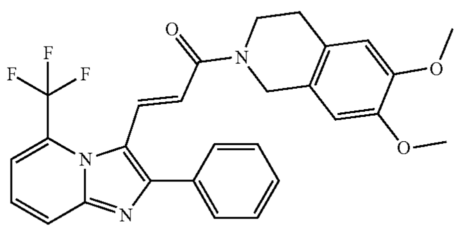 [SMILES: COc1cc2c(cc1OC)CN(C(=O)/C=C/c1c(-c3ccccc3)nc3cccc(C(F)(F)F)n13)CC2] | (E)-1-(6,7-dimethoxy-3,4-dihydroisoquinolin-2(1H)-yl)-3-(2-phenyl-5-(trifluoromethyl)imidazo[1,2-a]pyridin-3-yl)prop-2-en-1-one |

7. A pharmaceutical composition comprising a compound according to claim 1 and a pharmaceutically acceptable excipient.

8. A method of treatment comprising inhibiting or preventing proliferation of a cell, comprising contacting the cell with a therapeutically effective amount of a compound according to claim 1, or a pharmaceutically acceptable salt thereof, to a patient in need thereof.

9. A method of treating cancer comprising administering a therapeutically effective amount of a compound according to claim 1, or a pharmaceutically acceptable salt thereof, to a patient in need thereof, wherein the cancer is melanoma.

10. The method of claim 9, further comprising administering an effective amount of at least one additional anticancer agent to the patient.

11. The compound of claim 1, wherein the moiety —C(═O)NR$^1$R$^2$ is Formula 3e(i).

Formula 3e(i)

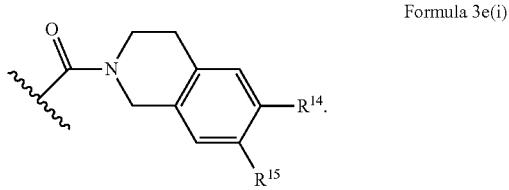

12. The compound of claim 1, wherein R$^4$, R$^5$, R$^6$, and R$^7$ are each hydrogen.

13. The compound of claim 1, wherein R$^3$ is selected from hydrogen, halo, C$_{1-6}$alkyl, C$_{1-6}$alkylhalo, and monocyclic or bicyclic heterocyclic, and monocyclic or bicyclic aryl or hetaryl, wherein the aryl and hetaryl groups are unsubstituted or substituted with one or more substituents independently selected from halo, OH, CN, NO$_2$, NH$_2$, C$_{2-6}$alkyl, and C$_{1-6}$alkylhalo.

14. The compound of claim 1, wherein R$^3$ is selected from hydrogen and monocyclic or bicyclic aryl and hetaryl, wherein the aryl and hetaryl groups are unsubstituted or substituted with one or more substituents independently selected from halo, OH, CN, NO, NH$_2$, C$_{2-6}$alkyl, and C$_{1-6}$alkylhalo.

15. The compound of claim 1, wherein R$^3$ may be selected from hydrogen and monocyclic aryl, wherein the aryl group is unsubstituted or substituted with one or more substituents independently selected from halo, OH, CN, NO$_2$, NH$_2$, C$_{2-6}$alkyl, and C$_{1-6}$alkylhalo.

16. The compound of claim 1, wherein R$^3$ is phenyl, which is unsubstituted or substituted with one or more substituents independently selected from halo, OH, CN, NO$_2$, NH$_2$, C$_{2-6}$alkyl, and C$_{1-6}$alkylhalo.

* * * * *

UNITED STATES PATENT AND TRADEMARK OFFICE
CERTIFICATE OF CORRECTION

PATENT NO. : 12,090,149 B2
APPLICATION NO. : 17/265502
DATED : September 17, 2024
INVENTOR(S) : Ho Yin Lo It is certified that error appears in the above-identified patent and that said Letters Patent is hereby corrected as shown below:

In the Claims

Claim 1, Column 113, Line 51 – Replace "—C(=O)NR'R$^2$" with "—C(=O)NR$^1$R$^2$"

Claim 6, Column 116, Compound No. 7 – Replace "(E)-1-(3,4-dihydroisoquinolin-2(1H)-yl)-3-(2-phenylimidazo[1,2-alpyridin-3-yl)prop-2-en-1-one" with "(E)-1-(3,4-dihydroisoquinolin-2(1H)-yl)-3-(2-phenylimidazo[1,2-a]pyridin-3-yl)prop-2-en-1-one"

Claim 6, Column 116, Compound No. 8 – Replace "(E)-1-(6,7-dimethoxy-3,4-dihydroisoquinolin-2(1H)-yl)-3-(2-phenylimidazo[1,2-alpyridin-3-yl)prop-2-en-1-one" with "(E)-1-(6,7-dimethoxy-3,4-dihydroisoquinolin-2(1H)-yl)-3-(2-phenylimidazo[1,2-a]pyridin-3-yl)prop-2-en-1-one"

Claim 6, Column 116, Compound No. 10 – Replace "(E)-1-(5,6-dimethoxyisoindolin-2-yl)-3-(2-phenylimidazo[1,2-alpyridin-3-yl)prop-2-en-1-one" with "(E)-1-(5,6-dimethoxyisoindolin-2-yl)-3-(2-phenylimidazo[1,2-a]pyridin-3-yl)prop-2-en-1-one"

Claim 6, Column 117, Compound No. 12 – Replace "(E)-3-(2-(4-chlorophenyl)imidazo[1,2-alpyridin-3-yl)-1-(5,6-dimethoxyisoindolin-2-yl)prop-2-en-1-one" with "(E)-3-(2-(4-chlorophenyl)imidazo[1,2-a]pyridin-3-yl)-1-(5,6-dimethoxyisoindolin-2-yl)prop-2-en-1-one"

Claim 6, Column 119, Compound No. 19 – Replace "(E)-3-(7-hydroxy-2-(pyridin-3-yl)imidazo[1,2-alpyridin-3-yl)-1-(isoindolin-2-yl)prop-2-en-1-one" with "(E)-3-(7-hydroxy-2-(pyridin-3-yl)imidazo[1,2-a]pyridin-3-yl)-1-(isoindolin-2-yl)prop-2-en-1-one"

Claim 6, Column 121, Compound No. 24 – Replace "(E)-1-(6,7-dimethoxy-3,4-dihydroisoquinolin-2(1H)-yl)-3-(2-(4-fluorophenyl)-5-methylimidazo[1,2-alpyridin-3-yl)prop-2-en-1-one" with "(E)-1-(6,7-dimethoxy-3,4-dihydroisoquinolin-2(1H)-yl)-3-(2-(4-fluorophenyl)-5-methylimidazo[1,2-a]pyridin-3-yl)prop-2-en-1-one"

Signed and Sealed this
Fifth Day of November, 2024

Katherine Kelly Vidal
*Director of the United States Patent and Trademark Office*